US011850020B2

(12) United States Patent
Mensinger et al.

(10) Patent No.: US 11,850,020 B2
(45) Date of Patent: *Dec. 26, 2023

(54) REMOTE MONITORING OF ANALYTE MEASUREMENTS

(71) Applicant: Dexcom, Inc., San Diego, CA (US)

(72) Inventors: Michael Robert Mensinger, San Diego, CA (US); Eric Cohen, San Diego, CA (US); Philip Mayou, San Diego, CA (US); Eli Reihman, San Diego, CA (US); Katherine Yerre Koehler, Solana Beach, CA (US); Rian Draeger, San Diego, CA (US); Angela Marie Traven, San Marcos, CA (US)

(73) Assignee: Dexcom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/812,083

(22) Filed: Jul. 12, 2022

(65) Prior Publication Data

US 2022/0346646 A1    Nov. 3, 2022

Related U.S. Application Data

(63) Continuation of application No. 17/396,502, filed on Aug. 6, 2021, now Pat. No. 11,382,508, which is a
(Continued)

(51) Int. Cl.
*A61B 5/00* (2006.01)
*H04L 67/12* (2022.01)
(Continued)

(52) U.S. Cl.
CPC .......... *A61B 5/0004* (2013.01); *A61B 5/0002* (2013.01); *A61B 5/0022* (2013.01);
(Continued)

(58) Field of Classification Search
CPC ... A61B 5/0004; A61B 5/0002; A61B 5/0022; A61B 5/145; A61B 5/14532;
(Continued)

(56) References Cited

U.S. PATENT DOCUMENTS 612,939 A    10/1898  Willson, Jr.
4,757,022 A   7/1988  Shults et al.
(Continued)

FOREIGN PATENT DOCUMENTS

CN    1244104 A    2/2000
CN    1432166 A    7/2003
(Continued)

OTHER PUBLICATIONS

American Diabetes Association, "Position Statement: Standards of Medical Care in Diabetes," Diabetes Care, vol. 32, Supplement 01, Jan. 2009, pp. S13-S61.
(Continued)

*Primary Examiner* — Franklin D Balseca
(74) *Attorney, Agent, or Firm* — PATTERSON & SHERIDAN, LLP

(57) ABSTRACT

Methods and apparatus, including computer program products, are provided for remote monitoring. In some example implementations, there is provided a method. The method may include receiving, at a remote monitor, a notification message representative of an event detected, by a server, from analyte sensor data obtained from a receiver monitoring an analyte state of a host; presenting, at the remote monitor, the notification message to activate the remote monitor, wherein the remote monitor is configured by the server to receive the notification message to augment the receiver monitoring of the analyte state of the host; accessing, by the remote monitor, the server, in response to the presenting of the notification message; and receiving, in
(Continued)

response to the accessing, information including at least the analyte sensor data. Related systems, methods, and articles of manufacture are also disclosed.

17 Claims, 23 Drawing Sheets

Related U.S. Application Data continuation of application No. 17/133,339, filed on Dec. 23, 2020, now Pat. No. 11,109,757, which is a continuation of application No. 16/934,987, filed on Jul. 21, 2020, now Pat. No. 10,993,617, which is a continuation of application No. 16/831,648, filed on Mar. 26, 2020, now Pat. No. 10,856,736, which is a continuation of application No. 16/591,439, filed on Oct. 2, 2019, now abandoned, which is a continuation of application No. 14/945,263, filed on Nov. 18, 2015, now Pat. No. 10,667,686, which is a continuation of application No. 13/842,679, filed on Mar. 15, 2013, now Pat. No. 9,801,541.

(60) Provisional application No. 61/747,717, filed on Dec. 31, 2012.

(51) Int. Cl.
    *A61B 5/1486* (2006.01)
    *A61B 5/145* (2006.01)
    *G16H 40/67* (2018.01)
    *A61B 5/02* (2006.01)
    *H04Q 9/00* (2006.01)
    *G16H 40/63* (2018.01)
    *G16H 15/00* (2018.01)
    *G16H 20/00* (2018.01)
    *G16H 10/60* (2018.01)
    *G16H 40/20* (2018.01)
    *G16H 50/70* (2018.01)
    *G16H 50/20* (2018.01)
    *G16H 20/40* (2018.01)

(52) U.S. Cl.
    CPC ............ *A61B 5/145* (2013.01); *A61B 5/1486* (2013.01); *A61B 5/14532* (2013.01); *A61B 5/7264* (2013.01); *A61B 5/7282* (2013.01); *A61B 5/742* (2013.01); *A61B 5/743* (2013.01); *A61B 5/746* (2013.01); *G16H 40/67* (2018.01); *H04L 67/12* (2013.01); *A61B 5/0015* (2013.01); *A61B 5/0024* (2013.01); *A61B 5/02* (2013.01); *A61B 5/14546* (2013.01); *A61B 5/7435* (2013.01); *A61B 5/7465* (2013.01); *G16H 10/60* (2018.01); *G16H 15/00* (2018.01); *G16H 20/00* (2018.01); *G16H 20/40* (2018.01); *G16H 40/20* (2018.01); *G16H 40/63* (2018.01); *G16H 50/20* (2018.01); *G16H 50/70* (2018.01); *H04Q 9/00* (2013.01); *H04Q 2209/00* (2013.01); *H04Q 2209/10* (2013.01); *H04Q 2209/40* (2013.01); *H04Q 2209/50* (2013.01); *H04Q 2209/70* (2013.01)

(58) Field of Classification Search
    CPC ... A61B 5/1486; A61B 5/7264; A61B 5/7282; A61B 5/742; A61B 5/743; A61B 5/746; A61B 5/0015; A61B 5/0024; A61B 5/02; A61B 5/14546; A61B 5/7435; A61B 5/7465; G16H 40/67; G16H 40/20; G16H 40/63; G16H 20/40; G16H 20/00; G16H 10/60; G16H 15/00; G16H 50/70; G16H 50/20; H04L 67/12; H04Q 9/00; H04Q 2209/00; H04Q 2209/10; H04Q 2209/40; H04Q 2209/50; H04Q 2209/70

See application file for complete search history.

(56) References Cited

U.S. PATENT DOCUMENTS

| 4,994,167 | A | 2/1991 | Shults et al. |
|---|---|---|---|
| 5,572,999 | A | 11/1996 | Funda et al. |
| 5,590,648 | A | 1/1997 | Mitchell et al. |
| 5,832,448 | A | 11/1998 | Brown |
| 5,897,493 | A | 4/1999 | Brown |
| 5,970,457 | A | 10/1999 | Brant et al. |
| 6,001,067 | A | 12/1999 | Shults et al. |
| 6,053,887 | A | 4/2000 | Levitas et al. |
| 6,101,478 | A | 8/2000 | Brown |
| 6,168,563 | B1 | 1/2001 | Brown |
| 6,224,542 | B1 | 5/2001 | Chang et al. |
| 6,234,964 | B1 | 5/2001 | Iliff |
| 6,270,455 | B1 | 8/2001 | Brown |
| 6,278,975 | B1 | 8/2001 | Brant et al. |
| 6,334,778 | B1 | 1/2002 | Brown |
| 6,364,834 | B1 | 4/2002 | Reuss et al. |
| 6,366,871 | B1 | 4/2002 | Geva |
| 6,368,273 | B1 | 4/2002 | Brown |
| 6,415,166 | B1 | 7/2002 | Van Hoy et al. |
| 6,416,471 | B1 | 7/2002 | Kumar et al. |
| 6,424,847 | B1 | 7/2002 | Mastrototaro et al. |
| 6,442,432 | B2 | 8/2002 | Lee |
| 6,447,424 | B1 | 9/2002 | Ashby et al. |
| 6,463,361 | B1 | 10/2002 | Wang et al. |
| 6,477,395 | B2 | 11/2002 | Schulman et al. |
| 6,477,424 | B1 | 11/2002 | Thompson et al. |
| 6,484,046 | B1 | 11/2002 | Say et al. |
| 6,492,901 | B1 | 12/2002 | Ridolfo |
| 6,544,174 | B2 | 4/2003 | West et al. |
| 6,558,320 | B1 | 5/2003 | Causey, III et al. |
| 6,558,321 | B1 | 5/2003 | Burd et al. |
| 6,564,104 | B2 | 5/2003 | Nelson et al. |
| 6,565,509 | B1 | 5/2003 | Say et al. |
| 6,579,690 | B1 | 6/2003 | Bonnecaze et al. |
| 6,585,644 | B2 | 7/2003 | Lebel et al. |
| 6,592,528 | B2 | 7/2003 | Amano |
| 6,602,191 | B2 | 8/2003 | Quy |
| 6,638,223 | B2 | 10/2003 | Lifshitz et al. |
| 6,641,533 | B2 | 11/2003 | Causey, III et al. |
| 6,645,142 | B2 | 11/2003 | Braig et al. |
| 6,669,631 | B2 | 12/2003 | Norris et al. |
| 6,702,857 | B2 | 3/2004 | Brauker et al. |
| 6,735,479 | B2 | 5/2004 | Fabian et al. |
| 6,741,877 | B1 | 5/2004 | Shults et al. |
| 6,775,577 | B2 | 8/2004 | Crnkovich et al. |
| 6,816,241 | B2 | 11/2004 | Grubisic |
| 6,862,465 | B2 | 3/2005 | Shults et al. |
| 6,893,396 | B2 | 5/2005 | Schulze et al. |
| 6,931,327 | B2 | 8/2005 | Goode, Jr. et al. |
| 6,943,787 | B2 | 9/2005 | Webb |
| 6,950,708 | B2 | 9/2005 | Bowman, IV et al. |
| 6,957,102 | B2 | 10/2005 | Silver et al. |
| 6,958,705 | B2 | 10/2005 | Lebel et al. |
| 7,026,929 | B1 | 4/2006 | Wallace |
| 7,074,307 | B2 | 7/2006 | Simpson et al. |
| 7,081,195 | B2 | 7/2006 | Simpson et al. |
| 7,088,233 | B2 | 8/2006 | Menard |
| 7,103,578 | B2 | 9/2006 | Beck et al. |
| 7,108,778 | B2 | 9/2006 | Simpson et al. |
| 7,110,803 | B2 | 9/2006 | Shults et al. |
| 7,134,994 | B2 | 11/2006 | Alpert et al. |
| 7,134,999 | B2 | 11/2006 | Brauker et al. |
| 7,136,689 | B2 | 11/2006 | Shults et al. |
| 7,171,274 | B2 | 1/2007 | Starkweather et al. |
| 7,192,450 | B2 | 3/2007 | Brauker et al. |
| 7,219,303 | B2 | 5/2007 | Fish |
| 7,226,978 | B2 | 6/2007 | Tapsak et al. |
| 7,256,708 | B2 | 8/2007 | Rosenfeld et al. |

(56) References Cited

U.S. PATENT DOCUMENTS

| | | |
|---|---|---|
| 7,276,029 B2 | 10/2007 | Goode, Jr. et al. |
| 7,278,983 B2 | 10/2007 | Ireland et al. |
| 7,294,105 B1 | 11/2007 | Islam |
| 7,301,451 B2 | 11/2007 | Hastings |
| 7,310,544 B2 | 12/2007 | Brister et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,399,277 B2 | 7/2008 | Saidara et al. |
| 7,424,318 B2 | 9/2008 | Brister et al. |
| 7,448,996 B2 | 11/2008 | Khanuja et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,430 B2 | 4/2009 | Von Arx et al. |
| 7,565,197 B2 | 7/2009 | Haubrich et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,368 B2 | 11/2009 | Brown |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,643,798 B2 | 1/2010 | Ljung |
| 7,651,596 B2 | 1/2010 | Petisce et al. |
| 7,654,956 B2 | 2/2010 | Brister et al. |
| 7,657,297 B2 | 2/2010 | Simpson et al. |
| 7,685,005 B2 | 3/2010 | Riff et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,761,130 B2 | 7/2010 | Simpson et al. |
| 7,771,352 B2 | 8/2010 | Shults et al. |
| 7,774,145 B2 | 8/2010 | Brauker et al. |
| 7,775,975 B2 | 8/2010 | Brister et al. |
| 7,778,680 B2 | 8/2010 | Goode, Jr. et al. |
| 7,783,333 B2 | 8/2010 | Brister et al. |
| 7,792,562 B2 | 9/2010 | Shults et al. |
| 7,797,028 B2 | 9/2010 | Goode, Jr. et al. |
| 7,811,231 B2 | 10/2010 | Jin et al. |
| 7,826,981 B2 | 11/2010 | Goode, Jr. et al. |
| 7,828,728 B2 | 11/2010 | Boock et al. |
| 7,831,287 B2 | 11/2010 | Brister et al. |
| 7,835,777 B2 | 11/2010 | Shults et al. |
| 7,857,760 B2 | 12/2010 | Brister et al. |
| 7,860,545 B2 | 12/2010 | Shults et al. |
| 7,875,293 B2 | 1/2011 | Shults et al. |
| 7,881,763 B2 | 2/2011 | Brauker et al. |
| 7,885,697 B2 | 2/2011 | Brister et al. |
| 7,896,809 B2 | 3/2011 | Simpson et al. |
| 7,899,511 B2 | 3/2011 | Shults et al. |
| 7,901,354 B2 | 3/2011 | Shults et al. |
| 7,905,833 B2 | 3/2011 | Brister et al. |
| 7,914,450 B2 | 3/2011 | Goode, Jr. et al. |
| 7,917,186 B2 | 3/2011 | Kamath et al. |
| 7,920,906 B2 | 4/2011 | Goode, Jr. et al. |
| 7,925,321 B2 | 4/2011 | Goode, Jr. et al. |
| 7,927,274 B2 | 4/2011 | Rasdal et al. |
| 7,933,639 B2 | 4/2011 | Goode et al. |
| 7,933,781 B2 | 4/2011 | Bjorlin et al. |
| 7,935,057 B2 | 5/2011 | Goode, Jr. et al. |
| 7,946,984 B2 | 5/2011 | Brister et al. |
| 7,946,995 B1 | 5/2011 | Koh et al. |
| 7,949,381 B2 | 5/2011 | Brister et al. |
| 7,955,261 B2 | 6/2011 | Goode et al. |
| 7,959,569 B2 | 6/2011 | Goode et al. |
| 7,970,448 B2 | 6/2011 | Shults et al. |
| 7,974,672 B2 | 7/2011 | Shults et al. |
| 7,976,492 B2 | 7/2011 | Brauker et al. |
| 7,979,104 B2 | 7/2011 | Kamath et al. |
| 7,981,034 B2 | 7/2011 | Jennewine et al. |
| 7,986,986 B2 | 7/2011 | Goode et al. |
| 7,998,071 B2 | 8/2011 | Goode, Jr. et al. |
| 8,000,901 B2 | 8/2011 | Brauker et al. |
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,050,731 B2 | 11/2011 | Tapsak et al. |
| 8,052,601 B2 | 11/2011 | Goode, Jr. et al. |
| 8,053,018 B2 | 11/2011 | Tapsak et al. |
| 8,060,173 B2 | 11/2011 | Goode, Jr. et al. |
| 8,060,174 B2 | 11/2011 | Simpson et al. |
| 8,064,977 B2 | 11/2011 | Boock et al. |
| 8,073,008 B2 | 12/2011 | Mehta et al. |
| 8,073,519 B2 | 12/2011 | Goode, Jr. et al. |
| 8,073,520 B2 | 12/2011 | Kamath et al. |
| 8,085,151 B2 | 12/2011 | Jennewine |
| 8,086,292 B2 | 12/2011 | Peyser |
| 8,095,692 B2 | 1/2012 | Mehta et al. |
| 8,112,240 B2 | 2/2012 | Fennell |
| 8,118,877 B2 | 2/2012 | Brauker et al. |
| 8,121,857 B2 | 2/2012 | Galasso et al. |
| 8,128,562 B2 | 3/2012 | Goode, Jr. et al. |
| 8,131,566 B2 | 3/2012 | Dicks et al. |
| 8,133,178 B2 | 3/2012 | Brauker et al. |
| 8,150,488 B2 | 4/2012 | Goode, Jr. et al. |
| 8,155,723 B2 | 4/2012 | Shults et al. |
| 8,160,669 B2 | 4/2012 | Brauker et al. |
| 8,160,671 B2 | 4/2012 | Kamath et al. |
| 8,167,801 B2 | 5/2012 | Goode, Jr. et al. |
| 8,170,803 B2 | 5/2012 | Kamath et al. |
| 8,180,591 B2 | 5/2012 | Yuen et al. |
| 8,195,265 B2 | 6/2012 | Goode, Jr. et al. |
| 8,206,297 B2 | 6/2012 | Kamath et al. |
| 8,208,973 B2 | 6/2012 | Mehta |
| 8,216,139 B2 | 7/2012 | Brauker et al. |
| 8,229,534 B2 | 7/2012 | Brister et al. |
| 8,229,535 B2 | 7/2012 | Mensinger et al. |
| 8,229,536 B2 | 7/2012 | Goode, Jr. et al. |
| 8,231,531 B2 | 7/2012 | Brister et al. |
| 8,233,958 B2 | 7/2012 | Brauker et al. |
| 8,233,959 B2 | 7/2012 | Kamath et al. |
| 8,249,684 B2 | 8/2012 | Kamath et al. |
| 8,251,906 B2 | 8/2012 | Brauker et al. |
| 8,255,030 B2 | 8/2012 | Petisce et al. |
| 8,255,032 B2 | 8/2012 | Petisce et al. |
| 8,255,033 B2 | 8/2012 | Petisce et al. |
| 8,257,259 B2 | 9/2012 | Brauker et al. |
| 8,260,393 B2 | 9/2012 | Kamath et al. |
| 8,265,725 B2 | 9/2012 | Brauker et al. |
| 8,275,437 B2 | 9/2012 | Brauker et al. |
| 8,275,438 B2 | 9/2012 | Simpson et al. |
| 8,277,713 B2 | 10/2012 | Petisce et al. |
| 8,280,475 B2 | 10/2012 | Brister et al. |
| 8,282,549 B2 | 10/2012 | Brauker et al. |
| 8,282,550 B2 | 10/2012 | Rasdal et al. |
| 8,285,354 B2 | 10/2012 | Goode et al. |
| 8,287,453 B2 | 10/2012 | Li et al. |
| 8,290,559 B2 | 10/2012 | Shariati et al. |
| 8,290,560 B2 | 10/2012 | Kamath et al. |
| 8,290,561 B2 | 10/2012 | Brauker et al. |
| 8,290,562 B2 | 10/2012 | Goode, Jr. et al. |
| 8,292,810 B2 | 10/2012 | Goode, Jr. et al. |
| 8,298,142 B2 | 10/2012 | Simpson et al. |
| 8,311,749 B2 | 11/2012 | Brauker et al. |
| 8,313,434 B2 | 11/2012 | Brister et al. |
| 8,321,149 B2 | 11/2012 | Brauker et al. |
| 8,323,189 B2 | 12/2012 | Tran et al. |
| 8,332,008 B2 | 12/2012 | Goode et al. |
| 8,346,338 B2 | 1/2013 | Goode, Jr. et al. |
| 8,355,320 B1 | 1/2013 | Dhiman et al. |
| 8,364,229 B2 | 1/2013 | Simpson et al. |
| 8,369,919 B2 | 2/2013 | Kamath et al. |
| 8,374,667 B2 | 2/2013 | Brauker et al. |
| 8,381,268 B2 | 2/2013 | Winget et al. |
| 8,386,004 B2 | 2/2013 | Kamath et al. |
| 8,394,021 B2 | 3/2013 | Goode et al. |
| 8,409,093 B2 | 4/2013 | Bugler |
| 8,412,185 B2 | 4/2013 | Cader et al. |

(56) References Cited

U.S. PATENT DOCUMENTS

| | | |
|---|---|---|
| 8,416,085 B2 | 4/2013 | Gawlick |
| 8,432,260 B2 | 4/2013 | Talty et al. |
| 8,472,108 B2 | 6/2013 | Islam |
| 8,510,126 B2 | 8/2013 | Martin et al. |
| 8,514,086 B2 | 8/2013 | Harper et al. |
| 8,515,777 B1 | 8/2013 | Rajasenan |
| 8,527,025 B1 | 9/2013 | Shults et al. |
| 8,527,449 B2 | 9/2013 | Gajic et al. |
| 8,549,600 B2 | 10/2013 | Shedrinsky |
| 8,638,397 B2 | 1/2014 | Ueno et al. |
| 8,696,565 B2 | 4/2014 | Alberte, Jr. et al. |
| 8,704,656 B2 | 4/2014 | Abedi |
| 8,784,271 B2 | 7/2014 | Brumback et al. |
| 8,786,425 B1 | 7/2014 | Hutz |
| 8,789,156 B2 | 7/2014 | Fisk et al. |
| 8,821,622 B2 | 9/2014 | Manahan et al. |
| 8,912,897 B2 | 12/2014 | Carnes |
| 8,926,509 B2 | 1/2015 | Magar et al. |
| 8,965,477 B2 | 2/2015 | Hoss et al. |
| 8,968,198 B2 | 3/2015 | Brauker et al. |
| 8,983,616 B2 | 3/2015 | Kaula et al. |
| 9,011,332 B2 | 4/2015 | Heller et al. |
| 9,028,410 B2 | 5/2015 | San Vicente et al. |
| 9,035,744 B2 | 5/2015 | Waniss |
| 9,079,033 B2 | 7/2015 | Kuenzler et al. |
| 9,198,623 B2 | 12/2015 | Fern et al. |
| 9,204,808 B2 | 12/2015 | Riedel |
| 9,232,916 B2 | 1/2016 | Mao et al. |
| 9,363,337 B2 | 6/2016 | Chor |
| 9,445,445 B2 | 9/2016 | Miller et al. |
| 9,451,910 B2 | 9/2016 | Brister et al. |
| 9,503,526 B2 | 11/2016 | Daoud et al. |
| 9,532,737 B2 | 1/2017 | Karan et al. |
| 9,579,053 B2 | 2/2017 | Brister et al. |
| 9,585,563 B2 | 3/2017 | Mensinger et al. |
| 9,655,518 B2 | 5/2017 | Lin |
| 9,662,438 B2 | 5/2017 | Kamen et al. |
| 9,668,682 B2 | 6/2017 | Brister et al. |
| 9,681,807 B2 | 6/2017 | Miller et al. |
| 9,724,028 B2 | 8/2017 | Brauker et al. |
| 9,730,620 B2 | 8/2017 | Cohen et al. |
| 9,730,621 B2 | 8/2017 | Cohen et al. |
| 9,788,354 B2 | 10/2017 | Miller et al. |
| 9,788,766 B2 | 10/2017 | Simpson et al. |
| 9,801,541 B2 | 10/2017 | Mensinger et al. |
| 9,839,353 B2 | 12/2017 | Mensinger et al. |
| 9,854,972 B2 | 1/2018 | Mensinger et al. |
| 9,931,036 B2 | 4/2018 | Miller et al. |
| 9,931,037 B2 | 4/2018 | Miller et al. |
| 9,962,081 B2 | 5/2018 | Mensinger et al. |
| 9,980,646 B2 | 5/2018 | Mensinger et al. |
| 10,376,188 B2 | 8/2019 | Simpson et al. |
| 10,499,811 B2 | 12/2019 | Mensinger et al. |
| 10,667,686 B2 | 6/2020 | Mensinger et al. |
| 10,856,736 B2 | 12/2020 | Mensinger et al. |
| 10,860,687 B2 | 12/2020 | Cohen et al. |
| 10,869,599 B2 | 12/2020 | Mensinger et al. |
| 11,043,300 B2 | 6/2021 | Reggiardo et al. |
| 11,152,112 B2 | 10/2021 | Nekoomaram et al. |
| 11,166,650 B2 | 11/2021 | Tubb |
| 2001/0023360 A1 | 9/2001 | Nelson et al. |
| 2002/0016719 A1 | 2/2002 | Nemeth et al. |
| 2002/0019584 A1 | 2/2002 | Schulze et al. |
| 2002/0045808 A1 | 4/2002 | Ford et al. |
| 2002/0061092 A1 | 5/2002 | Maropis et al. |
| 2002/0065453 A1 | 5/2002 | Lesho et al. |
| 2002/0068858 A1 | 6/2002 | Braig et al. |
| 2002/0169584 A1 | 11/2002 | Fu et al. |
| 2002/0169587 A1 | 11/2002 | Emek et al. |
| 2002/0195997 A1 | 12/2002 | Peek et al. |
| 2003/0028184 A1 | 2/2003 | Lebel et al. |
| 2003/0032874 A1 | 2/2003 | Rhodes et al. |
| 2003/0060692 A1 | 3/2003 | Ruchti et al. |
| 2003/0149526 A1 | 8/2003 | Zhou et al. |
| 2003/0208465 A1 | 11/2003 | Yurko et al. |
| 2004/0015132 A1 | 1/2004 | Brown |
| 2004/0030753 A1 | 2/2004 | Horvitz |
| 2004/0044272 A1 | 3/2004 | Moerman et al. |
| 2004/0102683 A1 | 5/2004 | Khanuja et al. |
| 2004/0236189 A1 | 11/2004 | Hawthorne et al. |
| 2004/0243941 A1 | 12/2004 | Fish |
| 2005/0027182 A1 | 2/2005 | Siddiqui et al. |
| 2005/0027462 A1 | 2/2005 | Goode, Jr. et al. |
| 2005/0027463 A1 | 2/2005 | Goode, Jr. et al. |
| 2005/0033132 A1 | 2/2005 | Shults et al. |
| 2005/0038332 A1 | 2/2005 | Saidara et al. |
| 2005/0043598 A1 | 2/2005 | Goode, Jr. et al. |
| 2005/0051427 A1 | 3/2005 | Brauker et al. |
| 2005/0056552 A1 | 3/2005 | Simpson et al. |
| 2005/0090607 A1 | 4/2005 | Tapsak et al. |
| 2005/0097200 A1 | 5/2005 | Denning, Jr. et al. |
| 2005/0143671 A1 | 6/2005 | Hastings et al. |
| 2005/0148890 A1 | 7/2005 | Hastings |
| 2005/0151640 A1 | 7/2005 | Hastings |
| 2005/0154271 A1 | 7/2005 | Rasdal et al. |
| 2005/0165627 A1 | 7/2005 | Fotsch et al. |
| 2005/0176136 A1 | 8/2005 | Burd et al. |
| 2005/0182451 A1 | 8/2005 | Griffin et al. |
| 2005/0192557 A1 | 9/2005 | Brauker et al. |
| 2005/0193191 A1 | 9/2005 | Sturgis |
| 2005/0203360 A1 | 9/2005 | Brauker et al. |
| 2005/0207379 A1 | 9/2005 | Shen et al. |
| 2005/0245799 A1 | 11/2005 | Brauker et al. |
| 2005/0261062 A1 | 11/2005 | Lewin et al. |
| 2005/0261562 A1 | 11/2005 | Zhou et al. |
| 2005/0283198 A1 | 12/2005 | Haubrich et al. |
| 2005/0283208 A1 | 12/2005 | Von Arx et al. |
| 2006/0010098 A1 | 1/2006 | Goodnow et al. |
| 2006/0015020 A1 | 1/2006 | Neale et al. |
| 2006/0016700 A1 | 1/2006 | Brister et al. |
| 2006/0019613 A1 | 1/2006 | Lim |
| 2006/0020187 A1 | 1/2006 | Brister et al. |
| 2006/0020188 A1 | 1/2006 | Kamath et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036140 A1 | 2/2006 | Brister et al. |
| 2006/0036143 A1 | 2/2006 | Brister et al. |
| 2006/0036144 A1 | 2/2006 | Brister et al. |
| 2006/0040402 A1 | 2/2006 | Brauker et al. |
| 2006/0047538 A1 | 3/2006 | Condurso et al. |
| 2006/0068208 A1 | 3/2006 | Tapsak et al. |
| 2006/0071797 A1 | 4/2006 | Rosenfeld et al. |
| 2006/0089452 A1 | 4/2006 | Schneider et al. |
| 2006/0089542 A1 | 4/2006 | Sands |
| 2006/0142651 A1 | 6/2006 | Brister et al. |
| 2006/0155180 A1 | 7/2006 | Brister et al. |
| 2006/0168592 A1 | 7/2006 | Andrews et al. |
| 2006/0198864 A1 | 9/2006 | Shults et al. |
| 2006/0200020 A1 | 9/2006 | Brister et al. |
| 2006/0200022 A1 | 9/2006 | Brauker et al. |
| 2006/0200970 A1 | 9/2006 | Brister et al. |
| 2006/0204536 A1 | 9/2006 | Shults et al. |
| 2006/0222566 A1 | 10/2006 | Brauker et al. |
| 2006/0224108 A1 | 10/2006 | Brauker et al. |
| 2006/0235285 A1 | 10/2006 | Brister et al. |
| 2006/0246921 A1 | 11/2006 | Russ |
| 2006/0249381 A1 | 11/2006 | Petisce et al. |
| 2006/0252027 A1 | 11/2006 | Petisce et al. |
| 2006/0253012 A1 | 11/2006 | Petisce et al. |
| 2006/0257995 A1 | 11/2006 | Simpson et al. |
| 2006/0258761 A1 | 11/2006 | Boock et al. |
| 2006/0263763 A1 | 11/2006 | Simpson et al. |
| 2006/0270922 A1 | 11/2006 | Brauker et al. |
| 2006/0270923 A1 | 11/2006 | Brauker et al. |
| 2007/0016381 A1 | 1/2007 | Kamath et al. |
| 2007/0019213 A1 | 1/2007 | Vaidyanathan |
| 2007/0027370 A1 | 2/2007 | Brauker et al. |
| 2007/0027385 A1 | 2/2007 | Brister et al. |
| 2007/0032706 A1 | 2/2007 | Kamath et al. |
| 2007/0032718 A1 | 2/2007 | Shults et al. |
| 2007/0045902 A1 | 3/2007 | Brauker et al. |
| 2007/0059196 A1 | 3/2007 | Brister et al. |
| 2007/0060093 A1 | 3/2007 | Kerth et al. |

(56) References Cited

U.S. PATENT DOCUMENTS

| | | |
|---|---|---|
| 2007/0060132 A1 | 3/2007 | Wilhelmsson et al. |
| 2007/0066873 A1 | 3/2007 | Kamath et al. |
| 2007/0088223 A1 | 4/2007 | Mann et al. |
| 2007/0118187 A1 | 5/2007 | Denker et al. |
| 2007/0153993 A1 | 7/2007 | Cohen |
| 2007/0163880 A1 | 7/2007 | Woo et al. |
| 2007/0173709 A1 | 7/2007 | Petisce et al. |
| 2007/0173710 A1 | 7/2007 | Petisce et al. |
| 2007/0185390 A1 | 8/2007 | Perkins et al. |
| 2007/0192137 A1 | 8/2007 | Ombrellaro |
| 2007/0203966 A1 | 8/2007 | Brauker et al. |
| 2007/0208245 A1 | 9/2007 | Brauker et al. |
| 2007/0208246 A1 | 9/2007 | Brauker et al. |
| 2007/0231846 A1 | 10/2007 | Cosentino et al. |
| 2007/0232879 A1 | 10/2007 | Brister et al. |
| 2007/0242666 A1 | 10/2007 | Barrett |
| 2007/0253021 A1 | 11/2007 | Mehta et al. |
| 2007/0255116 A1 | 11/2007 | Mehta et al. |
| 2007/0293742 A1 | 12/2007 | Simonsen et al. |
| 2008/0015422 A1 | 1/2008 | Wessel |
| 2008/0030057 A1 | 2/2008 | Tai |
| 2008/0033254 A1 | 2/2008 | Kamath et al. |
| 2008/0034438 A1 | 2/2008 | Mireku |
| 2008/0045824 A1 | 2/2008 | Tapsak et al. |
| 2008/0083617 A1 | 4/2008 | Simpson et al. |
| 2008/0086044 A1 | 4/2008 | Brister et al. |
| 2008/0098038 A1 | 4/2008 | Motoyama |
| 2008/0108942 A1 | 5/2008 | Brister et al. |
| 2008/0119703 A1 | 5/2008 | Brister et al. |
| 2008/0119704 A1 | 5/2008 | Brister et al. |
| 2008/0119705 A1 * | 5/2008 | Patel .................... G16H 15/00 600/347 |
| 2008/0119706 A1 | 5/2008 | Brister et al. |
| 2008/0148148 A1 | 6/2008 | Ramanathan et al. |
| 2008/0172737 A1 | 7/2008 | Shen et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194938 A1 | 8/2008 | Brister et al. |
| 2008/0197024 A1 | 8/2008 | Simpson et al. |
| 2008/0199894 A1 | 8/2008 | Galasso |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0214915 A1 | 9/2008 | Brister et al. |
| 2008/0228054 A1 | 9/2008 | Shults et al. |
| 2008/0242961 A1 | 10/2008 | Brister et al. |
| 2008/0250482 A1 | 10/2008 | Ahtisaari |
| 2008/0262469 A1 | 10/2008 | Brister et al. |
| 2008/0263100 A1 | 10/2008 | Van Engelshoven et al. |
| 2008/0275313 A1 | 11/2008 | Brister et al. |
| 2008/0287765 A1 | 11/2008 | Rasdal et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0316015 A1 | 12/2008 | Naedele et al. |
| 2008/0319294 A1 | 12/2008 | Taub |
| 2008/0319295 A1 | 12/2008 | Bernstein et al. |
| 2008/0319296 A1 | 12/2008 | Bernstein et al. |
| 2009/0005703 A1 | 1/2009 | Fasciano |
| 2009/0018424 A1 | 1/2009 | Kamath et al. |
| 2009/0025063 A1 | 1/2009 | Thomas |
| 2009/0030294 A1 | 1/2009 | Petisce et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0045055 A1 | 2/2009 | Rhodes et al. |
| 2009/0054737 A1 | 2/2009 | Magar et al. |
| 2009/0062633 A1 | 3/2009 | Brauker et al. |
| 2009/0062635 A1 | 3/2009 | Brauker et al. |
| 2009/0076360 A1 | 3/2009 | Brister et al. |
| 2009/0085768 A1 | 4/2009 | Patel et al. |
| 2009/0097623 A1 | 4/2009 | Bharadwaj |
| 2009/0099436 A1 | 4/2009 | Brister et al. |
| 2009/0118596 A1 | 5/2009 | Khanuja et al. |
| 2009/0124877 A1 | 5/2009 | Goode, Jr. et al. |
| 2009/0124879 A1 | 5/2009 | Brister et al. |
| 2009/0124964 A1 | 5/2009 | Leach et al. |
| 2009/0131769 A1 | 5/2009 | Leach et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0147940 A1 | 6/2009 | Graves et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0171180 A1 | 7/2009 | Pering et al. |
| 2009/0178459 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192751 A1 | 7/2009 | Kamath et al. |
| 2009/0203973 A1 | 8/2009 | Donoghue et al. |
| 2009/0203981 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0270705 A1 | 10/2009 | Enegren et al. |
| 2009/0287074 A1 | 11/2009 | Shults et al. |
| 2009/0289507 A1 | 11/2009 | Shiu |
| 2009/0291634 A1 | 11/2009 | Saarisalo |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0026250 A1 | 2/2010 | Petty |
| 2010/0030484 A1 | 2/2010 | Brauker et al. |
| 2010/0030596 A1 | 2/2010 | Johari |
| 2010/0036215 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0082364 A1 | 4/2010 | Taub et al. |
| 2010/0087724 A1 | 4/2010 | Brauker et al. |
| 2010/0088387 A1 | 4/2010 | Calamera |
| 2010/0096259 A1 | 4/2010 | Zhang et al. |
| 2010/0121169 A1 | 5/2010 | Petisce et al. |
| 2010/0131294 A1 | 5/2010 | Venon et al. |
| 2010/0161269 A1 | 6/2010 | Kamath et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |

(56) References Cited

U.S. PATENT DOCUMENTS

| | | |
|---|---|---|
| 2010/0174167 A1 | 7/2010 | Kamath et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185075 A1 | 7/2010 | Brister et al. |
| 2010/0191075 A1 | 7/2010 | Angelides |
| 2010/0191082 A1 | 7/2010 | Brister et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0212583 A1 | 8/2010 | Brister et al. |
| 2010/0216507 A1 | 8/2010 | Maeda |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0249625 A1 | 9/2010 | Lin |
| 2010/0261987 A1 | 10/2010 | Kamath et al. |
| 2010/0265073 A1 | 10/2010 | Harper |
| 2010/0274107 A1 | 10/2010 | Boock et al. |
| 2010/0280341 A1 | 11/2010 | Boock et al. |
| 2010/0281409 A1 | 11/2010 | Rainisto et al. |
| 2010/0283917 A1 | 11/2010 | Ueno et al. |
| 2010/0286496 A1 | 11/2010 | Simpson et al. |
| 2010/0292556 A1 | 11/2010 | Golden |
| 2010/0298684 A1 | 11/2010 | Leach et al. |
| 2010/0305965 A1 | 12/2010 | Benjamin et al. |
| 2010/0313105 A1 | 12/2010 | Nekoomaram et al. |
| 2010/0323431 A1 | 12/2010 | Rutkowski et al. |
| 2010/0324403 A1 | 12/2010 | Brister et al. |
| 2010/0331644 A1 | 12/2010 | Neale et al. |
| 2010/0331656 A1 | 12/2010 | Mensinger et al. |
| 2010/0331657 A1 | 12/2010 | Mensinger et al. |
| 2011/0001605 A1 | 1/2011 | Kiani et al. |
| 2011/0004085 A1 | 1/2011 | Mensinger et al. |
| 2011/0009727 A1 | 1/2011 | Mensinger et al. |
| 2011/0016064 A1 | 1/2011 | Barton |
| 2011/0019824 A1 | 1/2011 | Sattiraju et al. |
| 2011/0022411 A1 | 1/2011 | Hjelm et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0046467 A1 | 2/2011 | Simpson et al. |
| 2011/0054282 A1 | 3/2011 | Nekoomaram et al. |
| 2011/0058485 A1 | 3/2011 | Sloan |
| 2011/0060530 A1 | 3/2011 | Fennell |
| 2011/0065384 A1 | 3/2011 | Cader et al. |
| 2011/0077490 A1 | 3/2011 | Simpson et al. |
| 2011/0081888 A1 | 4/2011 | Waniss |
| 2011/0105854 A1 | 5/2011 | Kiani et al. |
| 2011/0112908 A1 | 5/2011 | Rowley et al. |
| 2011/0118579 A1 | 5/2011 | Goode, Jr. et al. |
| 2011/0119080 A1 | 5/2011 | Hayter et al. |
| 2011/0124992 A1 | 5/2011 | Brauker et al. |
| 2011/0124996 A1 | 5/2011 | Reinke et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0144465 A1 | 6/2011 | Shults et al. |
| 2011/0149759 A1 | 6/2011 | Jollota |
| 2011/0152970 A1 | 6/2011 | Jollota et al. |
| 2011/0160544 A1 | 6/2011 | Hayter |
| 2011/0161111 A1 | 6/2011 | Dicks et al. |
| 2011/0178378 A1 | 7/2011 | Brister et al. |
| 2011/0184268 A1 | 7/2011 | Taub |
| 2011/0190614 A1 | 8/2011 | Brister et al. |
| 2011/0199214 A1 | 8/2011 | Gawlick |
| 2011/0201910 A1 | 8/2011 | Rasdal et al. |
| 2011/0201911 A1 | 8/2011 | Johnson et al. |
| 2011/0210830 A1 | 9/2011 | Talty et al. |
| 2011/0213225 A1 | 9/2011 | Bernstein et al. |
| 2011/0218414 A1 | 9/2011 | Kamath et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0234406 A1 | 9/2011 | Young et al. |
| 2011/0253533 A1 | 10/2011 | Shults et al. |
| 2011/0263958 A1 | 10/2011 | Brauker et al. |
| 2011/0264035 A1 | 10/2011 | Yodfat et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0287528 A1 | 11/2011 | Fern et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0320130 A1 | 12/2011 | Valdes et al. |
| 2012/0016305 A1 | 1/2012 | Jollota et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0075103 A1 | 3/2012 | Powell et al. |
| 2012/0078071 A1 | 3/2012 | Bohm et al. |
| 2012/0084053 A1 | 4/2012 | Yuen et al. |
| 2012/0108934 A1 | 5/2012 | Valdes et al. |
| 2012/0130214 A1 | 5/2012 | Brister et al. |
| 2012/0136221 A1* | 5/2012 | Killen .................. G16H 40/67 600/300 |
| 2012/0157127 A1 | 6/2012 | Ferren et al. |
| 2012/0172691 A1 | 7/2012 | Brauker et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0203467 A1 | 8/2012 | Kamath et al. |
| 2012/0209098 A1 | 8/2012 | Goode, Jr. et al. |
| 2012/0215086 A1 | 8/2012 | Kamath et al. |
| 2012/0215087 A1 | 8/2012 | Cobelli et al. |
| 2012/0215201 A1 | 8/2012 | Brauker et al. |
| 2012/0215461 A1 | 8/2012 | Goode, Jr. et al. |
| 2012/0215462 A1 | 8/2012 | Goode, Jr. et al. |
| 2012/0215496 A1 | 8/2012 | Kamath et al. |
| 2012/0216297 A1 | 8/2012 | Cohen et al. |
| 2012/0216507 A1 | 8/2012 | Nieuwstadt |
| 2012/0220266 A1 | 8/2012 | Lau et al. |
| 2012/0220979 A1 | 8/2012 | Brauker et al. |
| 2012/0226121 A1 | 9/2012 | Kamath et al. |
| 2012/0228134 A1 | 9/2012 | Simpson et al. |
| 2012/0233679 A1 | 9/2012 | Shedrinsky |
| 2012/0235823 A1 | 9/2012 | Trock et al. |
| 2012/0238851 A1 | 9/2012 | Kamen et al. |
| 2012/0238852 A1 | 9/2012 | Brauker et al. |
| 2012/0242501 A1 | 9/2012 | Tran et al. |
| 2012/0245447 A1 | 9/2012 | Karan et al. |
| 2012/0245448 A1 | 9/2012 | Shariati et al. |
| 2012/0245855 A1 | 9/2012 | Kamath et al. |
| 2012/0255875 A1 | 10/2012 | Vicente et al. |
| 2012/0258748 A1 | 10/2012 | San Vicente et al. |
| 2012/0259191 A1 | 10/2012 | Shariati et al. |
| 2012/0260323 A1 | 10/2012 | San Vicente et al. |
| 2012/0262298 A1 | 10/2012 | Bohm et al. |
| 2012/0265035 A1 | 10/2012 | Bohm et al. |
| 2012/0265036 A1 | 10/2012 | Estes et al. |
| 2012/0265037 A1 | 10/2012 | Bohm et al. |
| 2012/0277562 A1 | 11/2012 | Brister et al. |
| 2012/0277566 A1 | 11/2012 | Kamath et al. |
| 2012/0283541 A1 | 11/2012 | Kamath et al. |
| 2012/0283543 A1 | 11/2012 | Brauker et al. |

(56) References Cited

U.S. PATENT DOCUMENTS

| | | |
|---|---|---|
| 2012/0296311 A1 | 11/2012 | Brauker et al. |
| 2012/0296988 A1 | 11/2012 | Rao |
| 2012/0302854 A1 | 11/2012 | Kamath et al. |
| 2012/0302855 A1 | 11/2012 | Kamath et al. |
| 2012/0309302 A1 | 12/2012 | Buhot |
| 2012/0323100 A1 | 12/2012 | Kamath et al. |
| 2013/0012798 A1 | 1/2013 | Brister et al. |
| 2013/0030273 A1 | 1/2013 | Tapsak et al. |
| 2013/0030494 A1 | 1/2013 | Meredith et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0047233 A1 | 2/2013 | Fisk et al. |
| 2013/0053666 A1 | 2/2013 | Hughes et al. |
| 2013/0059541 A1 | 3/2013 | Sloan et al. |
| 2013/0116526 A1 | 5/2013 | Javitt et al. |
| 2013/0117696 A1* | 5/2013 | Robertson ............ G16H 20/10 715/763 |
| 2013/0117797 A1 | 5/2013 | Lam |
| 2013/0132416 A1 | 5/2013 | Hayter et al. |
| 2013/0136221 A1 | 5/2013 | Nishikata et al. |
| 2013/0137946 A1 | 5/2013 | Geske et al. |
| 2013/0151708 A1 | 6/2013 | Shelby et al. |
| 2013/0159456 A1 | 6/2013 | Daoud et al. |
| 2013/0172709 A1 | 7/2013 | Mears et al. |
| 2013/0173742 A1 | 7/2013 | Thomas et al. |
| 2013/0203351 A1 | 8/2013 | Hillan et al. |
| 2013/0276144 A1 | 10/2013 | Hansen |
| 2013/0285835 A1 | 10/2013 | Kim et al. |
| 2013/0321425 A1 | 12/2013 | Greene et al. |
| 2014/0088392 A1 | 3/2014 | Bernstein et al. |
| 2014/0104058 A1 | 4/2014 | Sheleheda et al. |
| 2014/0118104 A1 | 5/2014 | Sicurello et al. |
| 2014/0176346 A1 | 6/2014 | Brumback et al. |
| 2014/0184422 A1 | 7/2014 | Mensinger et al. |
| 2014/0184423 A1 | 7/2014 | Mensinger et al. |
| 2014/0187889 A1 | 7/2014 | Cohen et al. |
| 2014/0187890 A1 | 7/2014 | Mensinger et al. |
| 2014/0188398 A1 | 7/2014 | Cohen et al. |
| 2014/0207486 A1 | 7/2014 | Carty et al. |
| 2014/0235166 A1 | 8/2014 | Molettiere et al. |
| 2014/0244301 A1 | 8/2014 | Lee et al. |
| 2014/0266776 A1 | 9/2014 | Miller et al. |
| 2014/0288402 A1 | 9/2014 | Brister et al. |
| 2015/0032826 A1 | 1/2015 | Gunaratnam |
| 2015/0172096 A1 | 6/2015 | Sadovsky et al. |
| 2015/0195286 A1 | 7/2015 | Doppler et al. |
| 2015/0347711 A1 | 12/2015 | Soli et al. |
| 2015/0365818 A1 | 12/2015 | Mese et al. |
| 2015/0371350 A1 | 12/2015 | Zebarjadi et al. |
| 2015/0371516 A1 | 12/2015 | Petersen et al. |
| 2016/0066866 A1 | 3/2016 | Mensinger et al. |
| 2016/0066867 A1 | 3/2016 | Mensinger et al. |
| 2016/0066868 A1 | 3/2016 | Mensinger et al. |
| 2016/0073879 A1 | 3/2016 | Mensinger et al. |
| 2016/0073880 A1 | 3/2016 | Mensinger et al. |
| 2016/0081586 A1 | 3/2016 | Miller et al. |
| 2016/0239619 A1 | 8/2016 | Abou-Hawili et al. |
| 2017/0034649 A1 | 2/2017 | Dotan-Cohen et al. |
| 2017/0034682 A1 | 2/2017 | Matsumasa et al. |
| 2017/0135041 A1 | 5/2017 | Miller et al. |
| 2017/0181629 A1 | 6/2017 | Mahalingam et al. |
| 2017/0181630 A1 | 6/2017 | Mahalingam et al. |
| 2017/0181645 A1 | 6/2017 | Mahalingam et al. |
| 2017/0229006 A1 | 8/2017 | Tonna et al. |
| 2017/0231497 A1 | 8/2017 | Brister et al. |
| 2017/0293732 A1 | 10/2017 | Cohen et al. |
| 2017/0303785 A1 | 10/2017 | Mensinger et al. |
| 2018/0132720 A1 | 5/2018 | Miller et al. |
| 2018/0160949 A1 | 6/2018 | Brister et al. |
| 2019/0059730 A1 | 2/2019 | Brister et al. |
| 2019/0069817 A1 | 3/2019 | Brister et al. |
| 2019/0354674 A1 | 11/2019 | Berman et al. |
| 2019/0380163 A1 | 12/2019 | Miller et al. |
| 2020/0221949 A1 | 7/2020 | Mensinger et al. |
| 2020/0221950 A1 | 7/2020 | Mensinger et al. |
| 2021/0398663 A1 | 12/2021 | Reggiardo et al. |
| 2022/0013224 A1 | 1/2022 | Reggiardo et al. |
| 2022/0037007 A1 | 2/2022 | Nekoomaram et al. |

FOREIGN PATENT DOCUMENTS

| | | |
|---|---|---|
| CN | 1989733 A | 6/2007 |
| CN | 101278847 A | 10/2008 |
| CN | 201282481 Y | 7/2009 |
| CN | 101589393 A | 11/2009 |
| CN | 101601040 A | 12/2009 |
| CN | 101677770 A | 3/2010 |
| CN | 101742981 A | 6/2010 |
| CN | 101969836 A | 2/2011 |
| CN | 201732454 U | 2/2011 |
| CN | 102036718 A | 4/2011 |
| CN | 102065385 A | 5/2011 |
| CN | 102068310 A | 5/2011 |
| CN | 102724913 A | 10/2012 |
| EP | 2227062 A1 | 9/2010 |
| EP | 2453398 A1 | 5/2012 |
| EP | 2498196 A2 | 9/2012 |
| JP | 2000316819 A | 11/2000 |
| JP | 2004282541 A | 10/2004 |
| JP | 2005538794 A | 12/2005 |
| JP | 2006021031 A | 1/2006 |
| JP | 2006026270 A | 2/2006 |
| JP | 2006239084 A | 9/2006 |
| JP | 2006520657 A | 9/2006 |
| JP | 2008098744 A | 4/2008 |
| JP | 2008516303 A | 5/2008 |
| JP | 2008216057 A | 9/2008 |
| JP | 2011028765 A | 2/2011 |
| JP | 2016035699 A | 3/2016 |
| WO | 9718639 A1 | 5/1997 |
| WO | 03094074 A1 | 11/2003 |
| WO | 2004027676 A2 | 4/2004 |
| WO | 2004084720 A2 | 10/2004 |
| WO | 2005041131 A2 | 5/2005 |
| WO | 2006109072 A2 | 10/2006 |
| WO | 2008057951 A2 | 5/2008 |
| WO | 2008057952 A2 | 5/2008 |
| WO | 2008157701 A2 | 12/2008 |
| WO | 2010040092 A1 | 4/2010 |
| WO | 2011021118 A1 | 2/2011 |
| WO | 2011124993 A2 | 10/2011 |
| WO | 2012108935 A1 | 8/2012 |
| WO | 2012108936 A1 | 8/2012 |
| WO | 2012108939 A1 | 8/2012 |
| WO | 2012108940 A1 | 8/2012 |
| WO | 2013019225 A1 | 2/2013 |
| WO | 2014105631 A2 | 7/2014 |

OTHER PUBLICATIONS

Anonymous, "Near Field Communication—Wikipedia, The Free Encyclopedia," Retrieved from https://en.wikipedia.org/w/index.php?title=Near_field_communication&%20oldid=543740757, Jun. 27, 2014, 15 pages.

Dassau E., et al., "Enhanced 911/Global Position System Wizard: A Telemedicine Application for the Prevention of Severe Hypoglycemia—Monitor, Alert, and Locate," Journal of Diabetes, vol. 3(6), 2009, pp. 1501-1506.

Garg S., et al. "Improvement in Glycemic Excursions with a Transcutaneous, Real-Time Continuous Glucose Sensor A Randomized Controlled Trial," Diabetes Care, vol. 29(1), 2006, pp. 44-50.

Garg S.K., et al., "Improved Glucose Excursions Using an Implantable Real-Time Continuous Glucose Sensor in Adults With Type 1 Diabetes," Emerging Treatments and Technologies, Diabetes Care, vol. 27 (3), 2004, pp. 734-738.

Hirsch I. B., et al., "Should Minimal Blood Glucose Variability Become the Gold Standard of Glycemic Control?," Journal of Diabetes and Its Complications 19, 2005, pp. 178-181.

International Preliminary Report on Patentability for Application No. PCT/US2013/076544 dated Jul. 9, 2015, 12 pages.

(56) References Cited

OTHER PUBLICATIONS

International Preliminary Report on Patentability for Application No. PCT/US2014/016111 dated Sep. 24, 2015, 10 pages.
International Preliminary Report on Patentability for Application No. PCT/US2016/066399 dated Jul. 12, 2018, 14 pages.
International Search Report and Written Opinion for Application No. PCT/US2013/076544 dated Oct. 14, 2014, 16 pages.
International Search Report and Written Opinion for Application No. PCT/US2014/016111 dated Dec. 22, 2014, 13 pages.
International Search Report and Written Opinion for Application No. PCT/US2016/066399 dated Mar. 30, 2017, 15 pages.
Kovatchev, et al., "Algorithmic Evaluation of Metabolic Control and Risk of Severe Hypoglycemia in Type 1 and Type 2 Diabetes Using Self-Monitoring Blood Glucose Data," Diabetes Technology & Therapeutics, vol. 5(5), 2003, pp. 817-828.
Marling et al., "Characterizing Blood Glucose Variability Using New Metrics with Continuous Glucose Monitoring", Journal of Diabetes Science & Technology, vol. 5(4), Jul. 2011, 871-878.
Mirano Systems Inc, "Green Receipt," Retrieved from https://web.archive.org/web/20121224003730/http://mirano.ca/, 2012, 1 page.
NFC Forum, "NFC Data Exchange Format (NDEF)," NFCForum-TS-NDEF 1.0, Technical Specification, NFC Forum™, NDEF 1.0, Jul. 24, 2006, 25 pages.
NFCForum, "NFCForum-TS-DigitalProtocol-1.0, 2010," 194 pages.
Penckofer et al., "Does Glycemic Variability Impact Mood and Quality of Life?", Diabetes Technology & Therapeutics, 2012,vol. 14(4), pp. 303-310.
University of California, Diabetes Teaching Center "Blood Sugar & Stress", Diabetes Education Online Jul. 27, 2013, 3 pages.
Wikipedia, "Near-Field Communication," downloaded from https://en.wikipedia.org/wiki/Near-field_commucation on Jan. 3, 2019, pp. 1-14.
Wiley et al., "Automatic Detection of Excessive Glycemic Variability for Diabetes Management", 10th International Conference on Machine Learning and Applications, IEEE Computer Society, 2011, pp. 148-154.

* cited by examiner

REMOTE MONITORING OF ANALYTE MEASUREMENTS

INCORPORATION BY REFERENCE TO RELATED APPLICATIONS

This application is a continuation of U.S. patent application Ser. No. 17/396,502, filed Aug. 6, 2021, which is a continuation of U.S. patent application Ser. No. 17/133,339, filed Dec. 23, 2020, now U.S. Pat. No. 11,109,757, which is a continuation of U.S. patent application Ser. No. 16/934,987, filed Jul. 21, 2020, now U.S. Pat. No. 10,993,617, which is a continuation of U.S. patent application Ser. No. 16/831,648, filed Mar. 26, 2020, now U.S. Pat. No. 10,856,736, which is a continuation of U.S. patent application Ser. No. 16/591,439, filed Oct. 2, 2019, now abandoned, which is a continuation of U.S. patent application Ser. No. 14/945,263, filed Nov. 18, 2015, now U.S. Pat. No. 10,667,686, which is a continuation of U.S. patent application Ser. No. 13/842,679, filed Mar. 15, 2013, now U.S. Pat. No. 9,801,541, which claims the benefit of U.S. Provisional Application No. 61/747,717, filed Dec. 31, 2012. Each of the aforementioned applications is incorporated by reference herein in its entirety, and each is hereby expressly made a part of this specification.

FIELD

The present disclosure generally relates to remote monitoring.

BACKGROUND

Diabetes mellitus is a disorder in which the pancreas cannot create sufficient insulin, such as in the case of Type I diabetes and/or in which insulin is not effective, such as Type 2 diabetes. In a diabetic state, a victim suffers from high blood sugar, which causes an array of physiological derangements, such as kidney failure, skin ulcers, or bleeding into the vitreous of the eye, associated with the deterioration of small blood vessels. A hypoglycemic reaction, such as low blood sugar, may be induced by an inadvertent overdose of insulin, or after a normal dose of insulin or glucose-lowering agent accompanied by extraordinary exercise or insufficient food intake.

A diabetic person may carry a self-monitoring blood glucose (SMBG) monitor, which typically requires uncomfortable finger pricking methods. Due to the lack of comfort and convenience, a diabetic typically measures his or her glucose level only two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is higher or lower based on conventional methods.

Consequently, a variety of non-invasive, transdermal (e.g., transcutaneous) and/or implantable electrochemical sensors are being developed for continuously detecting and/or quantifying blood glucose values. These as well as other types of devices generally transmit raw or minimally processed data for subsequent analysis at a remote device, which can include a display, to allow presentation of information to a user hosting the sensor.

SUMMARY

Methods and apparatus, including computer program products, are provided for remote monitoring of analyte data. In some example implementations, there is provided a method. The method may include receiving, at a remote monitor, a notification message representative of an event detected, by a server, from analyte sensor data obtained from a receiver monitoring an analyte state of a host; presenting, at the remote monitor, the notification message to activate the remote monitor, wherein the remote monitor is configured by the server to receive the notification message to augment the receiver monitoring of the analyte state of the host; accessing, by the remote monitor, the server, in response to the presenting of the notification message; and receiving, in response to the accessing, information including at least the analyte sensor data.

In some example implementations, the above-noted aspects may further include additional features described herein including one or more of the following. The notification message may be received from at least a first wireless connection between the remote monitor and a notification service coupled to the server, wherein the additional information may be received from at least a second wireless connection between the remote monitor and the server. The first wireless connection may comprise a persistent, encrypted connection configured to carry a short message pushed by the notification service to a notification message center at the remote monitor, and wherein the second wireless connection may comprise a momentary, encrypted connection established, in response the accessing, to provide the additional information comprising at least additional analyte sensor data. The presenting may further comprise inhibiting access to one or more applications at the remote monitor until an action at the remote monitor is detected to indicate receipt of the notification message, wherein the remote monitor further may comprise a monitoring application. The notification message may be presented as a momentary message on a display at the remote monitor, without the inhibiting access. The at least one of the remote monitor and the receiver may comprise one or more of a mobile station, a wireless terminal, a tablet, a smart phone, a multi-mode wireless device, and a computer. The server may comprise at least one processor configured to receive analyte sensor data from the receiver, process the analyte sensor data to detect the event, and forward, when the event is detected, the notification message to the remote monitor based on one or more rules mapping the event to the remote monitor designated to receive the notification message for the detected event. The event may be detected based on a first set of rules at the server, wherein the first set of rules used to generate the notification message may be different from a second set of rules used to detect alerts sent to the receiver coupled to a sensor system at the host. The receiver may include, or couple to, a gateway interfacing a wireless connection to a public land mobile network and the server. A plurality of remote monitors may be configured, wherein at least one of the plurality of remote monitors may be designated as a primary monitor, and at least one of the plurality of remote monitors may be designated as a secondary monitor. The remote monitor may configure at least one rule representative of a trigger causing an alert to be sent by the server to the receiver. The remote monitor may configure one or more invitations sent to one or more devices to invite the one or more devices to monitor the receiver. The server may send a message acknowledging a receipt of the notification message. The notification message may include at least one of an indication of a need to calibrate a sensor and an acknowledgement message indicating at least one of an action or an acknowledgement sent by the receiver in response to an alarm sent to the receiver. The activation of the remote monitor may comprise opening the monitoring application. A connection may be established between the remote monitor and the server to enable the receiving of the information including the analyte sensor data. The server may register at least one of the remote monitor, the receiver, an analyte sensor coupled to the receiver, and the registration may include a code provided by a health care provider. The method may be implemented on an apparatus comprising at least one processor and at least one memory including code, which when executed by the at least one processor causes the apparatus to provide the method. A computer-readable storage medium may include code which when executed by at least one processor causes the method.

In another aspect, there is provided a method. The method may include receiving, at a remote monitor, an invitation to access a secure server and data associated with a receiver monitoring an analyte state of a host; and modifying, by the remote monitor, a rule defining an alert representative of an event associated with the analyte state of the host, wherein the alert, when triggered, causes a message to be sent to the remote monitor to notify the remote monitor of the event.

In some example implementations, the above-noted aspects may further include additional features described herein including one or more of the following. The modifying the rule may comprise varying a first threshold associated with a low level of glucose at the host, varying a second threshold associated with a high level of glucose at the host, varying a delay between when an associated alert is triggered by a receiver and a notification message is sent to the remote monitor, and/or varying a time value when a reminder notification is sent to the remote monitor. The method may be implemented on an apparatus comprising at least one processor and at least one memory including code, which when executed by the at least one processor causes the apparatus to provide the method. A computer-readable storage medium may include code which when executed by at least one processor causes the method.

It is to be understood that both the foregoing general description and the following detailed description are example and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

DETAILED DESCRIPTION

Figure 1:
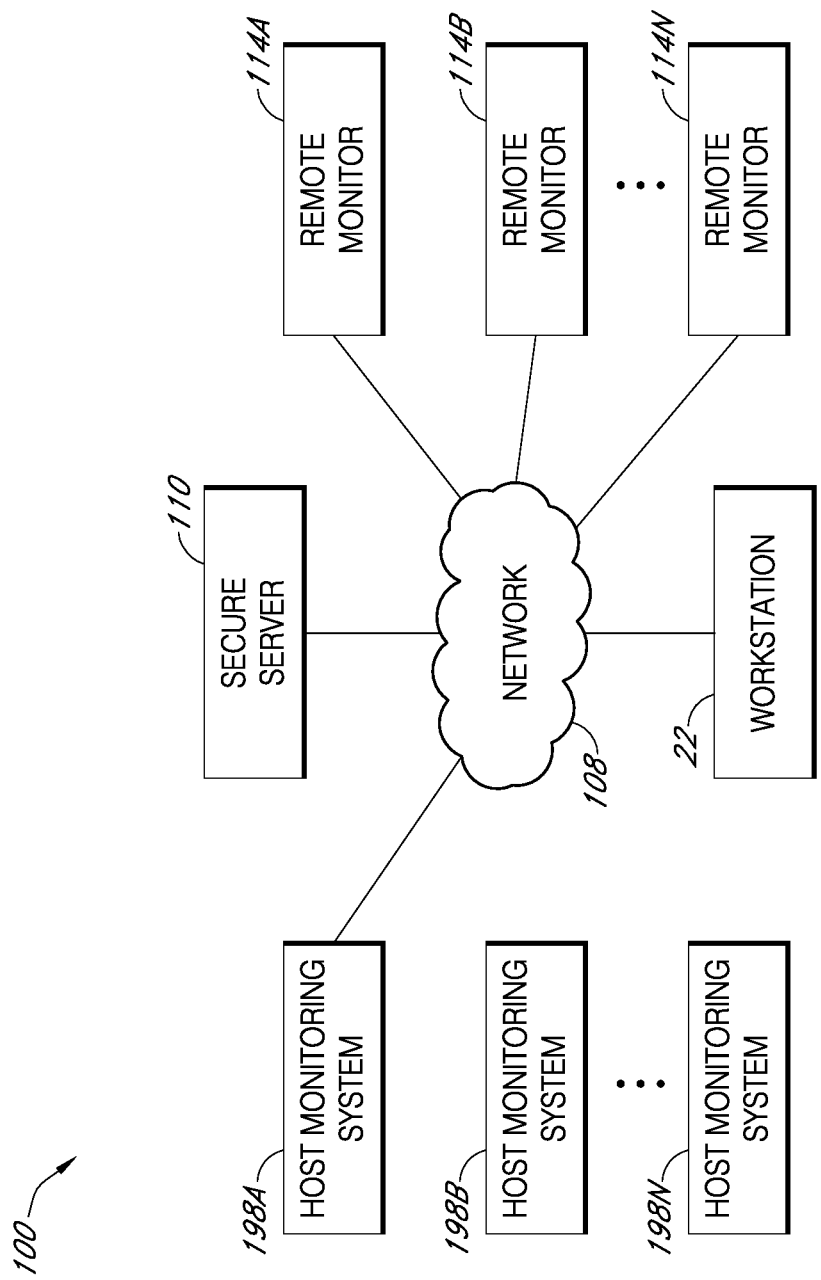
FIG. 1 depicts a high-level system architecture of a remote monitoring system in accordance with some exemplary implementations.

Implementations described herein can include a system for one or more caretakers (e.g., a parent, spouse or healthcare practitioner) to remotely monitor health characteristics of one or more hosts. The health characteristics can include an analyte concentration of a host, such as glucose, or a bodily function, such as heart rate, blood pressure, temperature and the like. In addition, other characteristics of a host can be monitored to facilitate care of a host, such as a location of the host, state of a host (e.g., exercising, sleeping, or working) and the like. The health characteristics and other characteristics can be gathered using a host monitoring system that incorporates a computing device, such as a smart phone, and one or more sensors, such a continuous glucose sensor, heart-rate monitor, GPS device, etc. Additionally, a host can manually input information into the computing device, such as meal information, medication administration times and amounts, and the like. The information gathered by the host monitoring system can then be transmitted to one or more remote monitors used by caretakers. The caretaker(s) can then receive information about the host's health condition using a remote monitoring system. In some implementations, a host monitoring system can transmit information directly to the one or more remote monitors and/or the host monitoring system transmits information first to a remote server, which then transmits information to the host monitor.

For purposes of illustration only, the following example is a non-limiting exemplary environment in which implementations of remote monitoring systems described herein can be used.

In this exemplary environment, a host having diabetes is monitored by several different caretakers. The host has a continuous glucose monitoring system, such as the DexCom G4® Platinum continuous glucose monitoring system, commercially available from DexCom, Inc., which provides measurements of the host's glucose levels on a display device, such as the DexCom G4® Platinum Receiver, also commercially available from DexCom, Inc.

Further, in this exemplary environment, the display device can be in communication with a gateway device, either wired communication or wireless communication. The gateway device gathers information, including real-time or near-real-time glucose concentration values, from the display device and transmits the information to a secure server. The gateway device can include a smartphone, such as an iPhone 4S or iPhone 5, each commercially available from Apple, Inc., and a host monitoring software application that comprises instructions configured to cause the smartphone to function as the gateway. The host monitoring software application can be in the form of a so-called "App" downloaded from the Apple App Store operated by Apple, Inc. The gateway can transmit information gathered from the continuous glucose monitoring system wirelessly to the secure server over a cellular network, Wi-Fi network, and the like.

The remote server can store and monitoring the information received from the remote monitoring system. The monitoring can include comparing glucose values of the host (generated by the continuous glucose monitoring system and transmitted to the server via the gateway) to predetermined thresholds and initiating an action if a threshold is exceeded. For example, the server can compare a current glucose value with a predetermined glucose threshold and initiate a notification, such as a text message over a cellular network, to a remote monitoring system if the glucose value exceeds the threshold. The server can also provide historical and current glucose values to the remote monitoring system on demand.

As discussed above, the remote monitor can be used by a caretaker to monitor health characteristics of a host, which in this exemplary environment is glucose concentration levels of the host. Similar to the host monitoring system, the remote monitoring system can be a smartphone, such as an iPhone 4S or iPhone 5, and a remote monitoring software application that comprises instructions configured to cause the smartphone to function as the remote monitoring system. The remote monitoring software application can be in the form of a so-called "App" downloaded from the Apple App Store operated by Apple, Inc. The remote monitoring system can receive notifications from the server when a threshold is exceeded, notifying the caretaker using the remote monitoring system of the condition of the host. The remote monitoring system can also be used to view historical information about the monitored glucose levels of the host and modify notification rules, such as the threshold levels that trigger notifications.

The following provides more detail of specific implementations, which may or may not include features noted in the above-discussed exemplary environment.

FIG. 1 depicts a high-level system architecture of an implementation of remote monitoring system 100. Here, remote monitoring system 100 includes a plurality of host monitoring systems 198A-198N connected to a plurality of remote monitors 114A-114M via network 118. Each host 198 monitoring system may be one or more health monitoring devices that gather health-related data associated with a host and transmit the health-related data via network 108. Exemplary implementations of health monitoring systems 198A-198N are described in more detail elsewhere in this disclosure, but in some implementations can include one or more sensors and computing devices operably coupled to the sensors to gather, process and transmit the health-related data. Network 108 can include any communication medium, such as wired and wireless networks including cellular networks, local area networks, wide area networks, Wi-Fi networks, the internet, and the like. Network 108 can also include one or more servers 110 to process the health-related data received from and transmit notifications and data to one or more remote monitors 114A-114M either automatically or in response to a request from the remote monitors. Each remote monitor 114A-114M can be associated with an individual or entity that is monitoring the health of one or more of hosts using host monitoring systems 198A-198N. Each remote monitor 114 can be associated with a caretaker, such as parent, spouse, doctor, nurse, hospital and the like. The remote monitor 114 can include a computing device that receives notifications from network 108 and requests additional information, such as historical health-related data generated by one or more host monitoring systems 198A-198N.

Remote monitoring system 100 of FIG. 1 can also include workstation 22. Workstation 22 may be a computing device, such as a personal computer, that has access to remote monitoring system 100 for configuring settings of system 100 and/or viewing information associated with one or more host monitoring systems 198, such as reports generated by remote monitoring system based on a host's health-related data.

Using remote monitoring system 100 of FIG. 1, one or more remote monitors 114A-11M can monitor one or more host monitoring systems 198A-198N. That is, host monitoring system 198A can be monitored by remote monitors 114A and 114B, and at the same time, remote monitor 114A can monitor host monitoring system 198B in addition to host monitoring system 198A. Various permissions and invitations can be used to limit which remote monitors 114A-114M can monitor host monitoring systems 198A-118N, as described in more detail later in this disclosure.

In one non-limiting example of remote monitoring system 100, each host monitoring system 198A-198N comprises a smartphone, such as an iPhone from Apple, Inc., and, likewise, each remote monitor 114A-114M has a smart mobile telephone, such as an iPhone. Each host mobile telephone has a host software application downloaded from a server of network 108, the application configuring the mobile telephone to perform any of the functions by host monitoring system 198 described herein, including gathering and transmitting health-related data used in remote monitoring system 100. The host software application can be an application downloaded using the App Store service hosted by Apple, Inc. Similarly, each remote monitor 114A-114M has a remote monitoring application downloaded from a server of network 108, the remote monitoring application configuring to perform any of the remote monitoring functions described herein, including receiving notifications and requesting health-related data of a host. The remote monitoring application can also be a software application downloaded using the App Store service hosted by Apple, Inc.

Figure 2A:
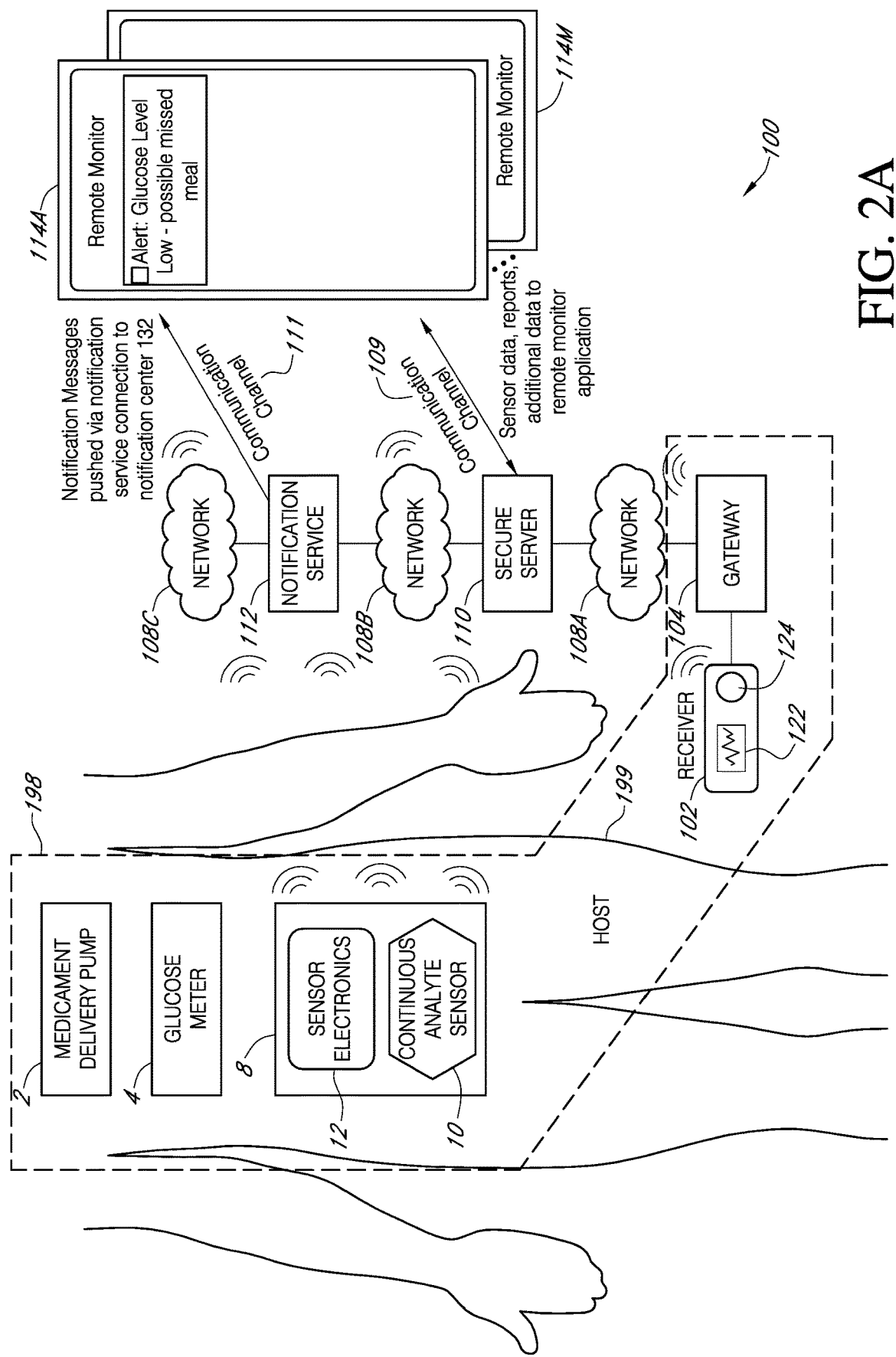
FIGS. 2A-2C illustrate different system architectures of the remote monitoring system of FIG. 1 in accordance with some exemplary implementations.

FIG. 2A depicts an example of system 100 for monitoring health-related information of host 199, in accordance with some example implementations. Here, the remote system 100 includes a continuous analyte monitoring system 8 including a sensor electronics module 12 and a continuous analyte sensor 10. The system 100 may also include devices and/or sensors, such as medicament delivery pump 2 (e.g., an insulin or glucagon pump), a glucose meter 4 (e.g., a blood finger stick meter), and any other device and/or sensor. The continuous analyte sensor 10 may be physically connected to sensor electronics module 12 and may be integral with (e.g., non-releasably attached to) or releasably attachable to the continuous analyte sensor 10.

The sensor electronics module 12, medicament delivery pump 2, a glucose meter 4, and/or other devices/sensors may couple via a wired or wireless links to one or more devices, such as a receiver 102. The receiver 102 may include a display 122 to enable the host 199 to present information from continuous analyte sensor 10, delivery pump 2, glucose meter 4, and/or other devices/sensors.

The implementation of system 100 illustrated in FIG. 2A provides via a gateway 104, networks 108A-C, a secure server 110, and a notification service 112, notification messages to one or more remote monitors 114A-114M, such as remote monitor 114A. Each remote monitor 114 may be configured at system 100 to provide a separate mechanism for monitoring the activity associated with host 199 including receiver 102, continuous analyte sensor 10, delivery pump 2, glucose meter 4, and/or any other sensor associated with host 199.

To illustrate by way of an example, host 199 may access receiver 102 to view data from, or control aspects of, continuous analyte sensor 10, delivery pump 2, and/or glucose meter 4. However, another entity, such as a parent, a care giver, a health care professional, a school nurse, and the like, may have remote monitor 114 receive notification messages representative of certain events determined based on sensor data from receiver 102, continuous analyte sensor 10, delivery pump 2, and/or glucose meter 4, and view historical and substantially real-time sensor data. For example, an event may comprise one or more of the following: a measured analyte sensor value above or below a predetermined threshold, a rate of change or a level of glucose measurements above a predetermined threshold, a predicted glucose value approaching (or predicted to approach) a predetermined threshold, a host 199 not responding to a prompt, a message, or an alert displayed at receiver 102, and/or any other event detected by secure server 110 and/or receiver 102. In the example of FIG. 2A, the remote monitor 114 depicts a notification message 132 indicating low glucose level of host 199. As such, an entity having remote monitor 114 may assist host 199 by providing an additional layer of monitoring and oversight of host 199, as well as receiver 102, continuous analyte sensor 10, delivery pump 2, glucose meter 4, and the like.

In some example implementations, the remote monitor 114 may include a processor, a computer-readable storage medium (e.g., memory, storage, and the like), a radio access mechanism (e.g., a modem and the like), and/or a user interface. The computer readable medium may include code which when executed by a processor provides one or more applications, operating systems, and the like. For example, an application may be configured as a remote monitoring application configured to monitor and/or control one or more of the receivers 102, the continuous analyte sensor 10, the delivery pump 2, the glucose meter 4, and the like. In some implementations, the remote monitor 114 is an iPhone mobile phone from Apple, Inc. and the application is an application downloaded over the Internet using the App Store service operated by Apple, Inc.

In some example implementations, the remote monitor 114 may comprise one or more of the following: a mobile station, a wireless terminal, a tablet, a smart phone, or the like. For example, the remote monitor 114 may be implemented as a wireless handheld device, a wireless plug-in accessory, or the like. Moreover, the remote monitor 114 may be implemented as multi-mode device configured to operate using a plurality of radio access technologies, such as Long Term Evolution (LTE), wireless local area network (WLAN) technology, such as 802.11 Wi-Fi and the like, Bluetooth, Bluetooth low energy (BT-LE), near field communications (NFC), and any other radio access technologies. Moreover, the remote monitor 114 may be configured to establish connections to access points in network 108A, such as cellular base stations, Wi-Fi access points, and the like, using at least one of the plurality of the radio access technologies. Although some of the examples herein refer to the remote monitor as a mobile, wireless device, the remote monitor may also be implemented as a stationary device, such as a personal computer and the like.

In some example implementations, the receiver 102 may be configured differently than the remote monitor 114. For example, the receiver 102 may include a different set of rules defining when an alert is sent to the receiver 102, when compared to the set of rules used to trigger a notification to the remote monitor 114. Moreover, although the receiver 102 may trigger alerts on its own (e.g. applying thresholds to sensor data received from sensor system 8), receive alerts from sensor system 8 or receive alerts directly from the secure server 110, the remote monitor 114 may be configured to receive messages, such as short messages, text messages, and the like, from a notification service 112, and these messages can serve to activate the remote monitor 114, such as activating the remote monitor application of the remote monitor. For example, the remote monitor 114 may close the remote monitor application session (as well as close network connection 109 to secure server 110), when the remote monitor application is not actively being used to conserve power at the remote monitor. When this is the case, the notification service 112 may send a message over network connection 111 to allow activation of the remote monitor 114 and/or a remote monitor application (and this activation may be automatic or under the control of a user of remote monitor 114).

Although some of the examples described herein refer to secure server 110 as an intermediary node between the receiver 102 and the remote monitor 114, in some example implementations, the secure server 110 may be by-passed. For example, the gateway 104 may communicate directly with the remote monitor 114, and vice-versa. In addition, the gateway 104 and receiver 102 may receive notification messages to activate an application at the receiver 102 or gateway 104 to allow the host to be alerted.

Figure 3:
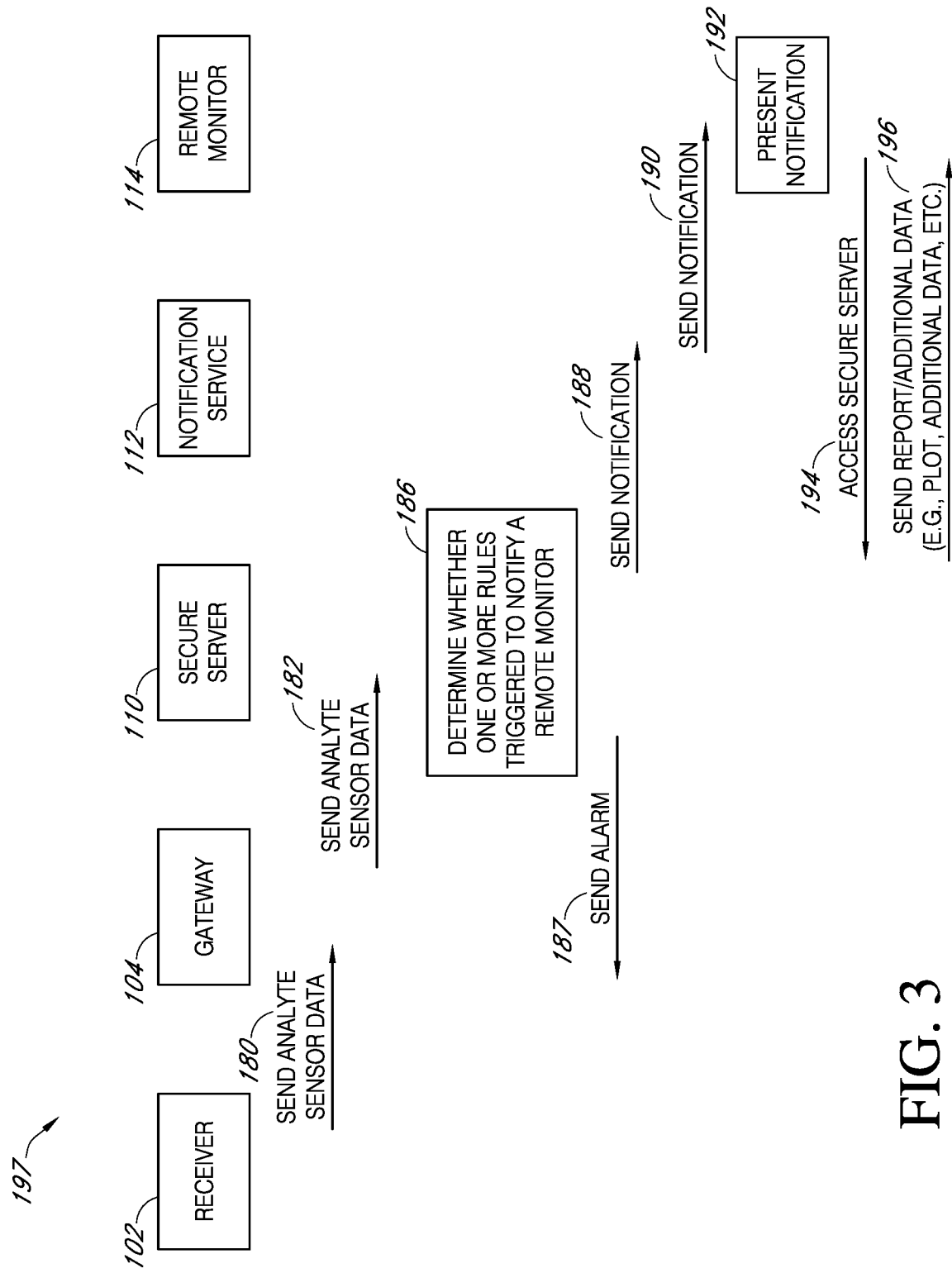
FIG. 3 depicts an example process for notifying a remote monitor of an event in accordance with some example implementations.

FIG. 3 depicts an example process 197 for notifying a remote monitor 114 of an event associated with receiver 102, continuous analyte sensor 10, delivery pump 2, glucose meter 4, and/or host 199, in accordance with some example implementations. The description of FIG. 3 also refers to FIG. 2A.

In some example implementations, the secure server 110 may register and/or configure one or more of the receiver 102, the continuous analyte sensor 10, the delivery pump 2, the glucose meter 4, and the host 199 before process 197 is initiated, although registration and/or configuration may occur at other times as well. The registration process may be performed to register the receiver 102, the continuous analyte sensor 10, the delivery pump 2, the glucose meter 4, the remote monitor 114, and/or the host 199 with the secure server 110. Moreover, the configuration process may be performed to configure system 100 including the identities of the one or more remote monitors used to monitor receiver 102, configure one or more rules used to trigger notification messages to the remote monitors, configure one or more rules designating primary and secondary remote monitors, configure one or more rules establishing schedules for the primary and secondary monitors, configure one or more rules defining an escalation sequence representative of when to elevate an event to a primary monitor or a secondary monitor, and the like.

At 180, receiver 102 may send sensor data, such as analyte data from sensor system 8 and the like, to gateway 104, which then forwards the sensor data at 182 to secure server 110. For example, receiver 102 may couple to gateway 104 via a wired or wireless connection, and gateway 104 may couple to secure server 110 via network 108A. The gateway 104 may be configured to pull current and/or historical data from the receiver 102 on its own or in response to a request from secure server 110.

At 186, the secure server 110 may determine whether one or more of the remote monitors 114A-114M, such as remote monitor 114A, should be sent a notification message regarding an event. The secure server 110 may determine whether to send a notification message to a remote monitor based on received sensor data (as well as any other data available at the secure server), which triggers an event (or satisfies a rule) at the secure server. For example, secure server 110 may receive the sensor data at 182 and then process the received sensor data alone or along with other data (e.g., historical data, data from other sources of patient information, and the like) to determine whether to send the notification message alerting the remote monitor 114 of the event. The secure server 110 may also receive information from other systems, such as a heath management system or a health care provider's systems, and this information may be used to trigger notification messages to the remote monitor. In addition, the secure server 110 may send notification messages to confirm whether the remote monitor is still actively monitoring the host 199.

To illustrate by way of an example, receiver 102 may receive sensor data from host 199 and transmit the sensor data to secure server 110 via gateway 104 and network 108A, and the secure server 110 may process the sensor data and determine a low level of glucose by comparing the most current glucose level data to a predetermined low glucose threshold, although other events described herein may be detected as well. The secure server 110 may include one or more rules defining events, such as the low level of glucose exceeding a threshold and include rules defining the identities of the remote monitors receiving a notification message indicating the low level of glucose at the host 199. For example, the rule may define that when a low level of glucose is detected for a certain host, a certain remote monitor should receive a notification message. The notification message may include an indication of the low level of glucose (e.g., the glucose value), the time of the event, and other information, such a plot of current and past glucose levels, host information (e.g., name), and/or any other host related information.

The one or more rules defining the events may be defined during the configuration process by a user, such as host 199, a caregiver, and/or predefined as default rules (which may be reconfigured by a user or may be adapted by the system 100 over time to accommodate the host). In some example implementations, the one or more rules may define a threshold value representative of a severity of the event that should be reported to the one or more remote monitors, the times of day when a notification message should be sent to each of the remote monitors, the identities (e.g., phone number, Internet Protocol address, email address, and the like) of the one or more remote monitors, and the like.

Furthermore, the one or more rules may include escalation rules, so that events can be handled differently based on severity of event, type of event, and/or lack of responsiveness by a designated remote monitor. For example, a rule may define that a glucose value below a certain value should not be the subject of a notification message to remote monitor 114 (although an alert message may be sent to the receiver 102 or gateway 104 to notify the host 199); another rule may define that a glucose value between a range of values should be the subject of a notification message to remote monitor 114; while another rule may define sending, when a dangerously low glucose value is detected, notification messages to remote monitor 114A as well as other remote monitors 114B-M. In some example implementations, the rules used to trigger alerts to host 199 at receiver 102 may be different from the rules used to send notification messages to remote monitor 114, although one or more of the rules may be the same as well.

Although the previous examples described an event associated with low glucose levels, other types of events may be defined as well at the secure server 110 in order to trigger notification messages to the remote monitor 114 and/or trigger alerts to the receiver 102.

At 187, the secure server 110 may send an alert to the receiver 102 and/or gateway 104. The alerts may be triggered based on events which are the same or different as the rules used to trigger events for notification messages to the remote monitor 114. Moreover, the secure server 110 may include a delay between when the alert is sent at 187 and the notification messages are sent at 188-190. For example, the delay may allow the receiver 102 to acknowledge or take action before sending messages at 188-190, as the receiver may also have a set of rules that are the same or different than those for the receiver stored on the secure server. That is, the receiver 102 may trigger an alert based on rules residing within the receiver, and the receiver may receive an alarm from the secure server based on a different set of rules stored at secure server. The delay prior to the secure server 110 sending a notification to the receiver 102 may be varied by the secure server based on the severity or type of event, and the delay may be configured by a user and/or configured programmatically. For example, a first delay may be used for a first low analyte threshold, but no delay may be used for a second, more severe, low glucose threshold.

At 188-190, a notification message may be sent to one or more remote monitors based on whether one or more rules are triggered at 186. In some example implementations, the secure server may send a notification message to a push notification service 112, which then pushes a notification to the remote monitor(s). Examples of push notification services include the Apple Push Notification Service (APNS) and Google Cloud Messaging, although any other messaging mechanism including email, short messaging service, tweets, and the like may be used as well. In the case of APNS, the remote monitor 114 (or a notification message center therein) may establish an Internet Protocol (IP) connection with the APNS. This connection may be encrypted, persistent, and/or accredited, so that the notification service can send notification messages to the notification message center even when the remote monitor application and/or remote monitor are not actively being used. For example, the notification message center may alert the user of the remote monitor 114 that a notification message had arrived for the remote monitor application.

In an implementation utilizing a push notification service, the notification service 112 may receive a notification message from secure server 110. The notification message may include a destination address, such as a phone number of the remote monitor 114, an IP address, and the like, and a payload, such as the contents of the notification message. Returning to the previous example regarding low glucose level, the notification message may include the phone number of remote monitor 114 and a short text message, such as a low glucose level value, time of measurement of the value, and/or an identity of the host. The notification message may be limited to 256 bytes, although other sized messages may be used as well. In any case, the notification service 112 pushes the notification message to remote monitor 114 via a connection, such as an Internet Protocol (IP) connection, between the notification service 112 and a notification message center at the remote monitor 114. When the notification message center at the remote monitor 114 receives the notification message, the notification message center may display the notification message, generate a sound, a vibration, and another other indication to a user of the remote monitor 114. And, in some example implementations, the notification message center or a user of the remote monitor may activate the remote monitoring application if the remote monitoring application at the remote monitor 114 is not actively being used. The notification service 112 may be used in implementations in which the remote monitor 114 resides on a device, such as a smart phone and the like, that places the remote monitor 114 or the applications therein in an idle or an inactive mode to conserve power or reduce signaling to/from the network.

In some example implementations, the push notification service may be by-passed, so that the secure server 110 sends the notification message directly to the remote monitor 114 and/or the remote monitoring application therein. This may occur, for example, when the remote monitoring application is open on the remote monitoring device.

When the notification message is received at 192, the remote monitor 114 or a remote monitoring application therein may be activated if in an idle mode or an inactive mode. Once activated (which can be programmatically or under the control of a user), the remote monitor 114 may attempt to establish a connection to secure server 110. For example, the remote monitoring application may not be actively being used (e.g., in an idle mode, sleep mode, off, in background mode, and the like). To activate the remote monitoring application, the remote monitoring application may be activated by, for example, opening the remote monitoring application by selecting and expanding the remote monitoring application, actively using the remote monitoring application by entering a value into, selecting an element of, the user interface of the remote monitoring application, and the like. Moreover, the remote monitor and/or remote monitoring application may be activated by other ways as well. For example, activation may be invoked by movement of the remote monitor detected by a motion sensor and/or turning on, or increasing, the intensity of the display at the remote monitor.

In response to acknowledgement that the remote monitor 114 has activated the remote monitoring application via access message 194, the secure server 110 may send at 196 additional information to the remote monitor. The content of the additional information sent from the secure server 110 to the remote monitor 114 may be automatically determined or may be defined by a request from remote monitor, which may be a request included in the access message 194 or a subsequent message from the remote monitor. The additional information may include one or more of the following: all available sensor data not currently stored in the receiver 102, sensor data over a predetermined amount of time, such as the previous 3 or 24 hours of glucose data obtained from the sensor system 100, receiver 102, and/or secure server 110, a plot of the glucose levels over time, a glucose variability value, instructions, motivational messages, status of host, remote monitoring permissions modified by the host, and the like.

In some implementations, the secure server automatically sends sensor data from the past three hours to the remote monitor and the remote monitor can request any additional amount of past sensor data should the remote monitor want to evaluate the host over a longer period of time. The secure server 110 may query the receiver 102 via gateway 104 for additional data in order to respond should the secure server not have all sensor data specified in a request from the remote monitor 114.

Figure 19:
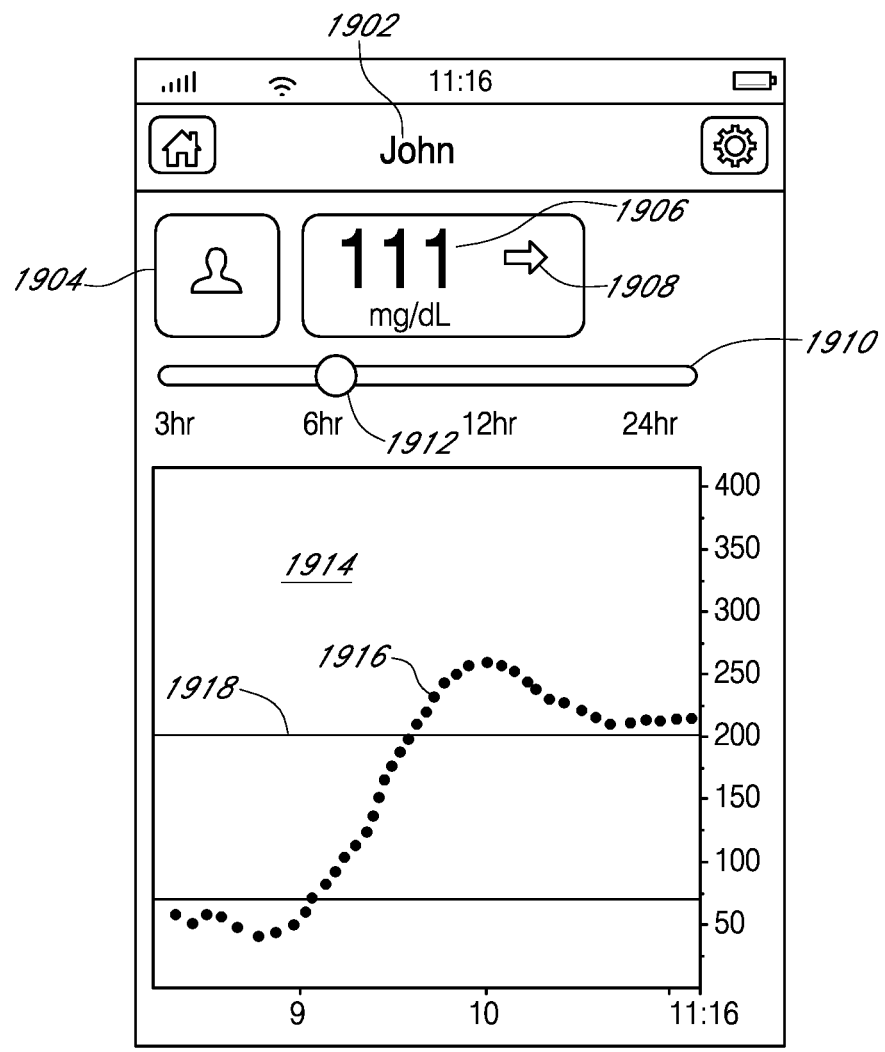
FIG. 19 is an exemplary page that provides a trend graph of a host's monitored analyte concentration in accordance with some implementations.

To illustrate further, when the remote monitor 114 receives the notification message, the notification may cause message 132 to appear on a display screen of the remote monitor 114. From the message 132, the remote monitoring application may be activated, either autonomously or under the direction of a user and/or notification message center. The remote monitoring application may then access at 192 the secure server 110 and programmatically receive any additional information associated with the event or other data since the last connection to secure server 110. For example, once the notification message is acknowledged with an access at 194 or an acknowledgement message, secure server 110 may automatically respond with a page having a trend graph of the current glucose state and information indicating the severity of the event (or any other information available at secure sensor 110). Although the secure server 100 may instead respond with a subset of the data, in which case, the secure server 110 may automatically respond with new data since the last connection to secure server 110, so that remote monitor can generate a page including the trend graph showing the last 3 hours' worth of glucose levels. In any case, the remote monitor may be configured to automatically present, when message 196 is received, the page showing relevant event information, such as a trend graph covering a predetermined time period (e.g., a three hour history of glucose levels) for the host. An exemplary page that can be automatically presented is illustrated in FIG. 19, which is discussed in more detail elsewhere in this disclosure.

Although FIG. 3 is primarily discussed with respect to remote monitor 114 monitoring a single host for ease of understanding, it is understood that the remote monitor may be monitoring multiple hosts, as discussed elsewhere herein. As such, secure server 110 may have sensor data and additional information associated with other hosts. Accordingly, in some implementations secure server can automatically send over sensor data of the other hosts remote monitor is monitoring, along with the sensor data from the host that triggered the notification 190 to the remote monitor. In this manner, remote monitor 114 can have an updated set of sensor data and other information associated with each of the hosts remote monitor is monitoring.

Figure 4A:
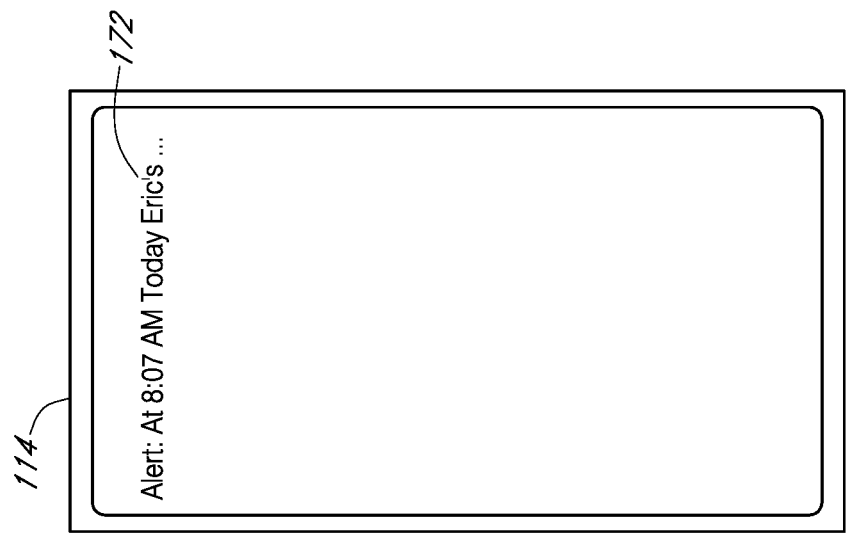
FIGS. 4A and 4B depict examples of notification messages, respectively, in accordance with some implementations.
Figure 4B:
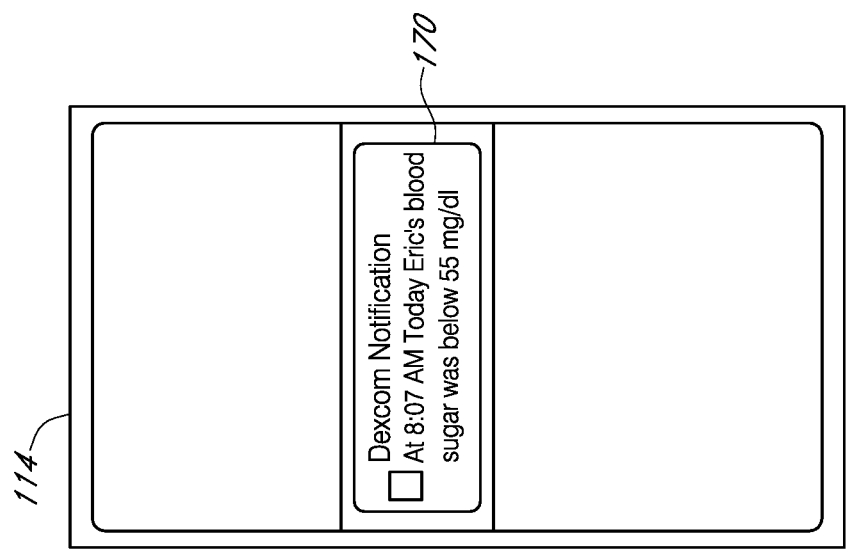

FIGS. 4A and 4B depict examples of notification messages 170 and 172, respectively. In the example of notification message 170, the notification message 170 may be presented at remote monitor 114 as a window requiring a user interaction, when the remote monitor 114 receives the notification message. For example, the user interaction may comprise pressing a button on remote monitor 114, touching the screen of remote monitor over the area associated with a portion of the message 170 or activating (e.g., executing, opening, and the like) the remote monitoring application at remote monitor 114. In some instances, the notification message 170 may appear when another application at remote monitor 114 is actively being used. When this is the case, a user interaction may comprise touching the screen over the area associated with a portion of the message 170 to acknowledge receipt of the notification message 170 before the user is allowed to resume the other application, although the user action may also preempt the other application and make the remote monitoring application the active application being viewed at the remote monitor. Moreover, the decision of whether to preempt the other application or resume the other application may be predetermined based on the severity level of the event, so that relatively more severe events preempt the other application, while less severe events do not.

In the example of notification message 172, the notification message 172 may be presented at remote monitor 114 as a message that appears in the user interface as an informational message not requiring intervention on the part of the user. Furthermore, when notification message 172 appears while another application is being used at remote monitor 114, notification message 172 does not require the user to acknowledge notification message 172, or even activation of the remote monitoring application (which may be idle or inactive state at remote monitor 114), resulting thus in the continued use of the other application by the user.

Figure 2B:
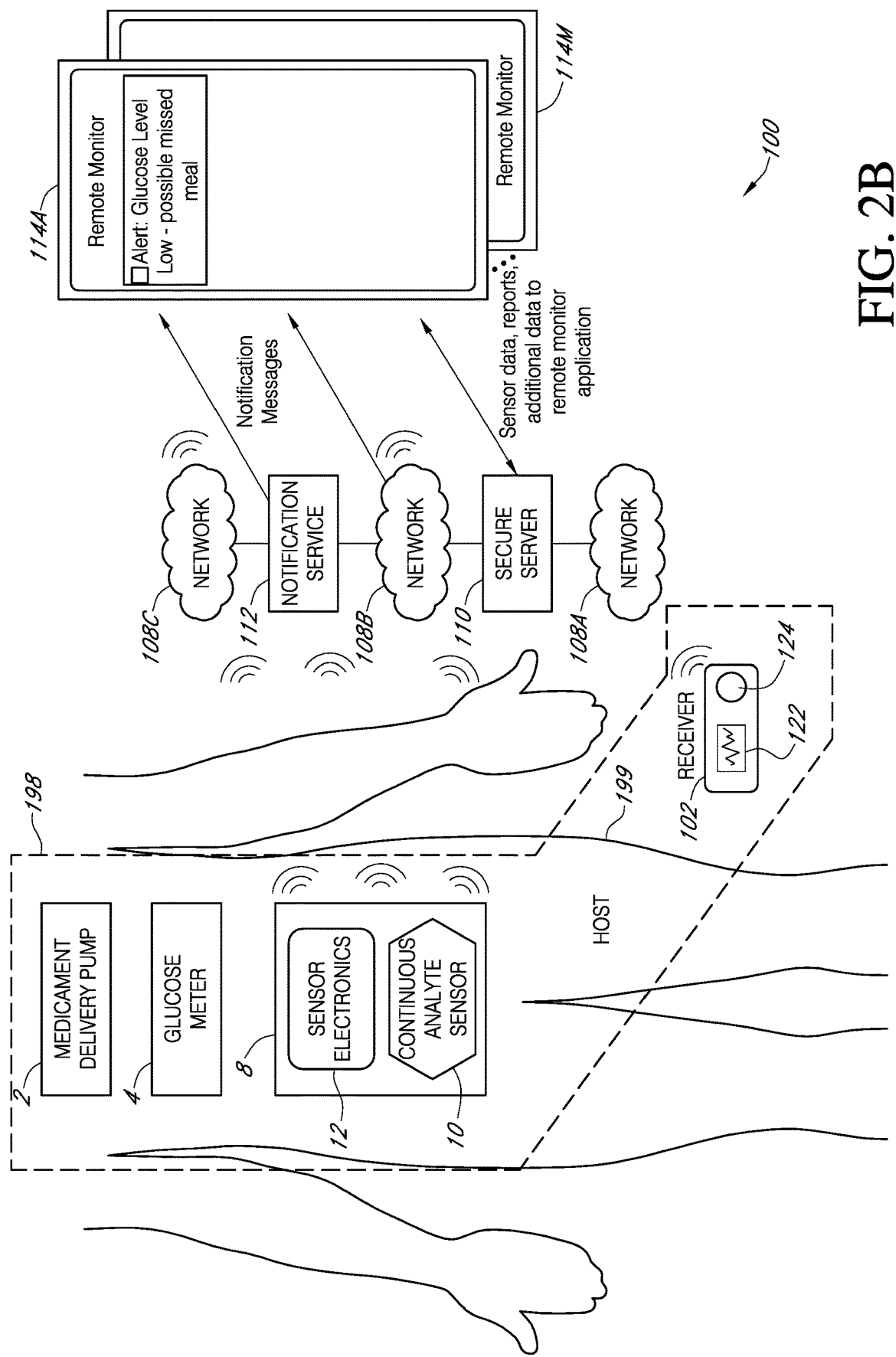

FIG. 2B depicts another example architecture of remote monitoring system 100. Referring to FIG. 2B, the receiver 102 may incorporate the gateway 104 of FIG. 2A. For example, the receiver 102 may include an interface, such as a radio frequency modem, to network 108A. To illustrate further, in the example of FIG. 2B, the receiver 102 may include a smart phone or other processor-based wireless device and provide access to network 108A and thus secure server 110 via the public land mobile network and other networks (e.g., the Internet).

In addition, while illustrated separately in FIG. 2B, the secure server 110 may incorporate the notification service 112 or by-pass the notification service 112 in some implementations. In such implementations, the operation of the system at FIG. 2B may be similar to the process described at FIG. 3 but sensor data 180 may be sent at 180 directly to secure server 110, and secure server 110 may send a notification message at 188 directly to the remote monitor 114.

Figure 2C:
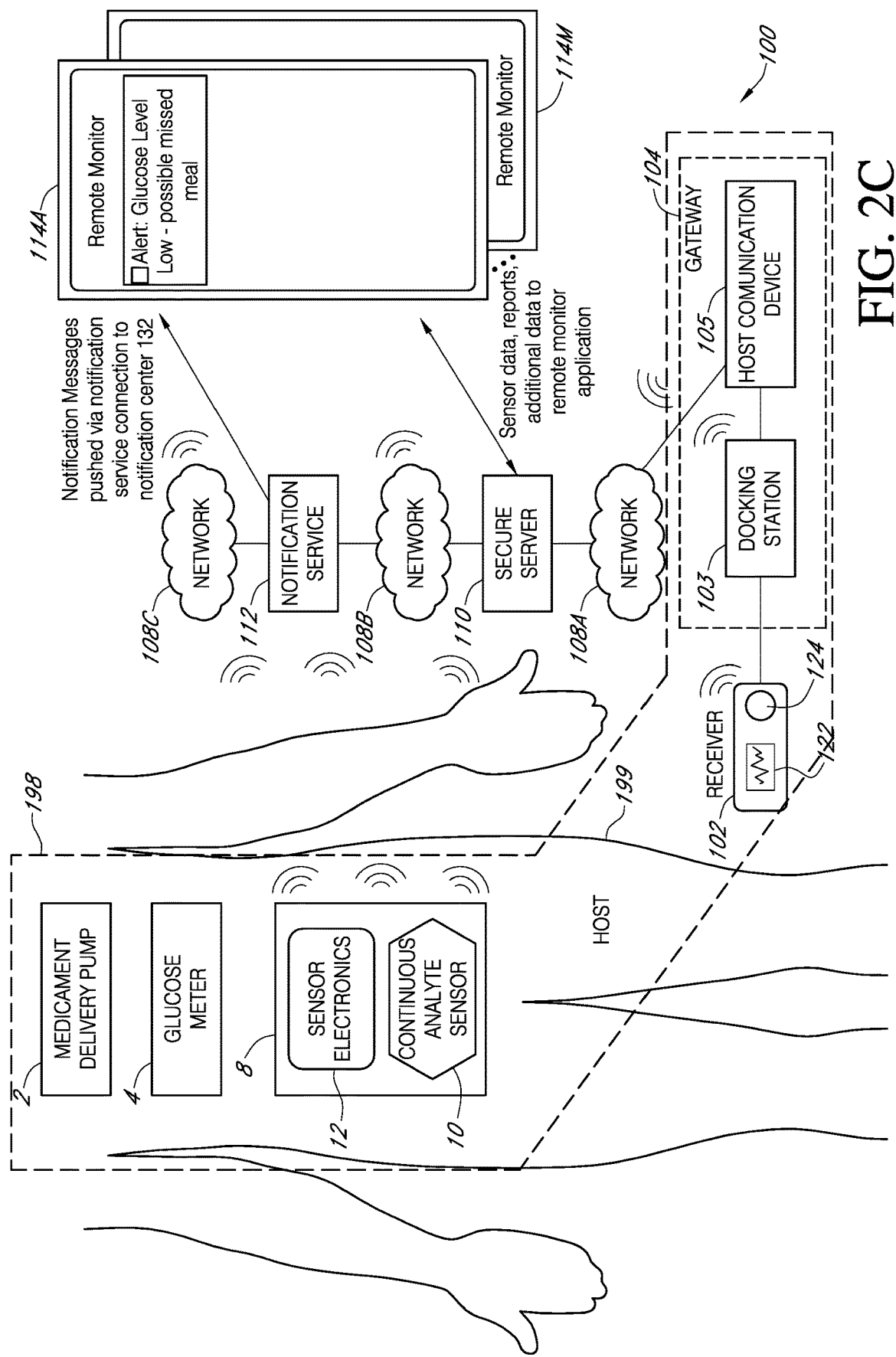

FIG. 2C depicts yet another example architecture of remote monitoring system 100. Here, gateway 104 is depicted as a dashed box including separate devices comprising a docking station 103 and a host communication device 105. Any of the functions for gateway 104 described herein can be divided between the docking station and host communication device in some implementations. For example, docking station 103 may communicate with receiver 102 and host communication device 105 may communicate with the secure server 110.

In some implementations, the host communication device 105 is a smart phone and the docking station 103 physically, electrically and communicatively couples to receiver 102 to hold, power and communicate with, respectively, the receiver. In one implementation, the docking station 103 couples to the receiver via a USB connection to both provide power to the receiver 102 and communicate with the receiver 102. The docking station 103 then communicates with host communication device 105 via wireless communication, e.g. using the BLE protocol, and the host communication device communicates to secure server 110 via network 108A. Such an implementation including the docking station 103 may be used in the case where receiver 102 and host communication device 105 do not have the capability to communicate directly with one another because, for example, the receiver and host communication device not use a compatible communication protocol.

In an example of the implementation of FIG. 2C, the host communication device 105 is a mobile telephone having a host monitoring application downloaded from the Apple App Store, wherein the application configures the mobile telephone to gather information from receiver 102 via docking station 103 and transmit that information to secure server 110, as well as any other functions described herein associated with gateway 104.

Before providing additional implementation examples for gateway 104, networks 108A-C, secure server 110, notification service 112, and remote monitor 114, the following provides implementation examples for the receiver 102, continuous analyte sensor 10, delivery pump 2, and/or glucose meter 4.

Referring again to FIGS. 2A-2C, sensor electronics module 12 may, in some example implementations, include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor. An example implementation of the sensor electronics module 12 is described further below with respect to FIG. 2.

The sensor electronics module 12 may, as noted, couple (e.g., wirelessly and the like) with one or more devices, such as receiver 102 and the like, presenting (and/or alerting) information, such as sensor information transmitted by the sensor electronics module 12 for display at receiver 102.

The receiver 102 may include one or more interfaces, such as machine-to-machine interfaces and user interfaces. For example, the user interfaces may include a variety of interfaces, such as one or more buttons 124, a liquid crystal display 122, a vibrator, an audio transducer (e.g., speaker), a backlight, and/or the like. The components that comprise the user interface may provide controls to interact with the user (e.g., the host). One or more buttons may allow, for example, toggle, menu selection, option selection, status selection, yes/no response to on-screen questions, a "turn off" function (e.g., for an alert), a "snooze" function (e.g., for an alert), a reset, and/or the like. The LCD 122 may provide the user with, for example, visual data output. The audio transducer 230 (e.g., speaker) may provide audible signals in response to triggering of certain alerts, such as present and/or predicted hyperglycemic and hypoglycemic conditions. In some example implementations, audible signals may be differentiated by tone, volume, duty cycle, pattern, duration, and/or the like. In some example implementations, the audible signal may be configured to be silenced (e.g., snoozed or turned off) by pressing one or more buttons 224 on the receiver 102 and/or by signaling the sensor electronics module using a button or selection on the receiver.

Although FIGS. 2A, and 2B depict example implementations of receiver 102 as a hand-held display device, other form factors may be used as well, such as a relatively small, key fob-like, dongle-like display device, a cellular phone (e.g., a smart phone, a tablet, and the like), a personal computer 20, and/or any other user equipment configured to at least present information (e.g., a medicament delivery information, discrete self-monitoring glucose readings, heart rate monitor, caloric intake monitor, and the like).

In some example implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a user, such as a host, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

Although the description herein refers to some implementations that include a continuous analyte sensor 10 comprising a glucose sensor, the continuous analyte sensor 10 may comprise other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used instead or as well including, for example, ketone bodies (e.g., acetone, acetoacetic acid and beta hydroxybutyric acid, lactate, etc.), glucagon, Acetyl Co A, triglycerides, fatty acids, intermediaries in the citric acid cycle, choline, insulin, cortisol, testosterone, and the like. In some implementations, other health characteristics of a host are monitored in addition to or instead of analyte monitoring described herein, including, but not limited to heart rate, blood pressure levels, blood oxygen levels, body temperature, caloric intake, medicament delivery and the like.

In one implementation, the sensor system 8 and receiver 102 comprise the DexCom G4® Platinum continuous glucose monitoring system available from DexCom, Inc., and gateway 104 comprises an Apple iPhone® smartphone available from Apple, Inc. with software downloaded thereon to cause the smart phone to perform the functions of gateway 104 described herein.

Figure 5:
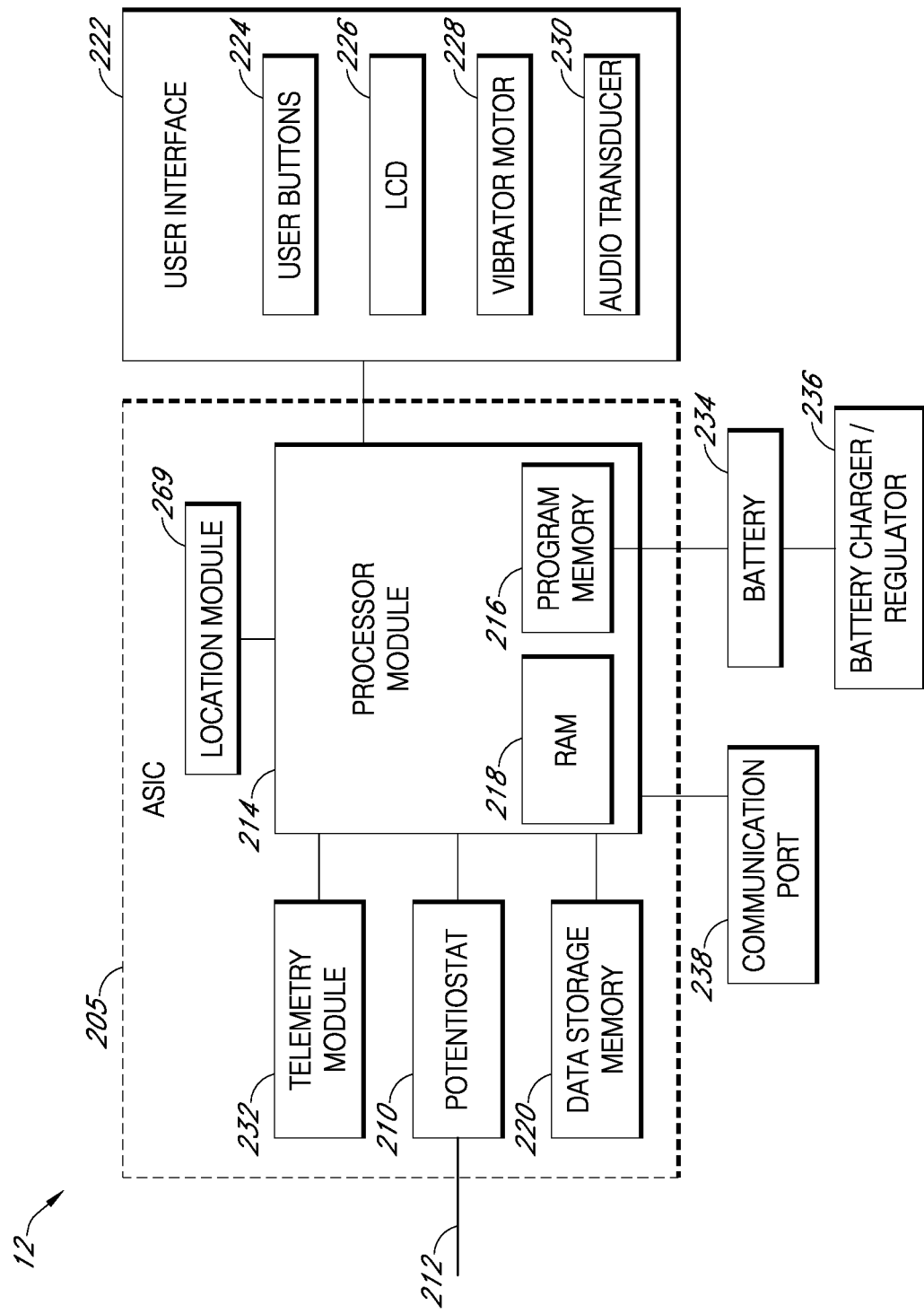
FIG. 5 depicts an example of a sensor electronics module in accordance with some example implementations.

FIG. 5 depicts an example of a sensor electronics module 12, in accordance with some example implementations. The sensor electronics module 12 may include sensor electronics that are configured to process sensor information, such as sensor data, and generate transformed sensor data and displayable sensor information. For example, the sensor electronics module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration information, sensor diagnostic information, location information (which may be provided by a location module 269 providing location information, such as global positioning/navigation system information), alarm/alert information, calibration information, smoothing and/or filtering algorithms of sensor data, and/or the like.

In some example implementations, the sensor electronics module 12 may be configured to calibrate the sensor data, and the data storage memory 220 may store the calibrated sensor data points as transformed sensor data. Moreover, the sensor electronics module 12 may be configured, in some example implementations, to receive wirelessly calibration information from a device, such as receiver 102, to enable calibration of the sensor data. Furthermore, the sensor electronics module 12 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms.

In some example implementations, the sensor electronics module 12 may comprise an application-specific integrated circuit (ASIC) 205 coupled to a user interface 122. The ASIC 205 may further include a potentiostat 210, a telemetry module 232 for transmitting data from the sensor electronics module 12 to one or more devices, such receiver 102 and the like, and/or other components for signal processing and data storage (e.g., processor module 214 and data store 220). Although FIG. 2 depicts ASIC 205, other types of circuitry may be used as well, including field programmable gate arrays (FPGA), one or more microprocessors configured to provide some (if not all of) the processing performed by the sensor electronics module 12, analog circuitry, digital circuitry, or a combination thereof.

In the example depicted at FIG. 5, the potentiostat 210 is coupled to a continuous analyte sensor 10, such as a glucose sensor, via data line 212 to receive sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels (and corresponding one or more data lines 212), depending on the number of working electrodes at the continuous analyte sensor 10.

In some example implementations, the potentiostat 210 may include a resistor that translates a current value from the sensor 10 into a voltage value, while in some example implementations, a current-to-frequency converter may also be configured to integrate continuously a measured current value from the sensor 10 using, for example, a charge-counting device. In some example implementations, an analog-to-digital converter may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics module 12 and one or more other devices, such as receiver 102, display devices, processors, network access devices/gateways, and the like. A variety of wireless radio technologies that can be implemented in the telemetry module 232 include Bluetooth, Bluetooth Low-Energy, the ANT protocol, NFC (near field communications), ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 comprises a Bluetooth chip, although the Bluetooth technology may also be implemented in a combination of the telemetry module 232 and the processor module 214. Further, while telemetry module is depicted as part of the ASIC 205 in FIG. 2, some or all of the telemetry module can be separate from the ASIC in other implementations.

The processor module 214 may control the processing performed by the sensor electronics module 12. For example, the processor module 214 may be configured to process data (e.g., counts), from the sensor, filter the data, calibrate the data, perform fail-safe checking, and/or the like.

In some example implementations, the processor module 214 may comprise a digital filter, such as for example an infinite impulse response (IIR) or a finite impulse response (FIR) filter. This digital filter may smooth a raw data stream received from sensor 10, data line 212 and potentiostat 210 (e.g., after the analog-to-digital conversion of the sensor data). Generally, digital filters are programmed to filter data sampled at a predetermined time interval (also referred to as a sample rate). In some example implementations, such as when the potentiostat 210 is configured to measure the analyte (e.g., glucose and the like) at discrete time intervals, these time intervals determine the sampling rate of the digital filter. In some example implementations, the potentiostat 210 is configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator configured to generate data packages for transmission to devices, such as receiver 102. Furthermore, the processor module 215 may generate data packets for transmission to these outside sources via telemetry module 232. In some example implementations, the data packages may, as noted, be customizable and/or may include any available data, such as a time stamp, displayable sensor information, transformed sensor data, an identifier code for the sensor and/or sensor electronics module, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics module 12 and/or charge the batteries 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, calibrate, perform fail-safe checking, and the like.

The memory 218 may also be used to store information. For example, the processor module 214 including memory 218 may be used as the system's cache memory, where temporary storage is provided for recent sensor data received from data line 212 and potentiostat 210. In some example implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of continuous analyte sensor data. For example, the data storage memory may store 1, 3, 4, 5, 6, 7, 8, 9, 10, 11, 12, 13, 14, 15, 20, and/or 30 (or more days) of continuous analyte sensor data received from sensor 10 via data line 212. The stored sensor information may include one or more of the following: a time stamp, raw sensor data (one or more raw analyte concentration values), calibrated data, filtered data, transformed sensor data, location information, and/or any other sensor related or displayable information.

The user interface 222 may include a variety of interfaces, such as one or more buttons 224, a liquid crystal display (LCD) 226, a vibrator 228, an audio transducer (e.g., speaker) 230, a backlight, and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alert), a "snooze" function (e.g., for an alert), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some example implementations, audible signals may be differentiated by tone, volume, duty cycle, pattern, duration, and/or the like. In some example implementations, the audible signal may be configured to be silenced (e.g., snoozed or turned off) by pressing one or more buttons 224 on the sensor electronics module and/or by signaling the sensor electronics module using a button or selection on a display device (e.g., key fob, cell phone, and/or the like).

Although audio and vibratory alerts are described with respect to FIG. 2, other alerting mechanisms may be used as well. For example, in some example implementations, a tactile alert is provided including a poking mechanism configured to "poke" the patient in response to one or more alert conditions.

The battery 234 may be operatively connected to the processor module 214 (and possibly other components of the sensor electronics module 12) and provide the necessary power for the sensor electronics module 12. In some example implementations, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some example implementations, the battery is rechargeable. In some example implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some example implementations, a battery regulator (or balancer) 236 regulates the recharging process by bleeding off excess charge current to allow all cells or batteries in the sensor electronics module to be fully charged without overcharging other cells or batteries. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a personal computer (PC) communication (com) port can be provided to enable communication with systems that are separate from, or integral with, the sensor electronics module. The communication port, for example, may comprise a serial (e.g., universal serial bus or "USB") communication port, to communicate with another computer system (e.g., PC, personal digital assistant or "PDA," server, or the like), a dongle with a wireless transceiver coupled to a docking station as described further below, and/or any other interface. The communication port may also be coupled to, or include, a wireless transceiver to allow wireless communications as well. In some example implementations, the sensor electronics module 12 is able to transmit historical data to a PC or other computing device (e.g., a secure server as disclosed herein) for retrospective analysis by a patient and/or physician.

In some continuous analyte sensor systems, an on-skin portion of the sensor electronics may be simplified to minimize complexity and/or size of on-skin electronics, for example, providing only raw, calibrated, and/or filtered data to a display device such as receiver 102 configured to run calibration and other algorithms described above with respect to the sensor electronics module 12. However, the sensor electronics module 12 may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 5, a variety of configurations may be used as well. For example, one or more memories may be used to provide storage space to support data processing and storage requirements at sensor electronic module 12.

Although some of the examples noted refer to a continuous analyte sensor 10, a glucose meter 4, and pump 2 in communications with sensor electronics module 12 and/or receiver 102, other devices may be used as well. For example, sensor electronics module 12 and/or receiver 102 may couple (either via wired and/or wireless links) to other sensors, including a glucose sensor, an altimeter, an accelerometer, a temperature sensor, a location module (e.g., a global positioning system processor or other source of location information), a heart rate monitor, a blood pressure monitor, a pulse oximeter, a caloric intake monitor, a medicament delivery device, and the like.

As noted above, the sensor electronics module 12 may generate and transmit, via a wireless or wired medium, a data package to a device, such as receiver 102, configured to receive, store, forward/retransmit, and/or display sensor data. The sensor electronics module 12 may, as noted, analyze the sensor data from the multiple sensors and determine which sensor data is to be transmitted based on one or more of many characteristics of the host, the receiver 102, a user of the receiver 102, a remote monitor 114, and/or characteristics of the sensor data. Moreover, one or more of the functions and/or components described herein with respect to the sensor system 8 may also or instead be found one or more of the receiver 102, gateway or secure server 110, and the one or more of the functions described herein with respect to the receiver 102 may also be found on the sensor system 8.

Referring again to FIG. 2A for purposes of illustration, the receiver 102 may forward analyte sensor data, as well as other available data, via wired and/or wireless links to gateway 104. In some example implementations, the gateway 104 may include a network interface configured as a radio interface, such as a cellular radio interface (e.g., Long Term Evolution and the like), a wireless local area network interface (e.g., Wi-Fi and the like), and/or any other type of wireless or wired interface. For example, the gateway 104 may include at least one processor including a radio frequency subsystem (e.g., a modem). In these wireless examples, when the receiver 102 couples to gateway 104, the gateway 104 sends analyte sensor data and the like wirelessly to secure server 110 via network 108A, which may include one or more of an access network, a wireless local area network, a radio access network, a cellular network, the Internet, and/or any other communication mechanism. In some example implementations, gateway 104 may also include a wired connection network 108A, which further couples to secure server 110.

Gateway 104 can automatically send sensor analyte data and additional information from receiver 102 in one or more of a plurality of ways. For example, receiver 102 can provide gateway 104 with information without a request from gateway. The information can be provided automatically, such as after the expiration of a timer or upon the generation of a new sensor data point, or can be responsive to user input to receiver 102. Gateway 104 can then automatically send the information from receiver to secure server 110. In another example, gateway can automatically request information based upon predetermined rules, such as after the expiration of a timer, such as a 5 minute timer. The information provided by the receiver 102 can then be automatically sent to secure server 110. In yet another example, gateway may send a request for information to gateway 104 which then forwards the request to receiver 102. The receiver 102 can then provide the requested information to gateway, which then forwards the information to secure server 110. In each of these examples, the information requested can be for specific information (e.g., a specific time period of sensor data) or simply a general request to send information. In the latter case, the receiver 102 can determine what information to send responsive to the request, such as any new sensor data generated by receiver since the receiver last provided information to the server 110.

Figure 6:
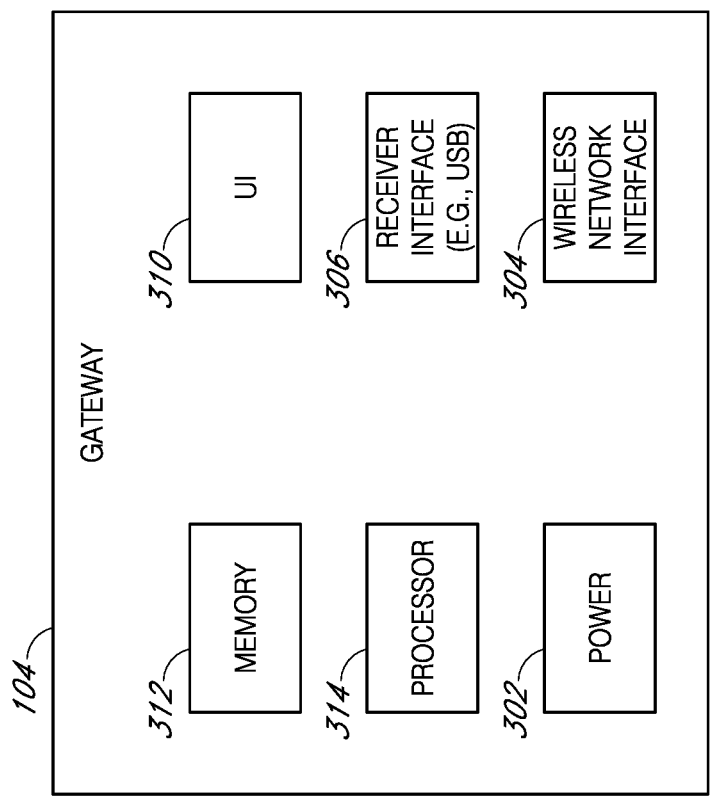
FIG. 6 is a block diagram of an implementation of a gateway in accordance with some implementations.

FIG. 6 is a block diagram of an implementation of gateway 104. The gateway 104 can include a power module 302 for charging the receiver 102 when it is coupled to the gateway 104, a wireless network interface 304 to allow wireless access to network 108A using a variety of network access technologies, although wired connectivity may also be provided by gateway 104 to network 108A, processor 414 and computer memory for storing instructions for processor 314 to execute functions of gateway 104 and storing health-related information received from receiver 102.

Moreover, the gateway 104 can include a receiver interface 306 to provide a wired and/or wireless interface to the receiver 102 in implementations where the receiver is separate from the gateway and the gateway does not include intermediate docking station 103. For example, receiver interface 306 may include a universal serial bus interface through which receiver 102 can communicate with gateway 104, secure server 110, and the like. The universal serial bus may also provide a physical connection for charging the receiver 102, although wireless charging may be used as well. Furthermore, receiver interface 306 may include a wireless interface, such as Bluetooth, Bluetooth low energy, Zig-bee, Atom, and any other wireless technology, through which receiver 102 can communicate with gateway 104, secure server 110, and the like. The gateway 104 may also include a user interface 310, such as a display, a touch screen display, a key pad, a speaker, a light emitting diode, and the like. For example, one or more light emitting diodes may be used to indicate whether the gateway 104 is properly coupled to the receiver 102, network 108A, secure server 110, and the like, whether the gateway 104 is connected to a power source (e.g., electrical outlet), whether the battery is charged, and the like. The display may also allow presentation of sensor data, alerts, notifications, and the like. For example, a user interface, such as a display, a light emitting diode, and the like, may provide an indication, such as a specific color light emitting diode, a message, and the like, representing that a connection, such as an Internet Protocol connection, a secure tunnel, and the like, has been establish between the gateway 104 and the secure server 110, so that the user of the gateway 104 recognizes that the receiver is coupled to the so-called "cloud" which includes the secure server 110.

As discussed above, in some implementations, gateway 104 can comprise a smart phone having a host monitoring application stored thereon that configures the smart phone to perform the functions of gateway 104 described herein.

Figure 7A:
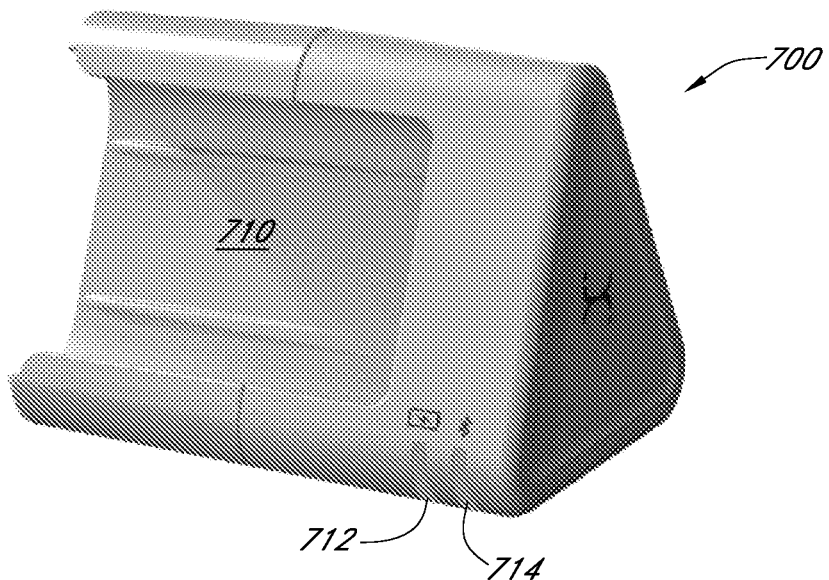
FIGS. 7A and 7B depict an example of a docking station in accordance with some implementations.
Figure 7B:

FIGS. 7A and 7B depict an example of the docking station 700, which can be the docking station 103 described with respect to of FIG. 2C. FIG. 7A illustrates a perspective view of the docking station 700 without receiver 102 physically coupled to the docking station, and FIG. 7B illustrates a front view of docking station with receiver 102 physically coupled to the docking station. Docking station 700 may have a cavity 710 to allow receiver 102 to be slidably inserted and releasably held into the docking station. The docking station 700 may also include a mechanical mechanism to releasably secure the receiver 102 to the docking station (not shown). The mechanism can be a latch assembly or the like. The docking station may electrically couple to the receiver 102 via, for example, an electrical connector, such as a universal serial bus connector, and/or a wireless interface, such as Bluetooth, Bluetooth low-energy, Wi-Fi, and any other wireless technology, and may transmit data received from the receiver 102 to host communication device 105, secure server 110 or remote monitor 114 using an electrical connector, and/or a wireless interface, such as Bluetooth, Bluetooth low-energy, Wi-Fi, and any other wireless technology.

The docking station 700 may also serve as a repeater and/or amplifier of any alert triggered by the receiver 102 and/or secure server 110. For example, the docking station 103 may receive an indication of an alert triggered by the receiver 102 from the receiver. The docking station 700 may repeat the alert by, for example, sounding an audible alarm, causing a vibration, and/or lighting a light emitting diode to indicate the alert to a user. Moreover, the receiver 102 may alert using a first alarm, such as a vibration, while the docking station 700 may re-alert using a second type of alarm that is different from the first alarm. For example, the first alarm can be a vibratory alarm and the second alarm can be an audible alarm or vice versa. As another example, the first alarm can be an audible alarm and the second alarm can also be an audible alarm, but the second audible alarm is louder than the first alarm and/or has a different tonal pattern.

In some implementations, the docking station 700 can trigger an alert by physically sensing an alarm from the receiver 102. For example, the docking station can include a vibratory and/or audible sensor that can sense vibrations or sounds, respectively, emanating from receiver 102. In this way, the docking station 103 can trigger an alert upon sensing the receiver 102 triggering an alarm while the receiver is docked in the docking station.

Furthermore, the alert settings at the docking station 700 may be the same or different as those at the receiver 102. For example, alert settings at docking station 700 may be more stringent than those at the receiver 102. For instance, the receiver 102 may have a low glucose threshold at a value that is greater than a corresponding low glucose threshold at the docking station 700. The alert settings of the docking station 700 can be user configurable using a user interface of the docking station or a user interface of the host communication device 105, for example.

Additionally or alternatively, in some implementations the docking station 700 delays triggering an alert that was triggered by receiver 102 to allow the host time to cure the alert prior to the docking station triggering an alarm. Should the host cure the alert prior to the expiration of the delay, then the docking station 700 does not trigger the alert.

Further to FIGS. 7A and 7B, the docking station 700 can include one or more light indicators, such as LEDs, that indicate a status of the docking station 700 and/or other components of the system 100. For example, a first light indicator 712 can indicate (by either turning on or changing color) if the docking station 700 is receiving power from an external power source, a second light indicator 714 can indicate (by turning on, changing color or blinking) if the docking station is paired to host communication device 105. Other light indicators can be used as well, such as a third light indicator that indicates if the communication channel between docking station 700 and host communication device 105 and/or secure server 110 is open and successfully transmitting sensor data from receiver 102.

Figure 8:
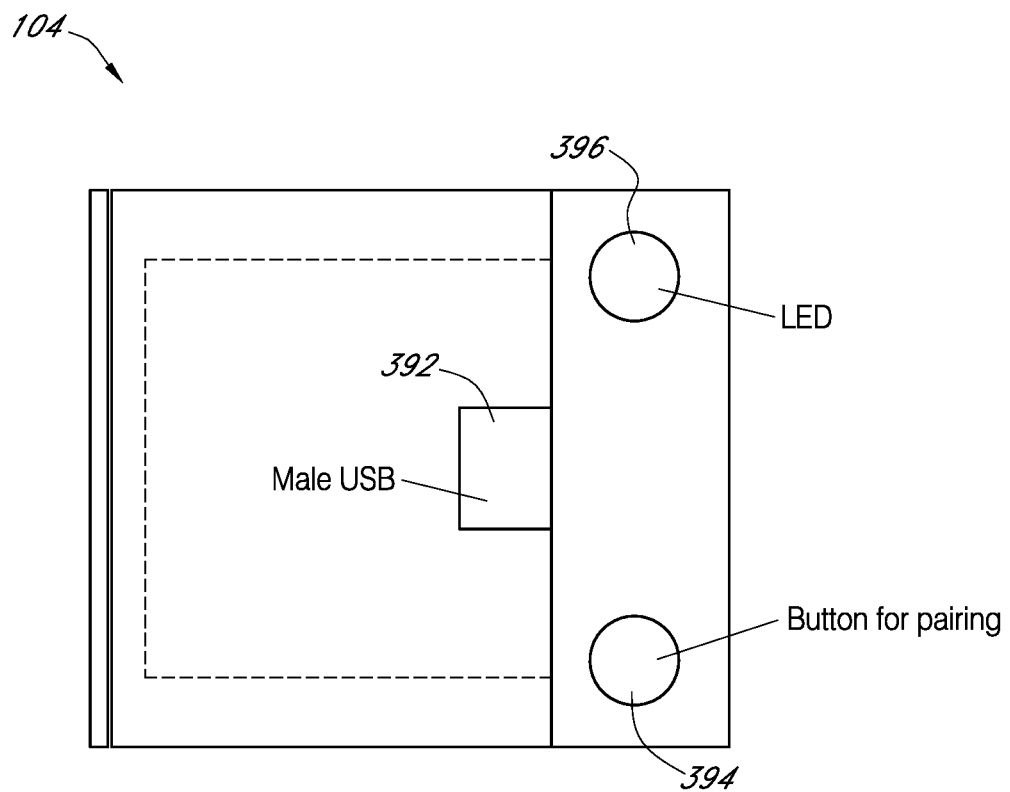
FIG. 8 depicts an implementation of a gateway or docking stations in accordance with some implementations.

FIG. 8 depicts another implementation of gateway 104. In the example of FIG. 8, the gateway 104 is configured as a dongle, such as a universal serial bus dongle, including universal serial bus connector 392 for coupling to the receiver 102, a user interface, such as a button 394 for performing a Bluetooth pairing to another device, such as host device 105, having access to network 108A, or directly to network 108A over a Wi-Fi or cellular communication channel. Although the gateway/dongle may be configured for Bluetooth pairing, the gateway/dongle may support connection establishment to the other devices using other radio access technologies, such as Bluetooth low energy, Wi-Fi, Atom, Zig-bee, NFC, and the like. The gateway/dongle depicted at FIG. 8 may also include a light emitting diode 396 for providing an indication of the state of the gateway 104 or receiver 102 (e.g., battery level, glucose level status, whether a user is in a low or high glycemic state, connection status to network, connection status to secure server, and the like). In some example implementations, the gateway at FIG. 8 may include its own rechargeable battery to power the gateway and/or the receiver 102, although it may rely on the receiver 102 as a power source as well.

In some example implementations, the gateway 104 may, as noted, include a radio frequency interface to allow the data to be automatically uploaded in a compressed format or uncompressed format from the receiver 102 to the secure server 110, which may be implemented as a so-called "cloud." And, the uploading may occur programmatically—without user intervention—when receiver 102 is in communication with gateway 104. The gateway 104 may also be configured to gather an identifier of the receiver 102 (or the receiver may automatically provide the identifier without a request for the identifier from the gateway 104) and provide the identifier to the secure server 110 to allow the secure server 110 to associate the received sensor data with the host 199, receiver, and any previously provided sensor data stored at secure server 110 (or a repository coupled to secure server 110) associated with the host. In some implementations, the identifier is the serial number of the receiver 102, and the receiver automatically sends the identifier along with any sensor data the receiver provides to gateway. Moreover, in some example implementations, the gateway 104 may be configured to send data incrementally, i.e., data previously received would not be re-sent to secure server 110 unless requested by secure server 110. Furthermore, gateway 104 may select between a cellular connection and a Wi-Fi connection based on connection speed, cost, and the like. For example, a free Wi-Fi connection may be selected over a fee-based cellular connection if available. Further, a cellular connection may be used for sending substantially real-time data generated by sensor system 8, but a Wi-Fi connection used for sending historical data, as it may not be as important for sending historical data in a timely fashion in some implementations.

In some example implementations, the gateway 104, receiver 102, sensor system 8, and remote monitor 114 may be preconfigured, so that when the sensor system 8 and receiver 102 communicatively couple to gateway 104, the gateway 104 recognizes the sensor system/receiver and/or users thereof. Further, the remote monitor 114 may also be recognized by server 110 to allow remote monitoring of receiver 102 to occur with little (if any) configuration by an end-user/host of receiver 102. For example, the secure server 110, gateway 104, receiver 102, sensor system 8, and remote monitor 114 may be preconfigured and preregistered, with little, if any, configuration or registration effort on the part of the host.

Referring again to FIGS. 2A-2C, the network 108A may include a wireless access network, such as a cellular network, a wireless local area network, and the like. In addition, network 108A may couple to other networks as well. For example, the gateway 104 may couple to an access network served by a base station or a Wi-Fi access point, which may have backhaul links to other networks including the public land mobile network, the Internet, and the like. Networks 108B-C may be implemented in a manner that is the same or similar to network 108A.

The secure server 110 may receive analyte sensor data, store analyte sensor data, process analyte sensor data to detect events and thus allow generation of notifications to remote monitors 114 and/or generation of alerts to receiver 102 and/or gateway 104, generate pages or reports for display at remote monitor 114, receiver 102 and/or gateway 104, allow registration and/or configuration of host 199, sensor system 8, receiver 102, gateway 104 and remote monitor 114.

In some example implementations, one or more entities may have remote monitors 114A-114M. For example, the secure server 110 may register the identity of the users of remote monitors 114A-114M and a schedule for when each entity performs monitoring. Moreover, one or more of the entities may be configured at the secure server 110 as primary monitors for receiving notifications, while other entities may be configured as backup, secondary monitors for receiving notifications when a primary monitor does not acknowledge, or act on the, notification message sent to a remote monitor 114 according to one or more predefined rules. Furthermore, the secure server 110 may include one or more rules defining when an event results in a notification to one or more of the remote monitor(s) 114.

The secure server 110 may also provide a cloud-based diabetes data management framework that receives patient-related data from various devices, such as a medical device, a glucose meter, a continuous glucose monitor, a sensor system, a receiver, and/or other devices (e.g., a device providing food consumption, such as carbohydrates, consumed by a host or patient, medicament delivery data, time of day, temperature sensors, exercise/activity sensors, and the like) including any device disclosed herein. Furthermore, the cloud-based diabetes data management system may receive data programmatically with little (or no) intervention on the part of a user. The data received from devices, receivers, source systems, and the like may be in a variety of formats and may be structured or unstructured. For example, the secure server 110 may receive, from sensor system 8 and receiver 102, raw sensor data, which has been minimally processed or analyzed, and the received data is then formatted, processed (e.g., analyzed), and/or stored in order to enable report generation by secure server 110. In addition to sensor data, the secure server 110 may also receive data from source systems, such as health care management systems, patient management systems, prescription management systems, electronic medical record systems, personal health record systems, and the like.

In some example implementations, the secure server 110 may check received data for transmission-related errors, data formatting, device-related error codes, validity of the data, duplicate data points, and/or other aspects of the data. Moreover, if out-of-range data points or device errors are found, the secure server 110 may identify those data points by, for example, flagging those data points, subsequently correcting the identified data points programmatically or by a system administrator, and storing the corrected data points. Moreover, secure server 110 may be configured by a user, such as a clinician, doctor, and the like, to perform additional data processing steps, such as correcting time of day, correcting the date, and analyzing data by specific cohorts, groups, and relationships (e.g., demographics, such as age, city, state, gender, ethnicity, Type I diabetes, Type II diabetes, age of diabetes diagnosis, lab results, prescription drugs being used, self-reported conditions of the patient, diagnosed conditions of the patient, responses to questions posed to patient, and any other metadata representative of the host/patient). Once secure server 110 performs initial data processing (e.g., checks, cleaning, and analysis), the processed data and/or the raw data may be stored at a repository coupled to the secure server 110.

The processing at secure server 110 may also include associating metadata with the data received from the devices and/or sensors. Examples of metadata include patient information, keys used to encrypt the data, patient accelerometer data, location data (e.g., location of patient or location of patient's clinic), time of day, date, type of device used to generate associated sensor data, and the like. The patient information can include the patient's age, weight, sex, home address and/or any past health-related information, such as whether the patient has been diagnosed as a Type 1 or Type 2 diabetic, high-blood pressure, or as having any other health condition.

The processing may also include one or more of the following: analysis, such as determining one or more descriptive measurements; detecting or predicting events (e.g., a hypoglycemic, a hyperglycemic, and/or any other feature detected in the sensor data); applying pattern detectors to the received sensor data; and generating reports based on received information, such as sensor data, and descriptive measurements of the information including sensor data. The descriptive measurements may include statistics (e.g., median, inner, and outer quartile ranges, mean, sum, n, standard deviation, and coefficients of variation). In some example implementations, secure server 110 may also associate metadata with the data received from the devices, sensors, source system, and/or receivers; determine one or more descriptive measurements, such as statistics (e.g., median, inner and outer quartile ranges, mean, sum, n, and standard deviation); generate reports including descriptive measurements; validating and verifying the integrity of the received data from the devices, sensors, source system, and/or receivers; processing received data based on metadata (e.g., to select certain patients, devices, conditions, diabetic type, and the like), and/or correlating received data from the devices, sensors, source system, and/or receiver, so that the data can be compared and combined for processing including analysis. Moreover, the results of any processing performed by secure server 110 may be used to generate one or more reports, such as graphs, bar graphs, static charts, charts, and the like. Furthermore, the reports and other outputs generated secure server 110 may be provided to receiver 102, remote monitor 114, and any other processor via one or more delivery mechanisms.

Secure server 110 may be considered secure in the sense that it keeps private, patient identifiable information and/or restricts access to users registered and thus authorized to use secure server 110. For example, secure server 110 may receive a request from a device, such as receiver 102 or remote monitor 114, to perform an action (e.g., provide data, store data, analyze/process data, request a report, request configuration information, request registration, and the like). Before secure server 110 services the request, the secure server 110 may process the request to determine whether the request is authorized and authenticated. For example, an authenticator and authorizer may determine whether the sender of the request is authorized by requiring a user to provide a security credential (e.g., a user identifier, a password, a stored security token, and/or a verification identifier provided by text message, phone, or email) at a user interface presented on a processor, such as receiver 102, remote monitor 114, and/or any other computer. If authorized, authenticator and authorizer may authenticate the sender of the request to check whether a security credential associated with sender of the request indicates that the sender is indeed permitted to access a specific resource at system 100 in order to perform the action, such as store (or upload) data at a repository, perform analyze/process data, request report generation, receive alerts, receive notification messages, and the like.

In some example implementations, the secure server 100 may include a pattern detector to perform pattern detection on data, such as sensor data representative of blood glucose data, analytes, and other data as well (e.g., insulin pump data, carbohydrate consumption data, and the like). The pattern detector may detect the pattern and generate an output, which may be provided to a report generator at secure server for generating an alert to receiver 102, a notification message to remote monitor 114, and/or a page containing a report.

Moreover, the pattern detector may detect patterns in data/sensor data retrospectively for a predetermined time defined by system 100 and/or a user. For example, the pattern detector may receive input data from a repository coupled to secure server 110, and the input data may include sensor data representative of glucose concentration data, analytes, and other data as well (e.g., insulin pump data, carbohydrate consumption data, histograms and/or counts, data from a continuous glucose monitor (CGM data), time of day, amount of carbohydrates, other food related information, exercise, awake/sleep timer intervals, medications ingested, and the like). Moreover, the input data may comprise historical data obtained over a timeframe, such as 8 hours, 1 day, 2 days, 7 days, 30 days, and/or any other time period. For example, the input data may comprise counts representative of monitored analyte detection levels (e.g., glucose concentration levels) received and stored at system 100 over a period covering a four-week timeframe.

To further illustrate the pattern detector, patterns can be recognized based on one or more predefined triggers (also referred to as criteria, rules, and filters). Furthermore, the one or more predefined triggers may be variable and adjustable based user input and/or programmatically based on one or more rules at the secure server 110. And, some types of patterns may be selected, turned off and on, and/or modified by a user, a user's physician, or a user's guardian, although system 100 may select, adjust, and/or otherwise modify triggers programmatically as well.

Some examples of the types of relationships in the input data that can be considered a pattern are one or more of the following: a glucose level that exceeds a target glucose range (which may be defined by a user, a health care provider, secure server 110, or a combination thereof); a glucose level that is below a target glucose range; a rapid change in glucose level from a low to a high (or vice versa); times of day when a low, a high, an at range, or rapid glucose level event occurs; days when a low, a high, an at range, or a rapid glucose level event occurs; a hyperglycemic pattern; a hypoglycemic pattern; patterns associated with a time of day or week; a weighted scoring for different patterns based on frequency, a sequence, and a severity; a custom sensitivity of a user; a transition from a hypoglycemic to hyperglycemic pattern; an amount of time spent in a severe event; a combination of glucose change and time information;

and/or a pattern of high variability of glucose data. Further, a pattern may be based on a combination of previous pattern data and a currently detected situation, whereby the combined information generates a predictive alert.

Hypoglycemic patterns by time of day may be detected based on events detected by secure server 110. For example, a pattern may be identified in situations where the user has low glucose concentrations around the same time in the day. Another type of pattern, which may be identified, is a "rebound high" situation. For example, a rebound high may be defined as a situation where a user overcorrects a hypoglycemic event by overly increasing glucose intake, thereby going into a hyperglycemic event. These events may be detected based on one or more predefined triggers.

To further illustrate examples of the patterns, basic patterns may be configured to allow a search for certain patterns in the data, such as values within range, high coefficient of variance, and the like. Each pattern may have one dimension, such as within range, with a separate pattern looking specifically for below range, another looking for low coefficient of variance, and the like. Each pattern may be statistically based and use standard descriptive statistics in the application of pattern matching. Each pattern may be assigned scores for various rules encoded with each pattern, such as is it positive, negative, how important an insight is, and the like. Each pattern may also be assigned a possible set of date ranges for which the pattern is applicable. For example, counting the number of times a high glucose value is followed by a low below range is a pattern that just applies to the full range. However, looking at high levels of variance can apply to a month, a week, a day, an intraday, every other hour, hourly, and combinations thereof. Every pattern may be assigned a minimally acceptable score before it can be considered for display or generation of an alert sent to the receiver 102 (or host 199) and/or notification message sent to remote monitor 114. Each pattern (and any associated triggers/rules) may be processed for a set of data for a certain timeframe, and if the pattern is applied and meets certain minimal requirements, then the patterns are ranked according to significance. As such, the ranked patterns may each correspond to an alert sent to the receiver 102 (or host 199) and/or notification message sent to remote monitor 114 (or a primary monitor or secondary monitor access the remote monitor 114).

Connection establishment refers to the process of adding one or more remote monitors to system 100 to provide a second layer of oversight into the operation of sensor system 8 and receiver 102. The connections to the remote monitor 114 may be established based on an invitation sent to the remote monitor 114. This invitation may be sent with the consent of the receiver 102, gateway 104 (e.g., via a user interface therein), and/or host 199. For example, the receiver 102 and remote monitor 114 may be required to both accept invitations or to enter a code (e.g., a password, shared secret, and the like) in order to opt in to the remote monitoring provided at system 100.

To illustrate further with respect to FIG. 1, host monitoring system 198A may have a single remote monitor 114A or a plurality of remote monitors 114A-114M, and the rules associated with when the remote monitors receive alerts and what types of alerts should be sent may be stored at the secure server 110. For example, first remote monitor 114A may receive notification messages during the day, while second remote monitor 114B may receive notification messages at night, although other schedules may be used as well. As another example, first remote monitor 114A may have high and low threshold values that trigger an alert to remote monitor 114A that are different than one or both of the high and low threshold values that trigger an alert to remote monitor 114B. Moreover, one or more rules may define first remote monitor 114A as a primary monitor, while second remote monitor 114B may be defined as a backup or secondary monitor.

The remote monitor 114 may acknowledge a received notification message by activating (e.g., opening, interacting with, accessing, selecting, and the like) the remote monitoring application which causes a message to be sent at 194 (FIG. 3) to the secure server 110 or responding to a message presented at the user interface of the remote monitor. If the secure server 110 does not receive any form of acknowledgement that the user has seen or otherwise acknowledged the notification message at the remote monitor after a predetermined amount of time (which may depend on the severity or type of the event), the secure server 110 may resend the notification to the remote monitor 114. In some example implementations, the secure server 110 may receive a message from the notification service 112 that the remote monitor 114A is out of service or otherwise unreachable, in which case the secure server 110 may resend the notification message to a different remote monitor 114B. The delay used by the secure server for resending the notification messages may be configured based on the severity or type of the event, and the secure server may also include rules defining a predetermined quantity of unsuccessful resends before escalation to another primary monitor, a secondary/backup monitor, an emergency medical service, and the like. And, this predetermined quantity of unsuccessful resends may also be configured at the secure server to vary based on severity or type of the event or user configured.

In some example implementations, as illustrated in FIG. 1, the remote monitor 114 may receive notification messages for a single host monitoring system 198A or a plurality of host monitoring systems 198A-198N. Furthermore, a page may be generated by secure server 110 and then sent to the one or more remote monitors for presentation at a user interface at each of the remote monitors, although the secure server 110 may instead send the data to the remote monitor 114 to enable page generation at the remote monitor 114. The page may include a textual and/or a graphical indication of the status of the one or more hosts being monitored. To illustrate, a school nurse may have a remote monitor 114 with a page depicting each of the host monitoring systems 198A the remote monitor is monitoring. Each remote monitoring system 198A-198N may be associated with a student. In this example, the page may have the status information for each of the students, the most recent notification message for each of the students, a graphical or a textual indication that the student is within limits, or an indication that the student is above limits, and the like. Each student may be associated with a cell (a defined space on the display). As such, the nurse may quickly view the user interface and see the status of each of the students being monitored. A graphical indication may be used to visually convey the overall status of each student in each student's cell. For example, a so-called "smiley" face icon may indicate the student's glucose levels are within limits and a so-called "sad" face icon may indicate the host's glucose levels are of concern because they are above a threshold. Moreover, in some example implementations, the page may be presented on a display, so that a selection (e.g., touch on a touch screen, mouse over, click, etc.) of a cell, notification or face icon results in additional information being provided to the remote monitor. For example, selecting a cell of a student may cause the remote monitor 114 to access the secure server 110 and then receive additional information, such as one or more of current and prior glucose levels, patient information, and the like, and update the display page or transition to a new display page that displays information about the selected student in more detail (e.g., displaying a trend graph of the student's glucose level over the past three hours). Although the previous example refers to glucose levels and specific types of messages and icons, other types of events, messages, and icons discussed herein may be used to convey the status of a host.

In some example implementations, the page discussed above may be configured as a so-called "dashboard" including dynamic content. For example, the icons for the host-patients requiring the greatest care or attention (e.g., the patients with glycemic levels that are extremely high or low) may be arrange in the top row of page to allow the remote monitor to quickly ascertain the state of riskier host patients. Although the previous arrangement described using the top row of the page to segregate some of the so-called riskier host-patients other segregation schemes may be used (e.g., different colors, intensities, and/or locations on the page). Furthermore, the page may be considered dynamic as the patients segregated for extra attention may change over time causing the page to depict different icons for different patients in the segregated top row of the page. Examples of dashboards are discussed in greater detail with respect to FIGS. 18A and 18B.

Designating Remote Monitors

In some example implementations, an entity, such as a user, may be designated by secure server 110 as a primary monitor. When this is the case, the primary monitor at remote monitor 114 may not be available due to for example a dead battery of the remote monitoring 114A, a device out of service, a lack of radio reception, and the like. A secondary monitor may thus be designated by secure server 110 to receive the notification message, which would otherwise be sent to the primary monitor. The secondary monitor may have access to another remote monitoring device 114 and thus receive the notification message, when the first notification message to the primary monitor is not received or acknowledged within a predetermined amount of time. The amount of time can be variable based on the severity or type of event. In addition to monitoring acknowledgements from the remote monitor 114, the secure server 110 may access the quality of service mechanisms at the notification service 112 to determine whether the remote monitor 114 device is not in service (e.g., due to a failure, a dead battery, out of range, or otherwise not accepting notification messages) to enable the secure server 110 to select another monitor that is in service.

Escalation

The remote monitor 114 may, in some example implementations, generate a message for presentation requiring some form of acknowledgement or action by the user of the remote monitor 114 (e.g., a primary or secondary monitor) to confirm receipt of a notification message. The acknowledgement or action may comprise responding to the notification message, opening a remote monitoring application at the remote monitor 114, and the like. Moreover, if the action is not performed within a predetermined amount of time, the secure server 110 may determine that the user of the remote monitor has not seen (or otherwise been notified by) the notification message. When this is the case, the secure server may escalate the notification message to another remote monitor as defined by one or more rules at the secure server. The secure server may also check the push notification service (or quality of service mechanism therein) to see if the notification message has been delivered. If not, the secure server may determine that the user of the remote monitor has not seen the notification message and use this as a basis to escalate the notification message to another remote monitor.

In some implementations, the secure server 110 may include one or more rules defining an escalation sequence defining which notification messages should be sent to primary first remote monitor 114A and, given an out of service state, when the messages should be resent to one or more other remote monitors 114B-114M. During configuration of the remote monitors 114A-114M, the secure server 110 may be configured via user input (e.g., the host and/or one or more of the remote monitors) how and/or when each of remote monitors 114A-114M is to be notified in an escalation sequence. This escalation sequence configuration may be defined by a user or provided as a default setting (which may be reconfigurable or adaptable over time based on the responsiveness of the user/host/monitor) and may vary based on severity of the event and type of event. For example, the escalation sequence may define rules defining when to alert a host-patient at a receiver 102, when to escalate to a primary monitor at a remote monitor, when to escalate to a secondary monitor at a remote monitor, and/or when to escalate to an emergency medical service or 911-emergency response.

In some example implementations, the escalation rules may be different for each of the remote monitors 114A-114N and/or different from the thresholds set for the host monitoring system 198. For example, a first rule may define that if a glucose value exceeds a first threshold value, the secure server 110 should send an alert to first remote monitor 114A. The secure server 110 may include a second, separate rule that defines sending a notification message to a second remote monitor 114B when the glucose value exceeds a second threshold value, and yet another third rule that defines sending another notification message to a third remote monitor 114M when the glucose value exceeds a third threshold value. In addition, a rule may define sending a notification to more than one remote monitor, such as all remote monitors or a subset of the remote monitors monitoring a host. The rules may be configured by a user (e.g., using receiver 102, gateway 104, workstation 22, etc.) or provided as default settings (which may be reconfigurable by a user).

Furthermore, if a user at the receiver 102 does not acknowledge an alert within a predetermined amount of time, an escalation sequence may also be implemented. For example, referring to FIG. 2A, the secure server 110 may determine (e.g., by monitoring sensor data received from receiver 102 and knowing the thresholds on the receiver) that receiver 102 alerted (or should have alerted) host 199, where the alert required an acknowledgement. The acknowledgement can be in the form of a user responding to a message presented on a user interface 122 of receiver 102, or the user otherwise curing the alert, such as taking an action that can be measured by a device associated with the host-user (e.g., medicament pump 2 indicating that insulin has been administered to the user, an analyte measurement indicating that the underlying cause of the alert is no longer a problem because measured level above a threshold or trend moving in a desired direction, etc.). In this example, if the secure server 110 does not receive some form of acknowledgement and/or an indication of the underlying event that triggered the alert is cured after waiting a predetermined amount of time, the secure server 110 may resend the alert and/or send a notification message to a primary remote monitor, a secondary remote monitor, and/or an emergency medical service. And, this escalation, including the retries and delay, may be configured at the secure server 110 to vary based on the severity and/or type of event triggering the alert.

Reminders

In some example implementations, the secure server 110 may include rules providing a so-called "follow-up" reminder. For example, if a host-user at receiver 102 has not taken an action, such as take insulin, drink a glass of juice, etc., the secure server 110 may send a reminder notification to the remote monitor 114 and/or to the receiver 102 and/or gateway 104 after a predetermined amount of time. The predetermined amount of time and which of the one or more of remote monitors 114A-114M, receiver 102, gateway 104 associated with a reminder may be configurable and may vary based on severity of the event and/or type of event.

Furthermore, in some implementations, the secure server 110 may re-send notifications repeatedly (e.g., every 5 minutes or any other time) to remote monitor 114 and/or receiver 102 until the receipt of the notification message is acknowledged. In some example implementations, the secure server 110 may configure different alarm types to be triggered by the receiving device (e.g., remote monitor 114 or receiver 102) as each re-send is sent to the receiving device (e.g., successively increasing volume, brightness, or vibration with each repeated, unacknowledged notification message, or triggering a vibratory alarm with a first reminder and a vibratory alarm with a second reminder, etc.). Opening a message from the secure server 110 at receiving device may serve as an acknowledgment, as well as other actions detectable by the secure server.

In some example implementations, a user designated as a primary monitor may signal to secure server 110 an inability to provide monitoring by sending a message to secure server 110 and/or receiver 102, using, for example, remote monitor 114A or workstation 22. When this is the case, the secure server 110 may demote the primary monitor to a secondary (or backup monitor) and promote one of the secondary monitors to a primary monitor. The secure server may have rules defining which of the secondary monitors may be promoted or each of the secondary remote monitors may be polled to assess availability to assume the role of primary remote monitor. And, the secure server 110 may send a message (via notification service, for example) to the secondary monitor that has been promoted to a primary monitor that it has been designated as a primary monitor (and send a corresponding message to a demoted primary monitor).

To assure quality of service with respect to the receipt by the remote monitors of notification messages, one or more operations may be performed to mitigate the potential loss of a notification message sent to remote monitor 114. For example, if notification service 112 comprises a push notification service (e.g., Apple Push Notification Server, Google Cloud Messaging Server, and the like) and the notification service cannot be contacted (or a connection cannot be established between secure server 110 and notification service 112), the secure server 110 may send notification via another mechanism, such a separate a short message service (SMS) message directly to the remote monitor 114, a phone call, an email, or any other mechanism to establish contact with the remote monitor(s) and/or the users associated with those remote monitoring devices.

Registration/Invitations for Remote Monitoring

As noted above, in some example implementations, the devices used at system 100 may be required to register with the secure server 110. To illustrate with respect to FIG. 2B, the receiver 102 (which may be implemented on a processor-based wireless device, such as a smart phone or a tablet computer) may send a message via the public land mobile network or other network(s) to invite remote monitor 114 to accept a connection establishment request from secure server 110. If accepted, remote monitor 114 may be provided with notification messages for events associated with receiver 102 and access to sensor data and reports associated with host 199. Although the previous example describes the receiver 102 sending an invite to remote monitor 114, other devices, such as secure server 110, gateway 104, user communication device 105, workstation 22, and/or remote monitor 114, may send invitations as well or instead, depending upon the implementation.

In some example implementations, the receiver 102 may send a plurality of invitations to a plurality of remote monitors 114A-114M. Moreover, the invitations may be managed by the receiver 102, gateway 104, user communication device 105 and/or secure server 110, so that at any given instant of time, a user can monitor the status of invitations, such as how many invitations have been sent, how many have been accepted, how many have been rejected, and the identity of any primary and secondary remote monitors. For example, receiver 102 gateway 104, user communication device 105 and/or secure server 110 may manage the invitations, so that at any given instant, a quantity of remote monitors 114A-114M does not exceed a threshold amount (e.g., 5 or 10 remote monitors).

Moreover, the receiver 102, gateway 104, user communication device 105 and/or secure server 110 may also manage the quantity of remote 114 monitors based on location and/or time, so that a host-user has a predetermined quantity of remote monitors 114 at any given location and/or any given time.

In some example implementations, a host 199 or caretaker of host may manage the status of invitations (e.g., invitation sent, invitation accepted, monitoring canceled, and the like) via receiver 102, gateway 104, user communication device 105 and/or secure server 110. For example, one or more user-interactive pages may be presented on a computer display (e.g., of receiver 102, gateway 104, user communication device 105, or workstation 22, etc.) including the status of the invitations (e.g., whether invitation pending, denied, or accepted). These one or more pages may be configured to allow changes to the rules associated with the remote monitors 114A-114M. For example, changes may be made to the rules used to trigger notification messages, the designation of primary monitors (including time and location designations), the designation of secondary monitors (including time and location designations), the escalation sequence and escalation threshold settings, and the like. In addition, the page(s) may provide a list of remote monitors from which a user can designate primary and secondary remote monitors and send invitations to any selected monitors. The page(s) may allow configuration of permissions, such as whether a remote monitor 114 is authorized to receive one or more of notification messages, authorized to view patient data (e.g., sensor data including current and/or past data), and the like.

Figure 12:
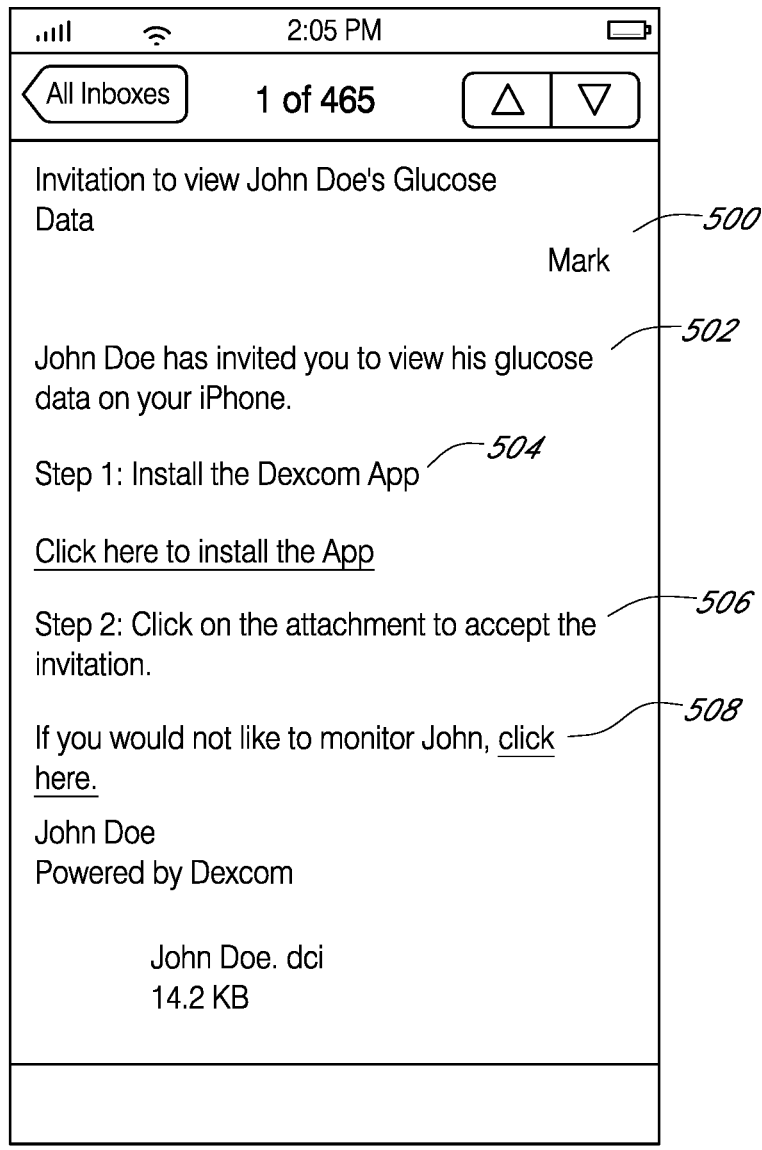
FIG. 12 depicts an example invitation page presented at a remote monitor in the form of an email message in accordance with some implementations.

FIG. 12 depicts an example invitation page 500 presented at a remote monitor 114 in the form of an email message. In this example, a user, "John Doe," associated with a sensor system 8 and receiver 102 has invited remote monitor 114 to be a monitor as indicated by the invitation at 502. Moreover, the invitation may include instructions for the remote monitor, which in this example includes clicking on a link at 504 to allow a download of the remote monitor application code from secure server 110 or another server (e.g., iTunes server operated by Apple, Inc.) and accepting the invite at 506 (which sends an acceptance message to secure server 110). The remote monitor may also be given the option to not accept the invitation to monitor by selecting a user-selectable decline icon 508, which may notify secure server 110 of the decline indication.

To register an invited remote monitor 114 with the secure server 110, the remote monitor and the receiver 102 may each input a value, such as a code, a shared secret, a link (e.g., a uniform resource locator), a password, or a combination thereof, to allow connection establishment and thus enabling remote monitor 114 to receive notification messages for events associated with receiver 102 and to have access to sensor data and reports at secure server 110. Moreover, a user, such as host 199, may access an Internet browser using workstation 22 of FIG. 1, for example, to access secure server 110 and login to view and manage the one or more devices granted remote monitoring privileges.

In some example implementations, one or more of the devices of remote monitoring system 100 (e.g., remote monitor 114, receiver 102, gateway 104, user communication device 105, or workstation 22) may need a code, such a prescription code provided by a health care provider, in order to register with secure server 110. The code may expire after a predetermined time and/or may be limited to a predetermined number of uses (e.g., a single use code that can be used once to register with secure server 110 to obtain a remote monitor code). Furthermore, the code may also define at the server 110 a configuration for the device being registered as a remote monitor 114, such as permissions (e.g., whether can receive notifications, view past sensor data and/or view current sensor data) of and/or alert settings associated with the remote monitor.

In some example implementations, the secure server 110 may have configuration information defining the identity of the receiver 102 and remote monitor 114, so that a user, such as host 199, may access secure server 110 and then add one or more devices, such as receiver 102 and remote monitor 114 to the user's system. The remote monitor 114 may query secure server 110 to obtain information regarding which hosts (or receivers) the remote monitor is allowed to monitor and the secure server can configure the remote monitor 114 accordingly. In some example implementations, the notification messages sent to the remote monitor(s) may be configured to suit the needs of a given remote monitor-user and these needs may be different from the needs of the host-patient. Accordingly, the rules dictating the sending of a notification message to remote monitor 114 may be different from a rule used to trigger an alert to the receiver 102 being used by the host-patient.

The following provides an illustrative example of a caregiver using remote monitor 114 as part of host-patient care with reference to FIG. 2A. Specifically, the caregiver may be administering an analyte therapy to the host-patient. For example, the caregiver may be a parent of a young child. In this example, a parent may want to receive notification messages, which are identical to the alerts, sent to the receiver 102 (or triggered by the receiver) and host-patient (which in this example is a child). Moreover, the secure server 110 may obtain the receiver 102 settings through the gateway 104. During the configuration of the remote monitor 114, the secure server 110 may prompt the parent to select a set of rules that are identical to those being used by the child's receiver. In this example, any subsequent changes made to the set of rules being used for the child's receiver would be programmatically propagated to the set of rules being used to send notifications to the parent's remote monitor 114. Although the previous example described the same set of rules being used from the host and monitor, the host and monitor may implement different rules as well.

The following provides another illustrative example of a host-patient administering treatment but in this case, the host-patient or caregiver may not want a high degree of oversight of the host-patient. To that end, the caregiver at remote monitor 114 may want the host-patient to receive an alert first, but allow the patient-host time to act on the alert to correct or acknowledge the event prior to an alert being sent to the caregiver. As an example, an alert triggered by the receiver 102 may indicate a hypoglycemic or hyperglycemic event, and if after a certain period of time the host-patient has not taken one or more predetermined action(s) to remediate the event (as evident by subsequent glucose measurement indicating the same or worsening patient state, for example), the caregiver at remote monitor 114 may receive a notification message responsive to the event. That is, if a patient-host using receiver 102 does not respond or acknowledge an alert in a predetermined manner, the caregiver at remote monitor 114 may then receive a notification message. The caregiver at remote monitor 114 may thus receive a notification message when the host patient at receiver 102 fails to respond to, or acknowledge, certain, real time events, such as a low glucose event (which may be considered severe as the host-patient may be incapacitated or unaware of the event so a notification to the remote monitor is in order). However, the secure server 110 either delays sending reminders or stops sending reminders responsive to a notification message if one or more predetermined occurrences are identified by the secure server. The one or more predefined occurrences can be curing the underlying event triggering the alert, acknowledging the alert or taking a defined action, such as administering insulin and the like (which causes data to be sent to the secure server a remote monitor.

Further, the secure server 110 may be configured with a delay to wait for an acknowledgement or action before notifying the remote monitor 114, and this delay may vary based on the type and/or severity of the condition causing the alarm, and vary depending upon default or user configured settings of the remote monitor. In addition, the secure server 110 may be configured to also monitor data from the receiver 102 even after an acknowledgement message is received from the receiver 102 in response to an alert. For example, the secure server 110 may receive the acknowledgement message (which may be a message sent by receiver 102), but secure server 110 may wait a predetermined time for sensor data from the receiver 102 confirming that the host-patient has indeed taken action. Again, this delay may vary based on the type and/or severity of the condition causing the alarm.

The following provides yet another illustrative example of a host-patient administering treatment but in this case, the host-patient is highly independent so the remote monitor may only be triggered in an emergency. For example, the secure server 110 may include a rule to trigger a remote monitor in the case of an emergency, such as a severe hypoglycemia event occurring at night. In this scenario, the host-patient may not be able to respond to the alert of the event, so the secure server 110 may trigger a notification message if the glucose falls to an extremely low level for a period of time or the user does not respond after a period of time to the very low glucose alert sent to receiver 102. And, the period of time may be varied based on the type and/or severity of the condition causing the alarm.

The following provides another illustrative example of a host-patient that is highly independent but is hypoglycemia unaware and has no trusted sources for emergency response. In this use case, the host-patient may select a remote monitor 114 associated with an emergency medical service so as to automatically notify the service in the event of a severe hypoglycemic event when the glucose falls to an extremely low level for a period of time or the user does not respond after a period of time to the very low glucose triggered by receiver 102.

Managing Remote Monitor Alert Settings

In some example implementations, a user may manage the alerts for each of remote monitors 114A-114M monitoring a host 199. For example, the host 199 can use host monitoring system 198 to invite remote monitor 114A to be a monitor and configure the permissions at secure server 114 using receiver 102, gateway 104 (including host communication device), or workstation 22. The permission may be specific to one or more certain alerts or global in the sense that all the alerts for remote monitor 114A may be manipulated by the user. Although the previous example describes the permissions being set by a user, the permissions may be determined programmatically as well.

Figure 13:
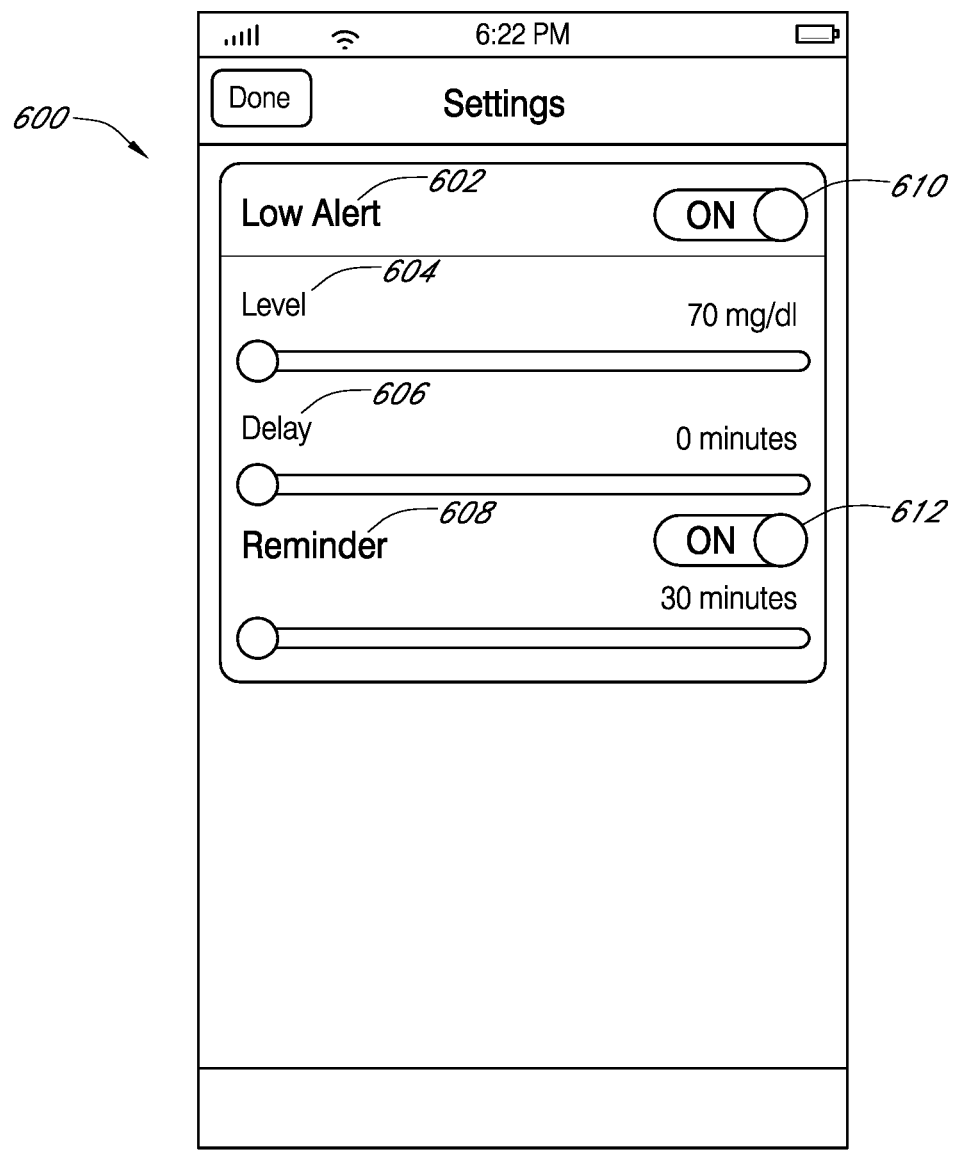
FIG. 13 depicts an example page that may be presented on a display of the host computing device.

To manage alerts, a user may access secure server 110 using a computing device, such as remote monitor 114, receiver 102, gateway 104, host communication device 105 or workstation 22, and manage the alerts by for example setting alerts, changing thresholds, turning alerts on or off, and the like. FIG. 13 depicts an example page 600 that may be presented on a display of the host computing device. The page 600 may allow changes to alerts for a certain remote monitor 114A. In the example of FIG. 6, a low glucose alarm 602 may be turned on 610, and the threshold 604 that defines the threshold configured by the user. FIG. 6 also depicts that delay 606 may be managed using page 600 as well. For example, the delay 606 may define how long the secure server 110 waits before sending a notification message from the secure server (via notification service) to the remote monitor 114A if the host's glucose concentration remains below the low threshold. In this example, the delay is zero seconds, but can be changed using page 600 to be another amount of time, such as 5, 10, 15 or 30 minutes, or an hour. Page 600 also allows secure server 110 and/or notification service 112 to trigger sending reminders 612 and vary a time 606 associated with triggering the reminders. For example, the reminders represent the amount of time that elapses before the secure server 110 triggers another notification to remote monitor 114A if remote monitor has not acknowledged the alert or if the host has not cured the event that originally triggered the alert. In this example, if a user fails to acknowledge an alert or take corrective action within 30 minutes after an original notification responsive to a reading below 70 mg/dl, the secure server 110 sends another notification regarding the low glucose level to the remote monitor 114A. Although the example described with respect to FIG. 6 refers to a low glucose value, a delay, and a reminder, any other aspect of the alerts for a remote monitor 114 described elsewhere herein can be likewise managed as well, such as high glucose level alerts, high rate of change alerts and the like.

In addition, while the above description with respect to FIG. 6 refers to managing alerts for a remote monitor 114, a similar page can be used by receiver 102, gateway 104 or host communication device 105 to manage alerts triggered by host communication device in the implementations of FIGS. 2a-2C. As an example, host communication device 105 can display page 600 for managing alerts by host communication device independent from receiver 102. In this way, host communication device 105 can function as a secondary alert device for host 199.

In some implementations, a user may modify one or more rules defining alerts representative of events associated with the analyte state of the host. A user may use a computing device, such as remote monitor 114, receiver 102, gateway 104, host communication device 105, or workstation 22, to modify the alert settings, such as low glucose level thresholds and the like, of the host monitoring system 198. In this way, a parent, for example, can modify the settings of their child's remote monitoring system 198.

Although the previous example refers to modifying low glucose alarms, the modification may include varying a first threshold associated with a low level of glucose at the host, varying a second threshold associated with a high level of glucose at the host, varying a delay between when the message is triggered by the receiver 102, varying a time value between when a reminder message is sent, and any other alert that may be triggered for a host monitoring system 198 or remote monitor 114.

Moreover, the secure server 110 may adapt the set of rules used for a host-patient. For example, the set of rules for a remote monitor 114 may be predetermined based on some basic host-patient demographics. After initial use of remote monitoring system 100, secure server 110 may programically adjust thresholds used to trigger some or all events. These adjustments may be made for a variety of reasons. For example, thresholds, such as glucose levels, glucose rates of changes, and the like, used to determine when to trigger an event may be adjusted to reduce the frequency of some alerts and/or notifications as a remote monitor 114 receiving too many messages may decide to ignore the messages. The thresholds may also be adjusted to tighten the range of a patient's glucose variation during the day in order to decrease the variability in a host's day-to-day glucose variability.

In some example implementations, data management tools and CGM analyses may be used to help patients better manage their diabetes or assist clinicians in enhancing recommendations. As CGM data (and/or analyte data) may be provided to secure server 110 in about real time, the data may be used by case managers in payer systems and/or medical systems to enhance ongoing diabetes management. However, it may be impractical for a diabetes case manager to review the resulting so-called "big data." As such, filters may be used to allow exception based reporting of use or glycemic patterns to promote efficient use of the case manager's time by identifying specific issues. To that end, one or more patterns may be defined at the secure server to identify the issues requiring the attention of the case manager. The patterns may include longitudinal analysis or comparisons between time periods. These patterns may also identify high-risk patients, such as those with frequent or severe lows, frequent or severe highs, and/or marked glucose variability. This may be considered particularly important for use with patients on intensive insulin therapy, with hypoglycemia unawareness, poor control, those new to insulin, and the like. The patterns may also identify therapy non-responders identifying, such as those with sustained hyperglycemia, suggesting non-response to therapy or worsening of control, suggesting non-adherence, disease progression, or tachyphylaxis. This may be considered particularly useful when new medicaments are added or therapy is optimized. The patterns may also identify responders or non-responders linked to diabetes education or by particular providers or consultants.

In some example implementations, additional performance information may be gathered at the secure server 110 from patients at a plurality of locations. This additional information may be used to evaluate environmental factors that could influence and affect the sensor's performance. Rather than gathering and analyzing information solely from a single host-patient, data may be gathered at the secure server and then compared on a macro level spanning across a plurality of host patients and/or across a plurality of geographic locations (or regions). In essence, the sensor system's 8 overall effectiveness may be evaluated based upon various environmental factors being monitored. For example, data gathered in real time from across the United States or even the World may show if temperature, humidity, altitude, or the like influence the sensor system's 8 performance and thus provide an indication as to whether the sensor system 8 and/or sensor 10 should be replaced or repaired. Moreover, the secure server 110 may also process received sensor information and identify patterns (e.g., by lot number, region, or the like), and additional algorithms, calibration information or fail-safes may be uploaded based on these identified patterns to improve the sensor accuracy and/or performance.

In some example implementations, the secure server 110 may programmatically track product performance and utilization of a sensor system including sensor 8 and/or receiver 102. For example, the sensor system and/or receiver may programmatically provide to secure server 110 information identifying the sensor (e.g., lot number) and summarizing its performance. The performance metrics may include accuracy, on time, data capture, and the like. Moreover, if one or more sensor performance metrics fall outside of an expected range, then secure server 110 may request additional information to be transmitted from the sensor system/receiver to the secure server to allow classification of the failure mode. For example, the secure server 110 may send alerts and/or notifications to receiver 102, gateway 104 and/or remote monitor 114 that the sensor system 8 and/or receiver 102 needs to be maintained (e.g., replaced, repaired, calibrated, and the like) based on determined performance information. And, the secure server 110 may also be configured to send, based on the performance information, alerts or notification messages indicating that the sensors requires a reset, a new calibration value is needed, or a new sensor should be ordered. The data provided to the secure server 110 may be configurable and stored at a repository coupled to the secure server 110.

Moreover, sensor system tracking by the secure server may include tracking the performance of the receiver's wireless interface. For example, if a hardware error (or any detected error condition) occurs, information related to the error may be transmitted to the secure server 110. The data transmitted may also be used to track feature utilization, which may include alert settings, number of screen visits, and the like. In addition, this data may be used to collect and manage data during clinical studies. Furthermore, the sensor data transmitted to the secure server 110 may also be expanded to tracking of patient performance of glycemic control. When this is the case, performance metrics may include the "time spent" in different glucose ranges, amplitudes of glycemic excursions, insulin dose information, and the like. For example, during a continuous glucose monitoring (CGM) session, data may be automatically transmitted to a secure server 110 and/or a coupled repository accessible to the host-patient and/or the patient's clinical care provider. Accordingly, the above-noted automatic tracking of product performance and classification of failure modes may, in some example implementations, provide more accurate information regarding product performance, facilitate resolving sensor issues experienced by patients, and automate product replacement (or shipment) when the sensor performance is deemed ready for replacement.

In some example implementations, the secure server 110 may provide a closed control loop. Specifically, secure server 110 may send a message to receiver 102, which responds to secure server 110. Moreover, secure server 110 may send messages to remote monitor 114, which responds to secure server 110. Accordingly, secure server 110 may request an action from receiver 102 and/or remote monitor 114, and receive acknowledgement from receiver 102 and/or remote monitor 114, when the action is completed, forming thus a closed loop. The receiver 102 may include one or more aspects of the functions provided by the remote monitor 114, and remote monitor 114 may include one or more aspects of the functions provided by the receiver 102.

Example Host Monitoring System Set-Up Process 1000

Figure 10:
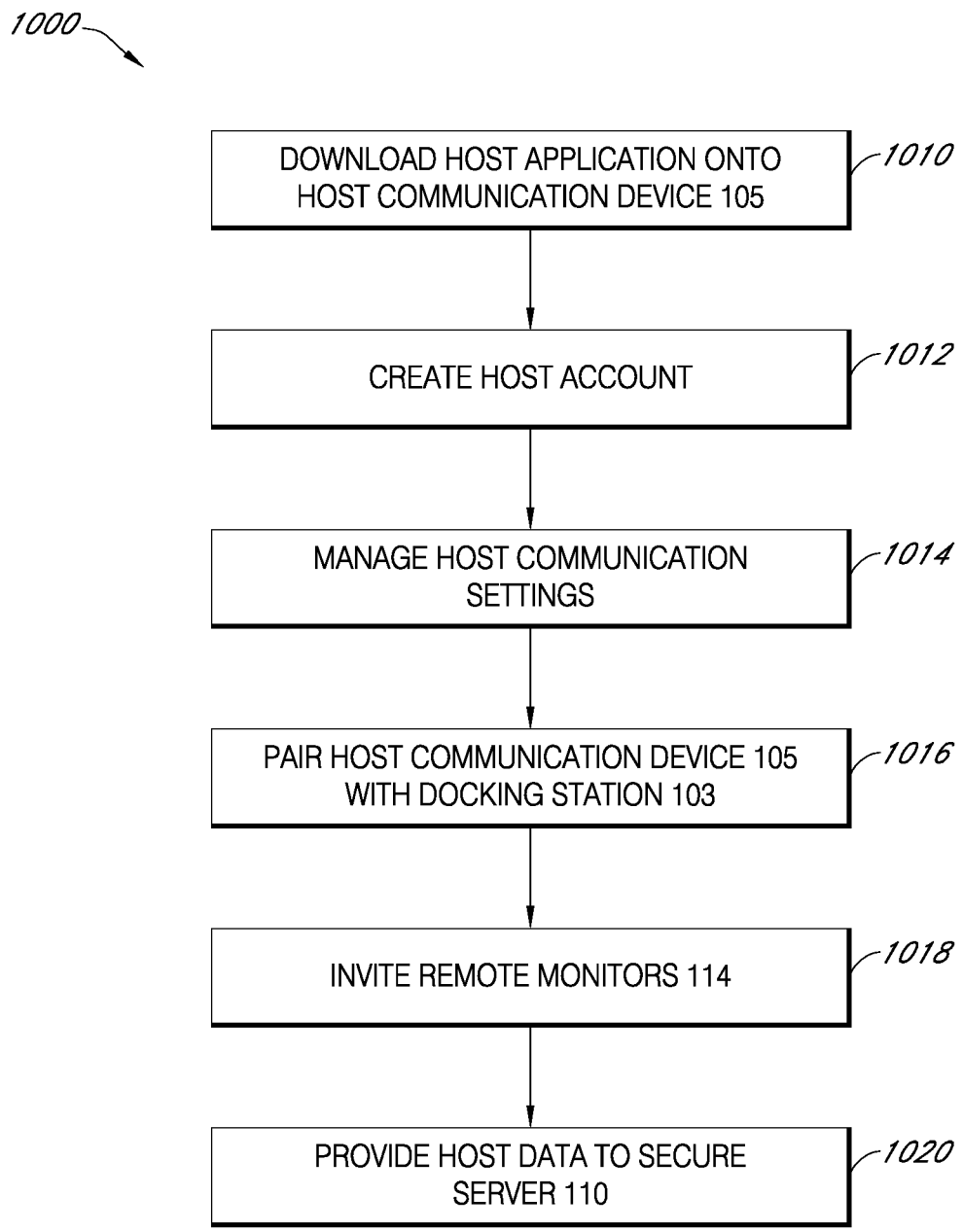
FIG. 10 is a flow chart depicting a process for setting up host monitoring system in accordance with some implementations.

FIG. 10 is a flow chart depicting process 1000 for setting up host monitoring system 198 in accordance with some implementations. For illustrative purposes, the setup process 1000 will be discussed with reference to the remote monitoring system architecture illustrated in FIG. 2C, although it is understood that setup process 1000 can be applied to the architecture of FIG. 2A or FIG. 2B with changes to accommodate the differences of architectures.

Additionally, for further ease of understanding, the following components of FIG. 2C are used in one example of process 1000: the sensor system 8 and receiver 102 make comprise a DexCom G4 Platinum continuous monitoring system, available from DexCom, Inc., where the sensor 10 is a DexCom G4 sensor, the sensor electronics module 12 is a DexCom G4 transmitter, and the receiver is the DexCom G4 receiver; the receiver 102 is docked in the docking station 103 as illustrated and discussed with reference to FIG. 7B; the host communication device 105 comprises an Apple iPhone available from Apple, Inc.; and each remote monitor 114A-114M comprises an Apple iPhone or other mobile phone having an iOS® (commercially manufactured by Apple, Inc.), Android® (commercially manufactured by Google, Inc.) or Windows® (manufactured by Microsoft, Inc.) based mobile operating system.

At block 1000, a user downloads a host monitoring application on to the host communication device 105. (It is understood in the host monitoring application can be downloaded onto gateway 104 the implementation of FIG. 2A or downloaded onto receiver 102 in the implementation of FIG. 2B the host monitoring application can be, for example.) In some implementations, the host monitoring application is downloaded from a server, which can be independent (e.g., operated by a different entity) of secure server 110, such as the Apple App server operated by Apple, Inc. However, in some implementations, the host monitoring application is downloaded from server 110. The host monitoring application comprises instructions for the host communication device 105 to perform the host communication device functions described herein, such as gathering sensor data from the receiver 102 via the docking station 103, transmit the sensor data to the secure server 110, manage alerts of host monitoring system 198, inviting users to become remote monitors of host, manage remote monitor settings, pairing with the docking station 103 and/or receiver 102, and the like.

Once the host monitoring application is downloaded to the host communication device 105, a user can open the application (e.g., by selecting an icon associated with the host monitoring application on a home screen of the host communication device) and uses the application to create an account at block 1012. In addition to storing account information on the host communication device 105, the account is created and stored on secure server 110. In some implementations, creating the account includes entering user identifying information, such as name and email address, a password, and a unique identifier associated with the receiver 102, such as the receiver's serial number. As discussed below in block 1016, the receiver's serial number can be used for pairing the receiver 102 and/or docking station 103 with the host communication device 105, as well as other functions.

Figure 9:
FIG. 9 illustrates an exemplary display page to facilitate entry of the serial number of a receiver for other unique identifier in accordance with some implementations.

FIG. 9 illustrates an exemplary page 900 host monitoring application can display to a user at the account setup block 1012 to facilitate entry of the serial number of the receiver 102 or other unique identifier. Here, the page 900 is an illustration of the location of the serial number to aid the user in finding the serial number of entry. Page 900 also provides an alphanumeric entry field where the user can select to manually enter the serial number. In addition, page 900 provides selectable icons 902 and 904 that allow the user to take a photo of the serial number using a camera of the host communication device 105 and scan in the serial number using a bar code scanner of the host communication device 105, respectively.

At block 1014, the user uses the host monitoring application to manage alert settings for the host communication device 105. The host application can initially present default alert settings, where the user can modify the default user settings using the user interface of the host communication device 105. In some implementations, the alert settings comprise repeating one or more alerts on the receiver 102. This way, the host communication device 105 can amplify (e.g., trigger a different type of alarm than the receiver, such as a louder alarm) and/or echo alarms of the receiver (e.g., only sounding the alarm after a predetermined amount of time from the alarm of the receiver if the event triggering the alert on the receiver has not been cured). The alert settings can also include turning off or on alerts for various events.

The user pairs the host communication device 105 with the docking station 103 at block 1016. In some implementations, to pair the host communication device 105 with the docking station 103, the user powers on the docking station and connects the receiver 102 to the docking station. At this point, the host communication device 105 and the docking station 103 begin a pairing and authentication procedure.

In some implementations, the docking station 103 does not have a display and thus conventional pairing and authentication procedures may not be adequate. Thus in some implementations, receiver 102 provides a serial number to the docking station 103 and a user enters the receiver serial number into the host communication device 105. The host communication device 105 can then transmit the serial number (or encrypted version of the serial number) to the docking station to establish an authenticated communication channel.

The following pairing and authentication procedure may be used in some implementations. In response to the receiver 102 being docked to the docking station 103, the docking station derives an authentication token from the receiver's serial number (which the receiver transmits to the docking station) and puts it in a Generic Attribute Profile (GATT) characteristic. The docking station 103 then broadcasts a general advertisement to bond. The host communication device 105 device looks for the advertisement. After discovering the docking station 103, the host communication device 105 connects and performs a service discovery. The host communication device 105 then attempts to read the GATT characteristic mentioned previously. The docking station 103 responds with an insufficient authorization message (pairing and encryption is required). The host communication device 105 then prompts the user to pair with the docking station 103. Both the docking station 103 and the host communication device 105 compromise a long term key to use for encryption and are then paired. The host communication device 105 then reads the token from the characteristic mentioned above, and using this characteristic, verifies the authenticity of the docking station 103. The host communication device 105, which has previously derived its own token from the receiver serial number entered previously into the host communication device in block 1012, writes this token to a GATT characteristic in the docking station 103. The docking station 103 then uses this token to verify the authenticity of the host communication device and, if authentic, enters a persistent bonded state.

Using the above-mentioned pairing and authentication process, if the two devices (receiver 102 and docking station 103) are disconnected at any point, the docking station 103 directs an advertisement for connection.

At block 1018, the user uses the application on the host device 105 to invite remote monitors 114. Here, the application may prompt the user for identifying information of a potential user of a remote monitor, including a name and email address accessible from a device capable of being a remote monitor 114, such as a mobile smart phone or tablet computer. In addition, the application can prompt the user for permissions that the user wants the remote monitor 114 to have, such as permission to view trend graph data, and alert settings that the user wants the remote monitor 114 to have. Once finished, the application sends an invitation to the remote monitor 114, with the information in the invitation, such as identifying information, permissions and alert settings stored on secure sever 110. The user can invite additional remote monitors using the above described invitation procedure. In some implementations, the application can include a page that lists the status of all invitations sent by the user.

Note that process 1000 can be implemented using a setup wizard implemented by the host monitoring application on host monitoring device 105 to guide the user through the setup process 1000.

Example of Remote Monitor Set-Up Process 1600

Figure 16:
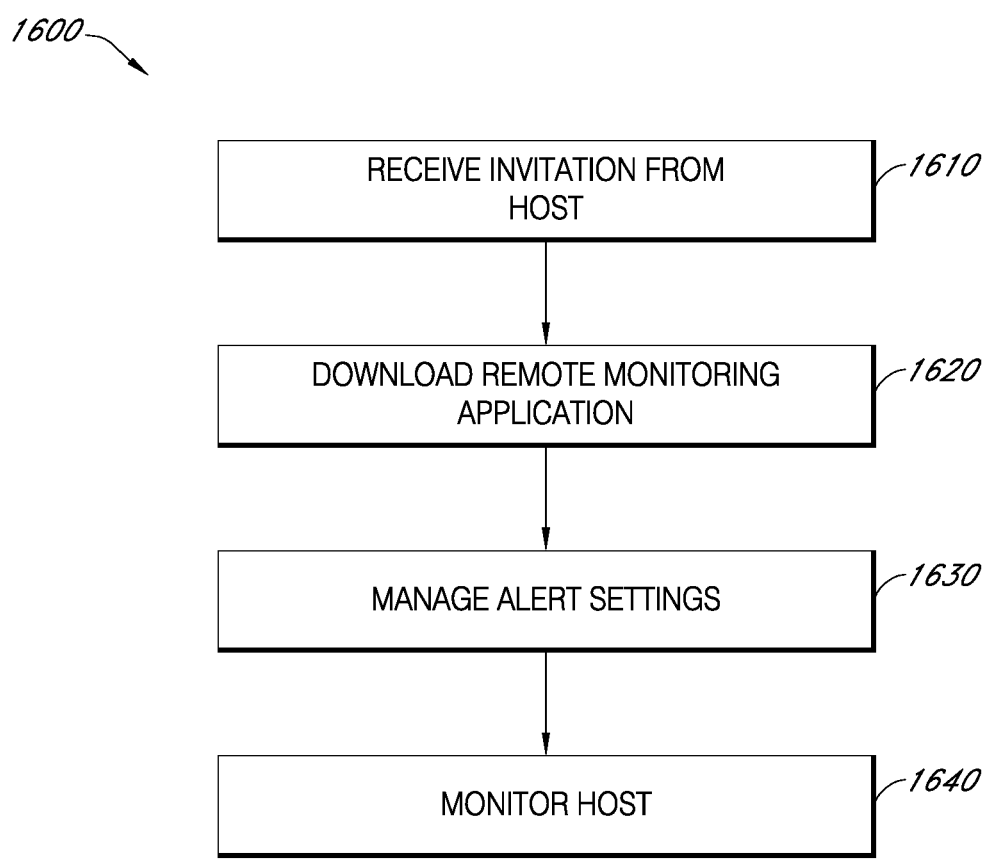
FIG. 16 is a flowchart of an exemplary process of remote monitoring using a remote monitor.

FIG. 16 is a flowchart of an exemplary process of remote monitoring using remote monitor 114. Similar to process 1000, FIG. 16 will be described for illustrative purposes only with respect to the remote monitoring system 100 architecture of FIG. 2C.

At block 1610, a user receives on a computing device, such as a smart mobile phone, an invitation to become a remote monitor. An example invitation is illustrated and discussed in more detail with respect to FIG. 12. In some implementations, a user receiving the invitation can either accept or deny the invitation by selecting an accept icon or deny icon, respectively, in the email. Denying the invitation ends process 1600, whereas accepting the invitation moves process 1600 to block 1620.

At block 1620, the invitation programatically directs the user via the user's computing device to download a remote monitoring application, if the user accepts the invitation. In some implementations, accepting the invitation at block 1610 programatically triggers the user's computing device to automatically access a server carrying the remote monitoring application. The server can be the App Store operated by Apple, Inc. in the case that the user's device is an Apple mobile device. The user then downloads the remote monitoring application onto the computing device.

Note that in some implementations, the user of the remote monitor 114 need not register with secure server 110, as the secure server already has the user's account information from when the invitation was formed in block 1012 of process 1000 (FIG. 10).

At block 1630, the user manages alert settings using the remote monitoring application downloaded on the computing device (now considered a remote monitor 114). The alert settings can initially be set at recommended alert settings set by the person that sent the invitation at step 1012 in process 1000 (or default settings in the case the person sending the invitation did not enter any recommended settings) in some implementations. The user of the remote monitor 114 can then modify any of the recommended or default settings. The settings can include setting threshold values for when to trigger an alert to the remote monitor, delays, reminders and no data alert settings, discussed in more detail elsewhere herein. The remote monitor 114 may then transmit the settings of the remote monitor to the secure store for storage and use when triggering alerts associated with the remote monitor.

At block 1640, the remote monitor 114 monitors hosts' analyte levels as permitted. The monitoring can include monitoring a plurality of hosts using the remote monitor, as discussed in more detail with respect to FIG. 1. The monitoring can include receiving notifications triggered by secure server 110 and sent via notification service 112 and viewing sensor data accessible from secure server. For example, in some implementations, a user can activate the remote monitoring application on remote monitor 114 to view a dashboard page of a plurality of host's glucose levels.

Example Invitation to Become Remote Monitor

As discussed above in block 1610 of FIG. 16, a user can receive an invitation to remotely monitor host 199. In some implementations, the invitation is the form of an email, such as that depicted in FIG. 12. The user can accept or deny the invitation using the email. The user can accept the invitation by indicating that the user wants to install the remote monitoring application by selecting selectable text 504, or deny the invitation by selecting selectable text 508. If the user denies the invitation, then the remote monitoring system 100 can notify the host that sent the invitation of the denial by sending a notification via server 110 and/or notification service 112 to communication device 105, for example. However, if the user accepts the invitation, then the remote monitoring system 100 can notify the host of the acceptance by sending a notification via server 110 and/or notification service 112 to communication device 105, for example, and process 1600 continues to block 1620.

In some implementations, a receipt accepting the invitation automatically sets up a remote monitoring account on server 110. That is, the recipient need not log in and create an account, as the host provided account creation information (recipient name, email, phone number and the like) for the recipient when generating the invitation. Further, the host can include a picture of the host during the invitation creation process so that the invitation includes a picture of the host in the vitiation sent to the recipient (which can help the recipient know the invitation is valid) and the picture of the host can be used as the picture of the host in the remote monitor (such as on a dashboard as discussed with reference to FIGS. 18A and 18B and elsewhere).

The invitation can include a single use token which the recipient of the invitation can use to accept the invitation without requiring the recipient to log into the remote monitoring system, in some implementations. The toke can be in the form of a Globally Unique Identifier (GUID). The invitation may also include a timestamp of when the invitation was sent and when the invitations expires.

System Status View

In some implementations, a user of remote monitoring system 100 may not readily know if the remote monitoring system 100 is working or why the system may not be working. For example, in the implementation of FIG. 2B, a host 199 may not realize that data is not being transmitted from the sensor system 8 to the server 110, or even if the host realizes that data is not being transmitted, the host my not recognize where the problem lies so that data transmission can resume. Accordingly, some embodiments provide a system status page the help a user understand if the system is working correctly, and, if not, what the source of the problem may be.

Figure 11A:
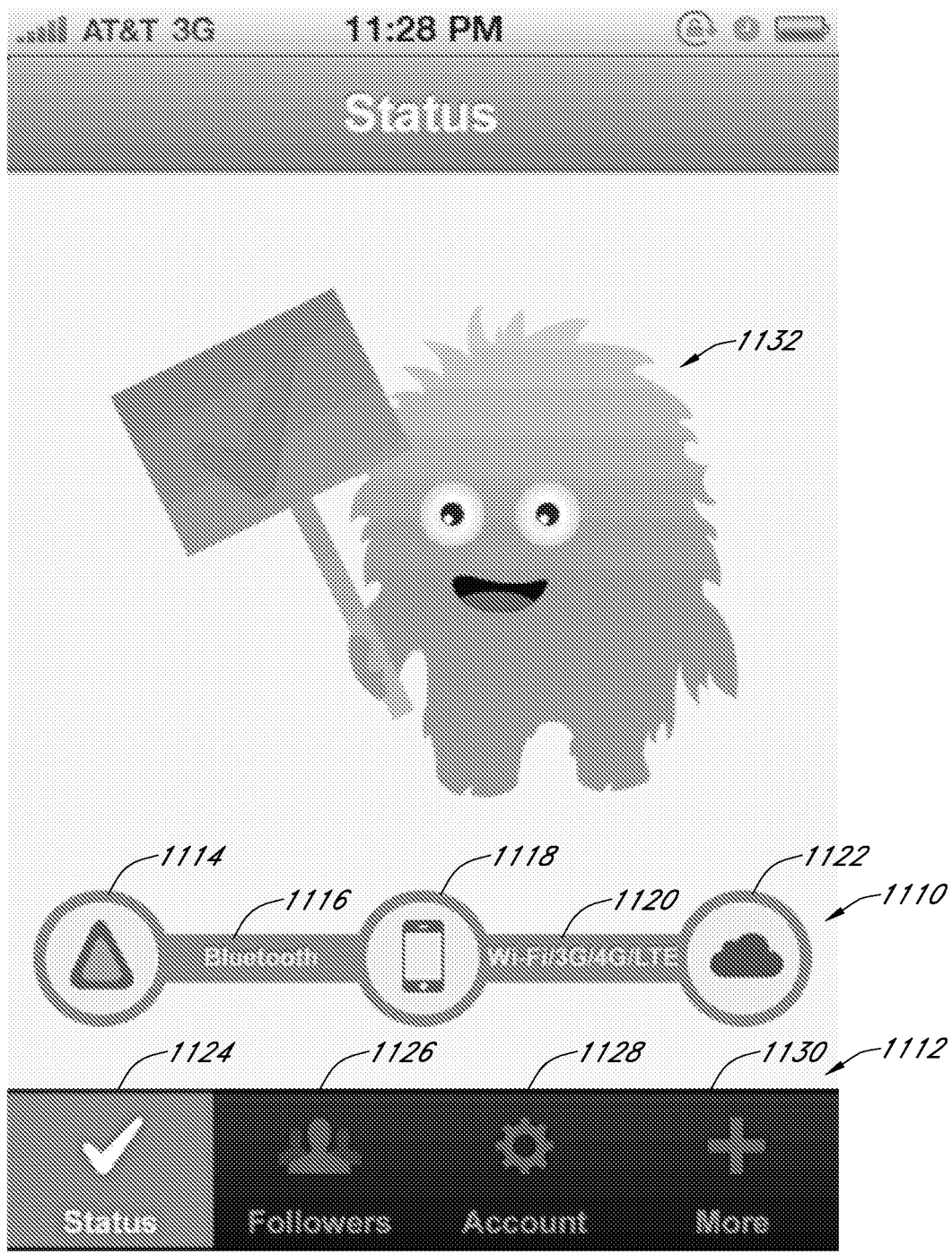
FIGS. 11A and 11B are exemplary views of a status page in accordance with some implementations.
Figure 11B:
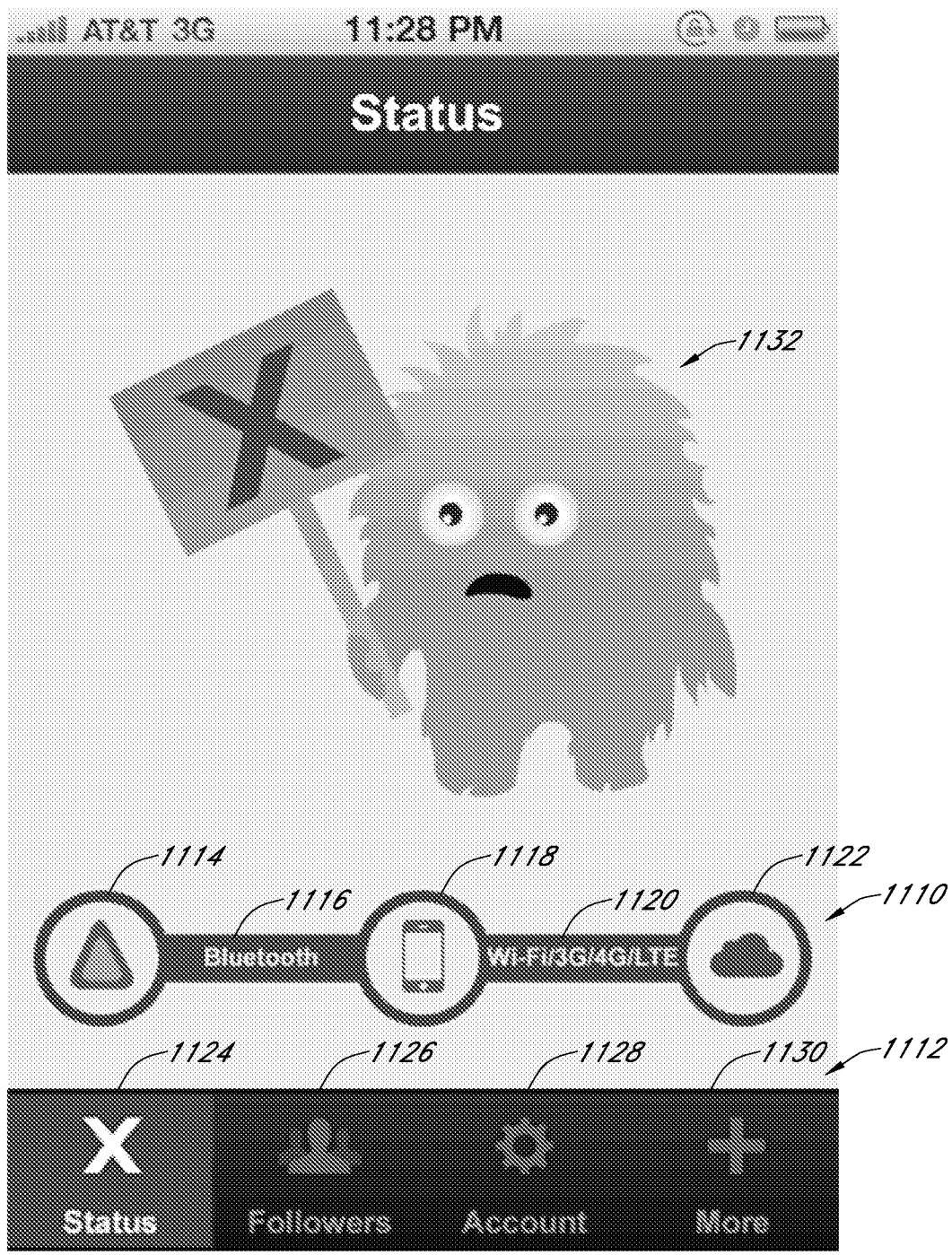

FIGS. 11A and 11B are exemplary views of a status page 1100 in accordance with some implementations. Status page 1100 includes a status bar 1110 that includes representations of various components of remote monitoring system, which in this example, includes docking station 1114, host communication device 1118 and server 1112, and the communication channels between each of the components, such as a near-filed wireless communication (Bluetooth®) channel between the docking station and the host communication device, and a communication channel (e.g. Wi-Fi or cellular) between the host communication device and the server 1112. The status bar can indicate where connections are working and where connections are not working. For example, if a connection is determined to be working, then the connection can be graphically displayed in a first state, and if the connection is not working then the connection can be graphically displayed in a second, different state. The first state and the second state can be, for example, a different color (e.g., green if working, red if not working) and the like. Further, each portion of the status bar, 1114, 1116, 1118, 1120 and 1122 can be user selectable, where if a user selects a particular portion, the host monitoring application can display help information (in the form of a pop-up message or new display screen, for example) that can help a user resolve issues associated with the portion selected by the user. For instance, if the user selects the docking station icon 1114, the remote monitoring application can display a message asking the user to make sure the docking station is plugged in, for example.

Status page 1100 can also include a character icon 1132 that displays an overall status of the system. In the example of FIGS. 11A and 11B, the character icon 1132 is in the form of a monster holding a sign. The appearance of the character icon 1132 can change based on the status of the system so a user can quickly determine the status by viewing the character icon. For instance, character icon 1132 can have a smiling expression and holding a sign with a check mark to indicate the system is working and transmitting sensor data, as illustrated in FIG. 11A. In contrast, the character icon 1132 can have a frowning expression and holding a sign with an X to indicate the system is not working, as illustrated in FIG. 11B. The eyes of the character icon 1132 can also help indicate to a user if the system is working, such as the eyes blinking if host monitoring application is working, or the eyes not blinking if the eyes aren't blinking. The blinking of the eyes can also correspond to the transmission rate between the docking station 103 and the host communication device.

Host monitoring application can also display a status tab 1124 on status page 1100 and any other pages displayed by host monitoring application, as illustrated in FIGS. 11A and 11B. Status tab can be part of a menu that includes a plurality of different selectable tabs associated with different display pages of the host monitoring application that, when selected, display the associated display page The tabs in FIGS. 11A and 11B additionally include a follower tab, 1126, account tab 1128 and more tab 1130. Notably, the status tab can always display an indication of the connection state of the system, such being displayed in green and with a check mark, as illustrated in FIG. 11A, if the system is working, or in red and with an X, as illustrated in FIG. 11B, if the system is not working. The status tab can be displayed regardless of the current page being displayed, thereby providing the user with an indication of the status of the system regardless of the page being displayed.

In some implementations, host monitoring system 198 may be configured to periodically send messages to server 110. If the server detects a lack of messages from the host monitoring system 198 for a predetermined amount of time, then the server can trigger a notification to be sent to the host monitoring system (such as receiver 102, gateway 104 or host communication device 105) notifying the host of the lack of messages so that the host can check to determine if the host monitoring system is working, using for example status page 1100.

Host Monitoring Control Pages

Host monitoring application can also include various display pages that allow the user to view statuses of remote monitors and configure permissions and settings associated with remote monitors.

Figure 14:
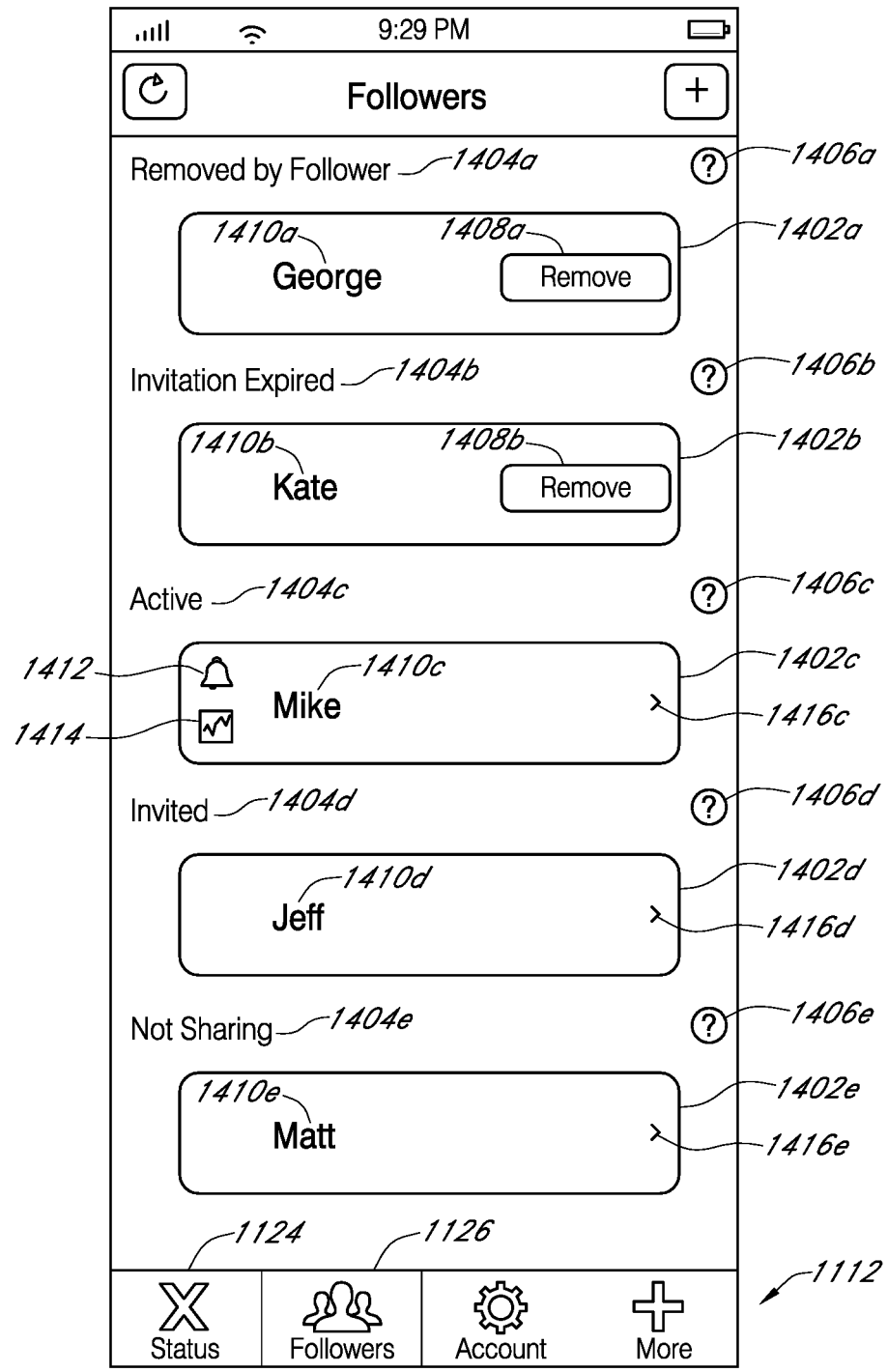
FIG. 14 illustrates an overview page in accordance with some implementations.

FIG. 14 illustrates an overview page 1400 in accordance with some implementations. Over view page can include a plurality of cells 1402a-1402e, each cell associated with a remote monitor or potential remote monitor. Each cell can include a name 1410a-1410e associated with the remote monitor for identification purposes. The cells 1402a-1402e can also be displayed according to a status of the remote monitor. For example, cell 1402a is grouped under a removed by remote monitor (referred to as a follower in FIG. 14) status 1404a, cell 1402b is grouped under an expired invitation status 1404b, cell 1402c is grouped under an active status 1404c, cell 1402d is grouped under an invited status 1404d, and cell 1402e is grouped under a not sharing status 1404e. Not that a plurality of cells can be displayed under each group; FIG. 14 merely illustrates one cell for ease of explanation of the different statuses.

Page 1400 also includes a selectable help icon 1406a-1406e associated with each group status. By selecting a help icon, the host monitoring application can provide further information to a user that explains what the associated status involves. The help information can be displayed in a pop-up window for example.

Icons can also be displayed in a cell that illustrate permissions and/or enabled functions associated with that remote monitor. For instance, icons 1412 and 1414 indicate that remote monitor associated with cell 1402c has notifications enabled and has permission to view trend graph information associated with the host being monitored.

Selectable tabs can also be provided in each cell. For example, FIG. 14 illustrates removal tabs 1408a and 1408b that remove the cell from the page when selected by a user. Arrow tabs 1416c-1416e can be used to provide further information about the remote monitor associated with that cell. For example, selecting a selectable arrow 1416 can cause the host monitoring application to transition to settings display page that provides more detail about the associated remote monitor and the remote monitor's settings.

Figure 15:
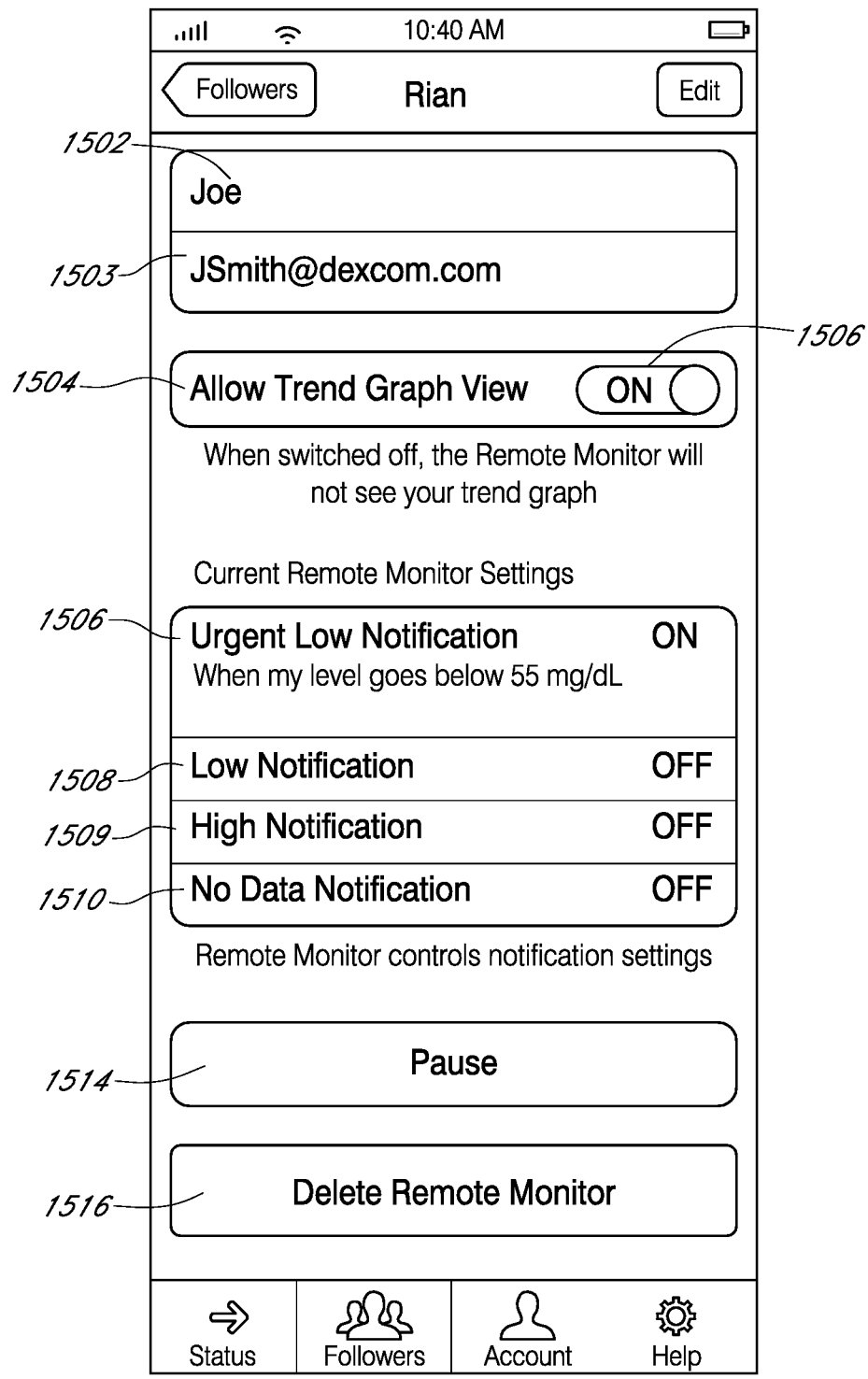
FIG. 15 is an exemplary settings display page in accordance with some implementations.

An exemplary settings display page 1500 is illustrated in FIG. 15 in accordance with some implementations. Settings display page 1500 can include identification information, such as a name 1502 and email address 1504 associated with the remote monitor, permissions of the remote monitor and notification settings of the remote monitor. In the example of FIG. 15, the permissions can include a trend graph permission 1504 tab that a user can use to toggle between allowing and denying. If permitted, remote monitoring system 100 allows that remote monitor to view trend graph information of the host 199 and, if denied, then the remote monitor cannot view the trend graph information of the host. Notification settings allow the user of host monitoring application to view the current notification settings of the associated remote monitor. The notification settings can include an urgent low notification alert 1506, a low notification alert 1508, a high notification alert 1509 and a no data notification alert 1510, and each alerts associated status (e.g., associated threshold values and whether the alert is off or on). In some implementations, a user using host monitoring application can modify the remote monitors' settings using page 1500, for example, but in other implementations some or all of the settings can only be modified by the remote monitor, as indicated in FIG. 15.

Display page 1500 can also allow a user of the host monitoring application to pause and cancel the capabilities of remote monitor monitoring the host. A pause/resume control button 1514 can selectably stop and re-start remote monitoring capabilities of the remote monitor, such as stopping and starting notifications being sent to the remote monitor and/permission for the remote monitor to view sensor data of the host. Such a function can be useful in instances where a host does not always want a remote monitor to be monitoring the host. A specific example can include a baby sitter as a remote monitor. It may be desirable for the baby sitter to have remote monitoring capabilities when caring for a child being monitored by the host monitoring system, but stop the remote monitoring when the baby sitter is no longer caring for the child. This way, a new invitation need not be sent to the baby sitter each time the baby sitter cares for the child.

A delete Remote Monitor control button 1516 can be used to delete the remote monitor from the list of remote monitors that can monitor the host. In contrast to the pause/resume control 1514, deleting a remote monitor using the delete control 1516 would necessitate the host to re-invite the person to become a remote monitor in some implementations. As discussed elsewhere herein, remote monitoring system may have a predefined limit to the number of remote monitors that can monitor a host, thus it may be become necessary for the host to delete the remote monitor so that the host can add another remote monitor in some implementations.

In some implementations, remote monitoring system 100 sends a notification message to a remote monitor that has had its permissions or settings changed, or has been paused, resumed or canceled. This way, the remote monitor is aware of the change and is not relying on the previous configuration.

In addition, each of the pause, cancel, and resume functions may be configured globally across all of a host-patient's monitors instead of or in addition to individual monitors as described above. In the case of a global function, control buttons can be provided on page 1400 of FIG. 14, for example, where pressing the control button implements the function globally across all remote monitors monitoring the host.

Remote Monitoring Dashboard View

Figure 18A:
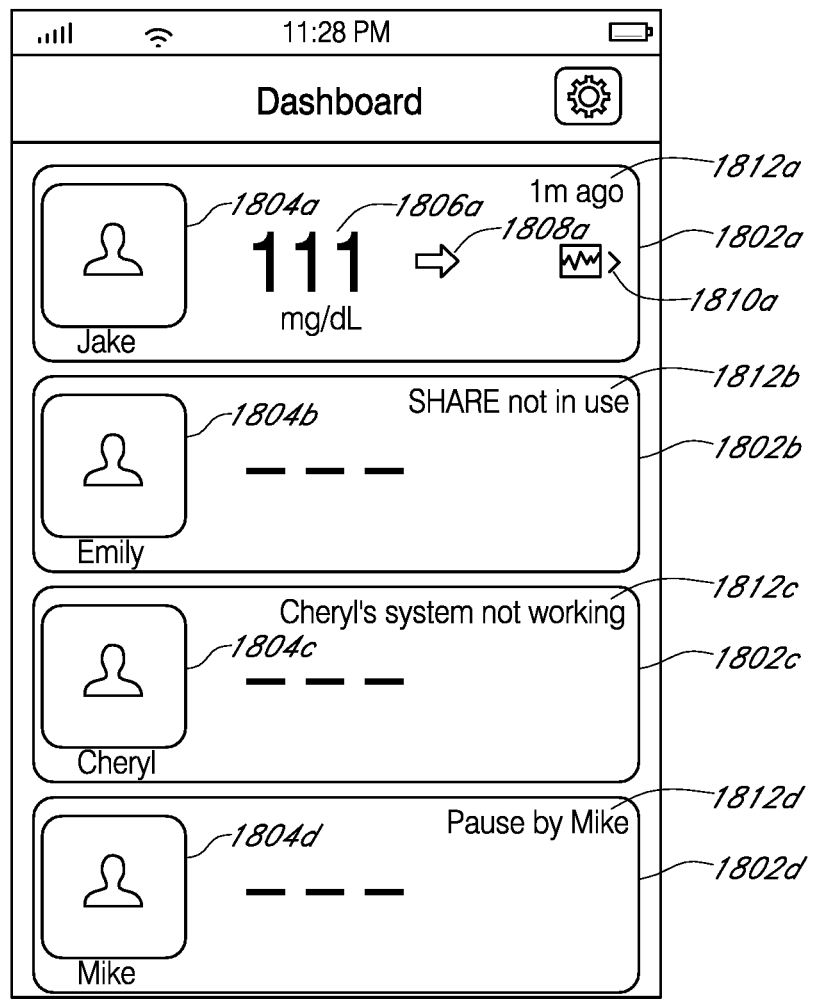
FIGS. 18A and 18B are two different implementations of a dashboard page in accordance with some implementations.
Figure 18B:
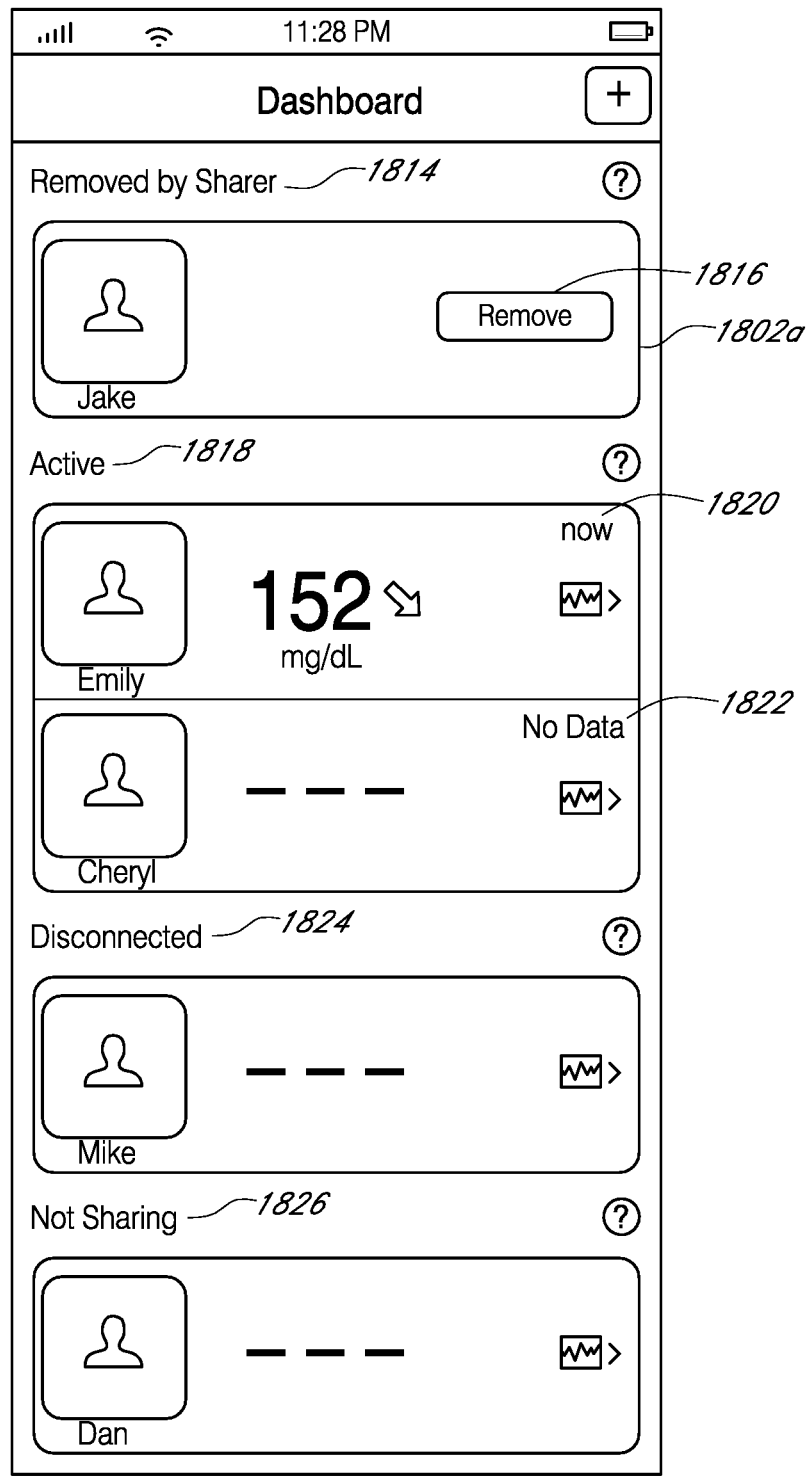

As discussed elsewhere herein, the remote monitor 114 can provide a so-called dashboard view of hosts it is monitoring. FIGS. 18A and 18B are two different implementations of dashboard page 1800 in accordance with some implementations. The dashboard 1800 can include a plurality of cells 1802*a*-1802*d*, each associated with a different host. Each cell 1802 can include identifiers of the host, such as a name of the host and a picture of the host 1804*a*-1804*d*.

In the implementation of FIG. 18A, each cell lists a current status of the cell, such as a time 1812*a* when the displayed analyte value 1806*a* was measured, a statement 1812*b* whether the host is using the remote monitoring system 100, a statement 1812*c* whether the hosts host monitoring system is working, or a statement 1812*d* indicating that the remote monitor has been paused, for example.

In the implementation of FIG. 18B, the cells 1802 can be grouped on page 1800 according to the status of the cell, such as removed 1814 by the host (referred to as Sharer in FIG. 18B), active 1818 (i.e., system is connected and providing data of the associated host to the remote monitor), disconnected 1824 (i.e. system is not connected, e.g., because receiver 102 is not in docking station 103 in the implementation of FIG. 2B) and not sharing 1826 (i.e. the host has paused the remote monitor). Further, cells within a group can be ordered by severity of the monitored condition or other criteria, as discussed elsewhere herein.

Cells 1802 can also include an indication of the permissions and/or settings of the remote monitor associated with that host. For example, a trend graph icon 1810 can indicate that the remote monitor has permission to view a trend graph of sensor data of that host.

Cells 1802 that are in the active group 1818 can also include information about the health condition being monitored. For example the cell 1802 can display the most current analyte concentration value 1806*a* that was provided to remote monitor and an trend arrow 1808*a* indicating a rate of change of the measured analyte. Further information can also be provided in the cell, such as a time associated with the measurement of the displayed analyte concentration or if data has not been received from the host monitoring system.

User selection of a cell 1802 can also cause the remote monitor to transition to another display page that provides additional information about the host associated with that cell. For example, the remote monitor can transition to a trend graph display (FIG. 19) associated with that host or a settings page (FIG. 17) associated with that host.

Trend Graph View

FIG. 19 is an exemplary page that provides a trend graph 914 of a host's monitored analyte concentration in accordance with some implementations. The trend graph can display a trend line 1916 of measured analyte concentrations, as well as low and high thresholds 1918 and 1920 that are used for alerting either the remote monitor 114 or the host monitoring system 198. The trend graph page can also include a user-selectable slider bar that allows a user to select different time frames of sensor data to view, such as three, six, 12 and 24 hour views. A picture of the host 1904 and name of the host 1902 can also be provided so that a remote monitor is not confused as to the individual being monitored in case the remote monitor is monitoring a plurality of different hosts.

In some implementations, the page of FIG. 19 can automatically be displayed when the remote monitoring application is initially opened responsive to a user directly opening the application and/or a user opening a remote monitoring notification on remote monitor 114 sent by server 110 or notification service 112, as discussed elsewhere wherein.

Remote Monitor Settings Page

Figure 17:
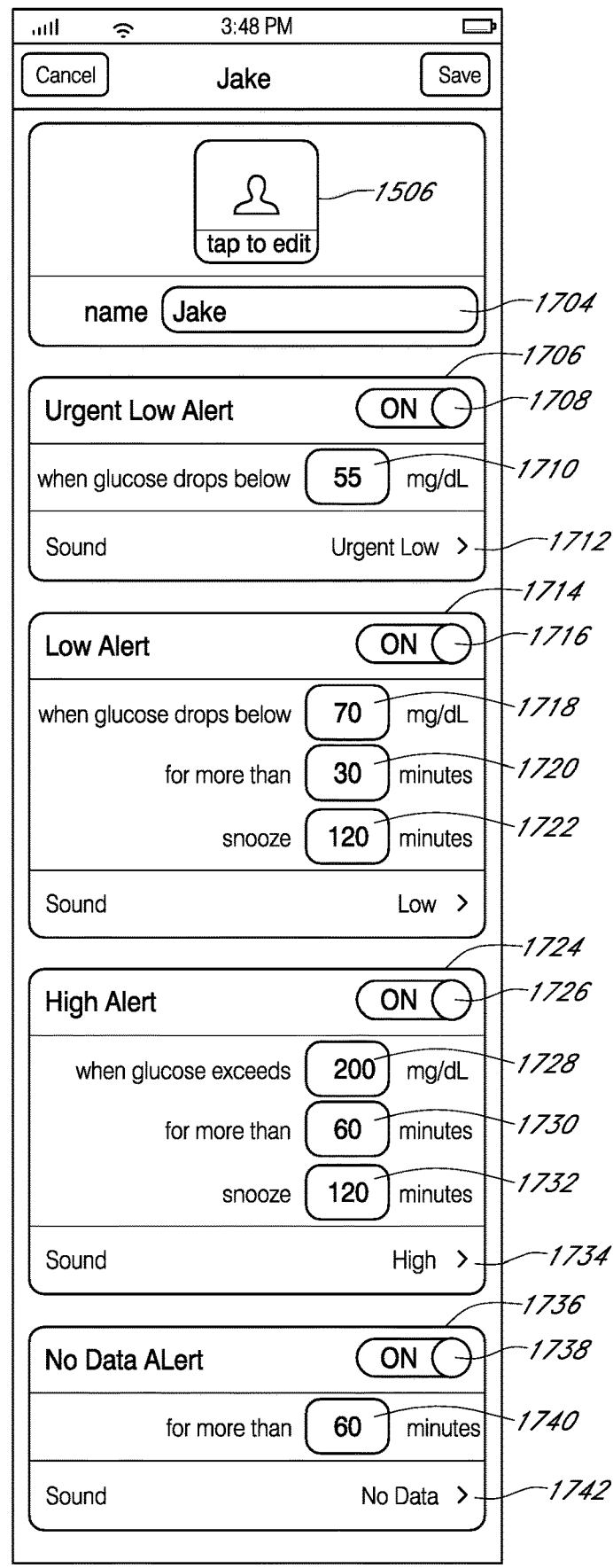
FIG. 17 is an implantation of a settings page that can allow the remote monitor to configure remote monitoring settings of a host in some implementations.

FIG. 17 is an implantation of a settings page 1700 that can allow the remote monitor to configure remote monitoring settings of a host. Settings page can include a picture filed that displays a picture of the host 1506 and a name field that displays a name of the host, both of which can be modified by the remote monitor using the settings page 1700. The settings page also includes settings for various alert/notification settings, such as an urgent low alert 1706, low alert 1714, high alert 1724 and not data alert 1736. The function of each of these alerts is discussed elsewhere herein. As illustrated in FIG. 17, the settings associated with each of these alerts can be modified, such as turning the alert on or off, the threshold value(s) associated with each alert and an alert sound associated with each alert.

Automatic Detection of New Receivers and Registration

In some implementations, receivers 102 need to be associated with a host 199 so that when glucose data gets to server 110, the data can be associated with the host. Accordingly, remote monitoring system 100 can assign a receiver to a host. This can initially be done through the pairing process discussed above with respect to block 1016 of FIG. 10. If a host receives a new receiver, to make a friendly user experience and prevent errors, the host monitoring application can see that a different serial number is being used, check with the server 110 to see if this is a new receiver or if this receiver is already owned by another host and asks the host via communication device 105 if this is their receiver and allows them to take ownership or it gives them an error telling them that it is already owned.

Accordingly, an exemplary detection of a new receiver process can be as follows. First, the host communication device 105 if a new receiver is being used by validating with server if the receiver is owned by someone else (via comparison of receiver serial numbers to a database, for example). If the server determines that no one else owns the receiver, then the host monitoring application asks if the user if he or she wants to make that receiver theirs. If yes, then the receiver and the data from that receiver are associated with that host.

Loss of Data Alert

In some example implementations, the secure server 110 may include a rule to automatically trigger a notification message or another communication mechanism (e.g., a phone call, short message service message, and the like) to a remote monitor 114 if data has not been received from host monitoring system 198 for a predetermined amount of time. This way, a user of remote monitor 114 can be aware that something may be wrong with host monitoring system 198 and attempt to contact the host.

Location-Based Alerts

In some example implementations, the secure server 110 may use the location of the receiver 102, gateway 104, host 199, and/or remote monitor(s) 114 when determining whether to send a notification message and/or determine destination of a notification message. For example, when a host-patient is in a first location and travels to a second location, the secure server 110 may, based on rules, select a first remote monitor 114A near the first location and, when the host-patent moves to the second location, select a second remote monitor 114B located near that second location. Location may also be used to vary alerts and notifications.

For example, the secure server 110 may vary the rules used to trigger an alert or notification based on the host-patient's location. Location may be used in combination with time as well, so the secure server 110 may vary thresholds associated with alerts and notifications based on location and time of day.

Acknowledgement Notifications

In some example implementations, the receiver 102 or gateway 104 may present a prompt (e.g., message, window, etc.) at a user interface requiring the host-patient to acknowledge the triggered alert and/or indicate what corrective action was taken in response to the alert. The prompt may include a list of options that the user can select (e.g., administered insulin, consumed carbohydrates, and the like) to indicate the corrective action that was taken. A notification message may be sent directly to one or more remote monitors 114, or through the secure server 110 and/or notification service 112, to the remote monitor(s), so that the remote monitors are aware that the patient has acknowledged the alert and/or that corrective action taken (and/or a description of the corrective action).

In addition, remote monitor 114 can allow a user to select from a plurality of pre-written messages to send to host monitoring system. A user can select the notification, whereupon the remote monitor displays a list of pre-written text messages that the user can select from to send to the host monitoring system. The messages can be selected by remote monitor to be relevant to the underlying cause that triggered the notification message. For instance, if the notification message was triggered by a low glucose level of the host, then the messages can be statements related to low glucose levels, such as "are you feeling okay?", "should you drink some orange juice?", and the like. Each message can be user selectable, and when selected, cause the remote monitor 114 to send the message to the host monitoring system for display on the host monitoring system. In addition, selection of the notification can automatically display a prompt to call the host, where user selection of the prompt causes the remote monitor to dial the phone number associated with the host (e.g. a smartphone that is part of the host monitoring system).

Motivational Messages

In some example implementations, the alerts sent to the receiver 102 and/or the notification messages may include motivational concepts. For example, if the host-patient has minimized the rate of change in glycemic levels, the secure server may send an alert to the receiver 102 and/or a notification message to remote monitor 114 stating "Great job maintaining your therapy-keep it up!." These motivational concepts may positively motivate the users to stay on the therapy program. In some example implementations, secure server 110 may include one or more events mapped to motivational concepts, so that triggering an event causes sending a message including the motivation concept to the receiver 102 and/or a remote monitor 114.

In some example implementations, the secure server 110 may use patterns, as noted above, to predict aspects of the patient-host's treatment. For example, a pattern may detect a glycemic change at a given time of day from a prior, established pattern, and then trigger a rule to send an alert to the receiver 102 and a notification to the receiver 114 stating, "Did you miss lunch?" These simple, non-technical query messages may evoke a better response from the host-patient to maintain a therapy, when compared to only providing measured data or statistics to a host-patient or remote monitor. In some example implementations, secure server 110 may include one or more events mapped to simple messages, so that triggering an event causes sending a message including the simple message to the receiver 102 and/or a remote monitor 114.

Audit Trail

The secure server 110 may also provide an audit trail. For example, the secure server 110 may store information related to when notifications were pushed to the remote monitor 114 using, for example, notification service 112, and when the remote monitor acknowledges the notification. The secure server 110 may also generate one or more reports to determine timelines and/or identify the effectiveness of remote monitors 114 (which can be used to select remote monitors and/or settings of system 100, such as alert settings, to more effectively monitor host 199).

Timestamping

In some implementations, analyte levels provided to remote monitors 114 may not be real-time. For example, while it may be desired to provide analyte values to remote monitors in real time, there may be a time delay between when the analyte value is measured by the analyte sensor system 8 and when the analyte level is provided to the remote monitor 114 and/or secure server 110. The delay may be due to any of the sensor system 8 only transmitting values periodically to the receiver 102, the receiver 102 transmitting only periodically values to gateway 104, the gateway having difficulty connecting to secure server 110, and secure server having difficulty connecting to remote monitor 114, for example. Consequently, in some implementations, a glucose value transmitted to the remote monitor 114 is displayed on the remote monitor with a time indicating the time the analyte value that triggered the notification corresponds to (e.g., the analyte value that met or exceeded the threshold that triggered the notification). The time may be the time of day the analyte value was measured (e.g., 2:10 p.m. Pacific Standard Time), or may be a difference in time since the analyte value was measured (e.g., 2 minutes ago, 30 minutes ago, 4 hours ago, etc.).

In addition, due to a time delay, the secure server 110 may end up sending a notification to remote monitor 114 based on a time delayed analyte value. In such a case, the notification can include a time associated with the alert that triggered the notification, such as "Mike's blood glucose went below 70 mg/dl at 2:10 P.S.T." or "Mike's blood glucose went below 70 mg/dl 25 minutes ago." Further, because a notification may not be viewed right away on the remote monitoring device, the remote monitoring device 114 can update any time associated with the notification until the notification is acknowledged.

To accommodate for differentness in time zones between a host and a remote monitor, the remote monitoring system can use a universal time and then convert the universal time to the time zone of the remote monitor, in accordance with some implementations. That is, a time stamp of a sensor data value generated by host monitoring system 198 and provided to secure server 110 can be in Universal Standard time (UST) or Greenwich Mean Time (GMT) and provided to the remote monitor 114 in the same universal time, whereby the remote monitor converts the universal time to the time zone in which the remote monitor is located.

In some implementations, due to difficulties with displaying time due to time lag and potential time zone differences between a host monitoring system 198 and remote monitor 114, which can cause confusion, notifications sent to remote monitor 114 do not display a time. To remedy the lack of time indication, some implementations automatically open the remote monitoring application on the remote monitor 114 and display the user's monitored health information upon user acknowledgment of the notification. The host's monitored health information that is initially displayed upon opening the application can include indications of the host's current state, such as the most current analyte value and/or a trend graph showing the past three hours of the host's measured analyte level.

Loss of Data Transmission

In some implementations, data may not be transmitted at times from the sensor system 8 to the secure server 110. This may be due to an unintentional lost data transmission connection between one or more of sensor system 8 and receiver 102, receiver 102 and gateway 104, docking station 103 and host communication device 105, or gateway 104 and secure server 110, for example. Or, the loss may be intentional, such as a user turning one or more of the components of the remote monitoring system 100 off, such as the receiver 102 or host communication device 105. In any such instance, the secure server 110 can be configured to send a notification indicating the loss of data transmission to one or more of the host monitoring system 198 and remote monitors 114A-114M.

However, it may be at times desirable not to send a notification so remote monitors 114 are not overly messaged. As an example, a host being monitored may be sleeping at night and get up to go to the kitchen for a drink of water. This can result in a loss of data transmission if the sensor system 8 is out of range from the receiver 102 resting on a nightstand of the host 199, for example. Consequently, a delay associated with loss of data transmission errors can be implemented so that the server 110 initiates a loss of data notification only if data is not received after a predetermined amount of time or after a predetermined number of attempted connection attempts with host monitoring system 198.

Further, it may be desirable to not send loss of data notifications every time there is a loss of data transmission, even if the loss of data transmission is for an extended period of time. For example, in the implementation of FIG. 2C, the docking station 103 may be stationary. Thus, a host may only be able to transmit health readings when the host has the receiver 102 docked in the docking station and the host is in sufficient proximity to the receiver and docking station for data transmission. However, a host may want to remove his or her receiver 102 from the docking station 103 when the host leaves for work, for example. It may not be desirable to trigger a notification to remote monitors 114 when the host removes the receiver from the docking station 103, as this may not be considered an important enough event.

Accordingly, in some implementations, the remote monitoring system 100 can determine that the receiver was removed from the docking station 103 as opposed to, for some reason, the host monitoring system 198 is not functioning correctly and not providing sensor data to the secure server. In one implementation, the remote monitoring system 100 determines that the receiver is not docked in the docking station 103 by monitoring transmissions from the cradle. For instance, transmissions from the docking station 103 that include information generated by the receiver 102 indicates that the receiver is docked and transmissions from the docking station 103 that do not include information generated by the receiver indicates that the receiver has been removed from the docking station.

Eyewear Display Device

Although the above disclosure is primarily described with respect to use of a hand-held computing device, it should be understood that other devices can be used instead or in place of the smart phone. For example, in some implementations, sensor data are transmitted from the personal computing device to a computing device in the form of eyewear and messages and information displayed on the eyewear for the user to view. An example of such eyewear is Google Glasses manufactured by Google, Inc. The user's eyewear interface can use a near-field radio link to receive data, either directly from sensor system 8, or through an intermediary device, such as receiver 102 or gateway 104.

In some implementations, transmission of the data may be event-driven. For example, driven by the occurrence of a low or high glucose excursion, as discussed herein.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), the public land mobile network, satellite networks, and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Moreover, as used herein the term "set" includes zero or more items, and the phrase "based on" can be used interchangeably (unless otherwise noted) with the phrase "based on at least." Other implementations may be within the scope of the following claims.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

Methods and devices that are suitable for use in conjunction with aspects of the preferred embodiments are disclosed in U.S. Pat. Nos. 4,757,022; 4,994,167; 6,001,067; 6,558, 321; 6,702,857; 6,741,877; 6,862,465; 6,931,327; 7,074, 307; 7,081,195; 7,108,778; 7,110,803; 7,134,999; 7,136, 689; 7,192,450; 7,226,978; 7,276,029; 7,310,544; 7,364, 592; 7,366,556; 7,379,765; 7,424,318; 7,460,898; 7,467, 003; 7,471,972; 7,494,465; 7,497,827; 7,519,408; 7,583, 990; 7,591,801; 7,599,726; 7,613,491; 7,615,007; 7,632, 228; 7,637,868; 7,640,048; 7,651,596; 7,654,956; 7,657, 297; 7,711,402; 7,713,574; 7,715,893; 7,761,130; 7,771, 352; 7,774,145; 7,775,975; 7,778,680; 7,783,333; 7,792, 562; 7,797,028; 7,826,981; 7,828,728; 7,831,287; 7,835, 777; 7,857,760; 7,860,545; 7,875,293; 7,881,763; 7,885, 697; 7,896,809; 7,899,511; 7,901,354; 7,905,833; 7,914, 450; 7,917,186; 7,920,906; 7,925,321; 7,927,274; 7,933, 639; 7,935,057; 7,946,984; 7,949,381; 7,955,261; 7,959, 569; 7,970,448; 7,974,672; 7,976,492; 7,979,104; 7,986, 986; 7,998,071; 8,000,901; 8,005,524; 8,005,525; 8,010, 174; 8,027,708; 8,050,731; 8,052,601; 8,053,018; 8,060, 173; 8,060,174; 8,064,977; 8,073,519; 8,073,520; 8,118, 877; 8,128,562; 8,133,178; 8,150,488; 8,155,723; 8,160, 669; 8,160,671; 8,167,801; 8,170,803; 8,195,265; 8,206, 297; 8,216,139; 8,229,534; 8,229,535; 8,229,536; 8,231, 531; 8,233,958; 8,233,959; 8,249,684; 8,251,906; 8,255, 030; 8,255,032; 8,255,033; 8,257,259; 8,260,393; 8,265, 725; 8,275,437; 8,275,438; 8,277,713; 8,280,475; 8,282, 549; 8,282,550; 8,285,354; 8,287,453; 8,290,559; 8,290, 560; 8,290,561; 8,290,562; 8,292,810; 8,298,142; 8,311, 749; 8,313,434; 8,321,149; 8,332,008; 8,346,338; 8,364, 229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-

0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; U.S. Patent Publication No. 2005-0182451-A1; U.S. Patent Publication No. 2013000536650A1; and U.S. Patent Publication No. 2013-0053666-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS"; U.S. application Ser. No. 13/779,607 filed on Feb. 27, 2013 and entitled "ZWITTERION SURFACE MODIFICATIONS FOR CONTINUOUS SENSORS"; U.S. application Ser. No. 13/780,808 filed on Feb. 28, 2013 and entitled "SENSORS FOR CONTINUOUS ANALYTE MONITORING, AND RELATED METHODS"; U.S. application Ser. No. 13/784,523 filed on Mar. 4, 2013 and entitled "ANALYTE SENSOR WITH INCREASED REFERENCE CAPACITY"; U.S. application Ser. No. 13/789,371 filed on Mar. 7, 2013 and entitled "MULTIPLE ELECTRODE SYSTEM FOR A CONTINUOUS ANALYTE SENSOR, AND RELATED METHODS"; U.S. application Ser. No. 13/789,279 filed on Mar. 7, 2013 and entitled "USE OF SENSOR REDUNDANCY TO DETECT SENSOR FAILURES"; U.S. application Ser. No. 13/789,339 filed on Mar. 7, 2013 and entitled "DYNAMIC REPORT BUILDING"; U.S. application Ser. No. 13/789,341 filed on Mar. 7, 2013 and entitled "REPORTING MODULES"; U.S. application Ser. No. 13/790,281 filed on Mar. 8, 2013 and entitled "SYSTEMS AND METHODS FOR MANAGING GLYCEMIC VARIABILITY"; U.S. application Ser. No. 13/796,185 filed on Mar. 12, 2013 and entitled "SYSTEMS AND METHODS FOR PROCESSING ANALYTE SENSOR DATA"; U.S. application Ser. No. 13/796,642 filed on Mar. 12, 2013 and entitled "SYSTEMS AND METHODS FOR PROCESSING ANALYTE SENSOR DATA"; U.S. application Ser. No. 13/801,445 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/802,424 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/802,237 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/802,317 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/830,540 filed on Mar. 14, 2013 and entitled "TRANSCUTANEOUS ANALYTE SENSORS, APPLICATORS THEREFOR, AND ASSOCIATED METHODS"; U.S. application Ser. No. 13/829,722 filed on Mar. 14, 2013 and entitled "TRANSCUTANEOUS ANALYTE SENSORS, APPLICATORS THEREFOR, AND ASSOCIATED METHODS"; U.S. application Ser. No. 13/830,330 filed on Mar. 14, 2013 and entitled "SYSTEMS AND METHODS FOR PROCESSING AND TRANSMITTING SENSOR DATA"; U.S. application Ser. No. 13/827,577 filed on Mar. 14, 2013 and entitled "SYSTEMS AND METHODS FOR PROCESSING AND TRANSMITTING SENSOR DATA"; U.S. application Ser. No. 13/830,330 filed on Mar. 14, 2013 and entitled "SYSTEMS AND METHODS FOR PROCESSING AND TRANSMITTING SENSOR DATA"; and U.S. application Ser. No. 13/827,119 filed on Mar. 14, 2013 and entitled "ADVANCED CALIBRATION FOR ANALYTE SENSORS".

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of configuring alert settings for a remote monitor device, comprising:
    defining, at a host monitor device, a first set of rules for access, by a first remote monitor device, to host analyte data generated by a host analyte sensor system in communication with the host monitor device and stored at a server;
    presenting, at the first remote monitor device, an invitation to access the host analyte data;
    accepting, at the first remote monitor device, the invitation;
    receiving, at the first remote monitor device, subsequent to accepting the invitation, a first notification indicative of the host analyte data in accordance with the first set of rules;
    presenting, at the first remote monitor device, a user interface mechanism for modifying at least one of the first set of rules, by the first remote monitor device, to generate at least one modified rule for the first remote monitor device independent of the first set of rules defined at the host monitor device;

determining if the at least one of the first set of rules has been modified by the first remote monitor device through the user interface mechanism; and upon determining that the at least one of the first set of rules has been modified, providing the at least one modified rule to the server to be stored at the server.

2. The method of claim 1, further comprising:

defining, at the host monitor device, a second set of rules for access, by a second remote monitor device, to the host analyte data; and presenting, at the second remote monitor device, a second invitation to access the host analyte data;

accepting, at the second remote monitor device, the second invitation;

receiving, at the second remote monitor device, subsequent to accepting the second invitation, a second notification indicative of the host analyte data in accordance with the second set of rules;

presenting, at the second remote monitor device, a second user interface mechanism for modifying at least one of the second set of rules, by the second remote monitor device, to generate at least one modified rule for the second remote monitor device independent of the second set of rules defined at the host monitor device;

determining if the at least one of the second set of rules has been modified by the second remote monitor device through the second user interface mechanism; and upon determining that the at least one of the second set of rules has been modified, providing the at least one modified rule for the second remote monitor device to the server to be stored at the server.

3. The method of claim 1, wherein the at least one modified rule for the first remote monitor device is in compliance with the first set of rules defined by the host monitor device.

4. The method of claim 1, further comprising: receiving, at the first remote monitor device, a second notification indicative of the host analyte data in accordance with the at least one modified rule.

5. The method of claim 1, wherein the first notification comprises the host analyte data.

6. The method of claim 1, wherein the first set of rules defines a time limit for the first remote monitor device to access the host analyte data.

7. The method of claim 1, wherein the first set of rules defines a count limit for the first remote monitor device to access the host analyte data.

8. An analyte monitoring system for monitoring analyte levels of a host, comprising:

a host analyte sensor system configured to generate host analyte data corresponding to the analyte levels of the host;

a host monitor device configured to define a first set of rules for access by a first remote monitor device to the host analyte data generated by the host analyte sensor system; and the first remote monitor device configured to:
present an invitation to access the host analyte data;
transmit an acceptance of the invitation to a server;
receive, subsequent to the acceptance, a first notification indicative of the host analyte data in accordance with the first set of rules;
present a user interface mechanism for modifying at least one of the first set of rules to generate at least one modified rule for the first remote monitor device independent of the first set of rules defined at the host monitor device;

determine if the at least one of the first set of rules has been modified through the user interface mechanism; and upon determining that the at least one of the first set of rules has been modified, provide the at least one modified rule to the server to be stored at the server.

9. The analyte monitoring system of claim 8, further comprising:

the server configured to:
in response to receiving the acceptance from the first remote monitor device, send the first notification indicative of the host analyte data in accordance with the first set of rules to the first remote monitor device; and
in response to receiving the at least one modified rule, send a second notification to the first remote monitor device in accordance with the at least one modified rule.

10. The analyte monitoring system of claim 8, wherein:

the host monitor device is further configured to define a second set of rules for access, by a second remote monitor device, to the host analyte data;

the second remote monitor device configured to:
present a second invitation to access the host analyte data;
transmit a second acceptance of the invitation to the server;
receive, subsequent to the second acceptance, a second notification indicative of the host analyte data in accordance with the second set of rules;
present a second user interface mechanism for modifying at least one of the second set of rules to generate at least one modified rule for the second remote monitor device independent of the second set of rules defined at the host monitor device;
determine if the at least one of the second set of rules has been modified through the user interface mechanism; and
upon determining that the at least one of the second set of rules has been modified, provide the at least one modified rule for the second remote monitor device to the server to be stored at the server.

11. The analyte monitoring system of claim 8, wherein the at least one modified rule for the first remote monitor device is in compliance with the first set of rules defined by the host monitor device.

12. The analyte monitoring system of claim 8, wherein the first remote monitor device is further configured to receive a second notification indicative of the host analyte data in accordance with the at least one modified rule.

13. The analyte monitoring system of claim 8, wherein the server is further configured to analyze the host analyte data and provide, to the first remote monitor device, a second notification in accordance with the at least one modified rule.

14. The analyte monitoring system of claim 8, wherein the server is further configured to confirm an identity of at least one of the host monitor device or the first remote monitor device.

15. The analyte monitoring system of claim 8, wherein the first notification comprises the host analyte data.

16. The analyte monitoring system of claim 8, wherein the first set of rules defines a time limit for the first remote monitor device to access the host analyte data.

17. The analyte monitoring system of claim 8, wherein the first set of rules defines a count limit for the first remote monitor device to access the host analyte data.

* * * * *